(12) United States Patent
Bailey et al.

(10) Patent No.: US 7,767,818 B2
(45) Date of Patent: Aug. 3, 2010

(54) HEPATITIS C INHIBITOR DIPEPTIDE ANALOGS

(75) Inventors: Murray Douglas Bailey, Pierrefonds (CA); Elise Ghiro, Laval (CA); Nathalie Goudreau, St-Laurent (CA); Teddy Halmos, Laval (CA); Montse Llinas-Brunet, Dollard-des-Ormeaux (CA); Marc-Andre Poupart, Laval (CA); Jean Rancourt, Laval (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/368,321

(22) Filed: Feb. 10, 2009

(65) Prior Publication Data

US 2009/0156822 A1  Jun. 18, 2009

Related U.S. Application Data

(62) Division of application No. 11/185,671, filed on Jul. 19, 2005, now Pat. No. 7,511,157.

(60) Provisional application No. 60/589,435, filed on Jul. 20, 2004.

(51) Int. Cl.
C07D 215/06 (2006.01)
C07D 215/12 (2006.01)
C07D 215/16 (2006.01)
C07D 413/04 (2006.01)

(52) U.S. Cl. ........................ 546/155; 548/216

(58) Field of Classification Search ................ 548/216; 546/155
See application file for complete search history.

(56) References Cited

U.S. PATENT DOCUMENTS

| | | | |
|---|---|---|---|
| 4,691,007 A | 9/1987 | Dutta et al. | |
| 5,164,402 A | 11/1992 | Brighty | |
| 5,633,388 A | 5/1997 | Diana et al. | |
| 5,962,638 A | 10/1999 | Naumann et al. | |
| 5,994,311 A | 11/1999 | Eichner et al. | |
| 6,143,715 A | 11/2000 | Llinas-Bruent et al. | |
| 6,159,938 A | 12/2000 | Gyorkos et al. | |
| 6,187,905 B1 | 2/2001 | Hurst et al. | |
| 6,277,830 B1 | 8/2001 | Ganguly et al. | |
| 6,323,180 B1 | 11/2001 | Llinas-Bruent | |
| 6,329,379 B1 | 12/2001 | Llinas-Brunet et al. | |
| 6,337,394 B2 | 1/2002 | Karisson et al. | |
| 6,410,531 B1 | 6/2002 | Llinas-Brunet et al. | |
| 6,420,380 B2 | 7/2002 | Llinas-Brunet et al. | |
| 6,455,571 B1 | 9/2002 | Maring et al. | |
| 6,534,523 B1 | 3/2003 | Llinas-Brunet et al. | |
| 6,608,027 B1 | 8/2003 | Tsantrizos et al. | |
| 6,642,204 B2 | 11/2003 | Llinas-Brunet | |
| 6,767,991 B1 | 7/2004 | Llinas-Bruent | |
| 6,846,806 B2 | 1/2005 | Priestley | |
| 6,867,185 B2 | 3/2005 | Campbell et al. | |
| 6,869,964 B2 | 3/2005 | Campbell et al. | |
| 6,872,805 B2 | 3/2005 | Campbell et al. | |
| 6,878,722 B2 | 4/2005 | Campbell et al. | |
| 6,908,901 B2 | 6/2005 | Bailey et al. | |
| 6,919,423 B2 | 7/2005 | Llinas-Brunet | |
| 6,939,854 B2 | 9/2005 | Priestley | |
| 6,995,174 B2 | 2/2006 | Wang et al. | |
| 7,041,698 B2 | 5/2006 | Ripka et al. | |
| 7,091,184 B2 | 8/2006 | Llinas-Bruent et al. | |
| 7,132,504 B2 | 11/2006 | Scola et al. | |
| 2002/0020503 A1 | 2/2002 | Luca | |
| 2002/0111313 A1 | 8/2002 | Campbell et al. | |
| 2003/0191067 A1 | 10/2003 | Llinas-Brunet | |
| 2004/0033959 A1 | 2/2004 | Chen et al. | |
| 2004/0077551 A1 | 4/2004 | Campbell et al. | |
| 2004/0106559 A1 | 6/2004 | Wang et al. | |
| 2005/0020503 A1 | 1/2005 | Llinas-Brunet et al. | |
| 2005/0187165 A1 | 8/2005 | Scola et al. | |
| 2006/0019905 A1 | 1/2006 | Bailey et al. | |
| 2006/0046965 A1 | 3/2006 | Bailey et al. | |
| 2006/0258868 A1* | 11/2006 | Bailey et al. ................ | 546/152 |

FOREIGN PATENT DOCUMENTS

| | | |
|---|---|---|
| CA | 2445938 A1 | 2/2000 |
| CA | 2429359 A1 | 8/2002 |
| CA | 2486308 A1 | 12/2003 |
| DE | 19600034 A1 | 7/1997 |
| GB | 2337262 A1 | 11/1999 |
| JP | 05155827 | 6/1993 |
| JP | 10298151 | 10/1998 |
| JP | 1135478 | 2/1999 |

(Continued)

OTHER PUBLICATIONS

Caplus, RN 552335-40-7, retrieved on Apr. 17, 2008.

(Continued)

*Primary Examiner*—Rebecca L Anderson
*Assistant Examiner*—Shawquia Young
(74) *Attorney, Agent, or Firm*—Michael P. Morris; Mary-Ellen M. Devlin; Philip I. Datlow

(57) ABSTRACT

Compounds of formula (I):

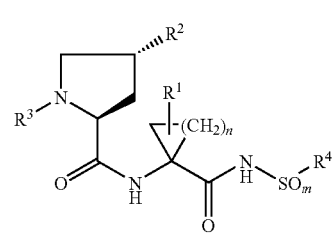

wherein $R^1$, $R^2$, $R^3$, $R^4$, n and m are as defined herein. The compounds are useful as inhibitors of HCV NS3 protease.

19 Claims, No Drawings

FOREIGN PATENT DOCUMENTS

| | | |
|---|---|---|
| JP | 11127861 | 5/1999 |
| JP | 11137252 | 5/1999 |
| JP | 11292840 | 10/1999 |
| JP | 2001103993 | 4/2001 |
| WO | 9533763 | 12/1995 |
| WO | 9706804 A1 | 2/1997 |
| WO | 9743310 A1 | 11/1997 |
| WO | 9817679 A1 | 4/1998 |
| WO | 9822496 A2 | 5/1998 |
| WO | 9846597 A1 | 10/1998 |
| WO | 9846630 A1 | 10/1998 |
| WO | 9853814 | 12/1998 |
| WO | 9907733 | 2/1999 |
| WO | 9907734 | 2/1999 |
| WO | 9938888 A2 | 8/1999 |
| WO | 9950230 A1 | 10/1999 |
| WO | 9964442 A1 | 12/1999 |
| WO | 0009543 | 2/2000 |
| WO | 0009558 | 2/2000 |
| WO | 0020400 A1 | 4/2000 |
| WO | 0031129 A1 | 6/2000 |
| WO | 0059929 | 10/2000 |
| WO | 0102424 A2 | 1/2001 |
| WO | 0107407 A1 | 2/2001 |
| WO | 0116357 A2 | 3/2001 |
| WO | 0132691 A1 | 5/2001 |
| WO | 0140262 A1 | 6/2001 |
| WO | 0158929 A1 | 8/2001 |
| WO | 0164678 A2 | 9/2001 |
| WO | 0174768 A2 | 10/2001 |
| WO | 0177113 A2 | 10/2001 |
| WO | 0181325 A2 | 11/2001 |
| WO | 0208187 A1 | 1/2002 |
| WO | 0208198 A2 | 1/2002 |
| WO | 0208244 A2 | 1/2002 |
| WO | 0208251 A2 | 1/2002 |
| WO | 0208256 A2 | 1/2002 |
| WO | 0218369 A2 | 3/2002 |
| WO | 02060926 A2 | 8/2002 |
| WO | 02079234 A1 | 10/2002 |
| WO | 03053349 | 7/2003 |
| WO | 03064416 | 8/2003 |
| WO | 03064455 | 8/2003 |
| WO | 03064456 | 8/2003 |
| WO | 03099274 | 12/2003 |
| WO | 03099316 | 12/2003 |
| WO | 2004032827 A2 | 4/2004 |
| WO | 2004043339 A2 | 5/2004 |
| WO | 2004101602 A2 | 11/2004 |
| WO | 2004101605 A1 | 11/2004 |
| WO | 2004103996 | 12/2004 |
| WO | 2004103996 A1 | 12/2004 |
| WO | 2005028501 A1 | 3/2005 |
| WO | 2005046712 A1 | 5/2005 |
| WO | 2006000085 A1 | 1/2006 |

OTHER PUBLICATIONS

Orvieto; Novel, Potent Phenethylamide Inhibitors of the Hepatitis C Virus (HCV) NS3 Protease: Probing the Role of P2 Aryloxyprolines with Hybrid Structures; Bioorganic & Medicinal Chemistry Letters 13: (2003) 2745-2748.
Nizi; Capped dipeptide phenethylamide inhibitors of the HCV NS3 protease; Bioorganic & Medicinal Chemistry Letters 14: (2004) 2151-2154.
Chronic Hepatitis C: Current Disease Management [online]; Retrieved from the internet, URL: http://digestive.niddk.nih.gov/ddiseases/pubs/chronichepc/index.htm>.
Smith, et al; Synthesis and Pharmacological Activity of Angiotensin Converting Enzyme Inhibitors: N-(Mercaptoacyl)-4-substituted-(S)-prolines; Journal of Medicinal Chemistry; 1988; vol. 31; pp. 875-885.
Perrone; 2-(Aryloxy)ethylamine Derivatives: Ring Opened Congeners of Long Chain 1-Arylpiperazines with High 5-HT1A Receptor Affinity and Selectivity Versus D2 and a1 Receptors; Medicinal Chemistry Research; 1999; vol. 9; No. 5; pp. 340-353.
Gaucher, et al; Palladium (0) Catalyzed Tandem Alkylation and SN' Cyclization of 1,4-Dichlorobut-2-ene by the N-(Diphenylmethylene) acetonitrile. A Stereoselective Synthesis of 1-Aminocyclopropanecarboxylic Acids; Tetrahedron Letters; 1995; vol. 36; No. 17; pp. 2979-2982.
Fliche, et al; Enantioselective synthesis of (1R,2S) and (1S,2S) dehydrocoronamic acids; Synthetic Communications; 1994; vol. 24; No. 20; pp. 2873-2876.
Chen, et al; Chirally selective hydrolysis of D, L amino acid esters by alkaline protease; J. Chem, Soc. Chem. Commun.; 1986; vol. 20; pp. 1514-1516.
Llinas-Brunet; et al; Peptide-based inhibitors of the hepatitis C virus serine protease; Bioorganic & Medicinal Chemistry Letters; 1998; vol. 8; pp. 1713-1718.
Gershonov, et al; 1-Aminocyclobutanecarboxylic acid derivatives as novel structural elements in bioactive peptides: application to tuftsin analogs; Journal of Medicinal Chemistry; 1996; vol. 39; No. 24; pp. 4833-4843.
Chen, et al; Kinetic resolution of esters of amino acids in t-butanol containing 5% water catalyzed by a stable industrial alkaline protease; Chirality; 1994; vol. 6; pp. 572-576.
Ogawa, et al; 2,3-Methanophenylalanine and.Alpha., .Beta.-Dehydrophenylalanine Derivatives as Chymotrypsin Inhibitor; Pept. Chem. (1990); vol. 27; pp. 379-382.
Llinas-Brunet, et al; Studies on the C-terminal of Hexapeptide Inhibitors of the Hepatitis C Virus Serine Protease; Bioorganic & Medicinal Chemistry Letters; 1998; vol. 8; pp. 2719-2724, 1998.
Huang, et al; Olefin Methathesis-Active Ruthenium Complexes Bearing a Nucleophilic Carbene Lignad; Journal of American Chemical Society; 1999; vol. 121; pp. 2674-2678.
Kingsbury, et al; A Recycable Ru-Based Methathesis Catalyst; Journal of American Chemical Society; 1999; vol. 121; pp. 791-799.
Krchnak, et al; Polymer-Supported Mitsunobu Ether Formation and its Use in Combinatorial Chemistry; Tetrahedron Letters; 1995; vol. 36; No. 35; pp. 6193-6196.
Lohmann, et al; Replication of Subgenomic Hepatitis C Virus RNAs in a Hepatoma Cell Line; Science; Jul. 2, 1999; vol. 285; pp. 110-113.
Miller, et al; Application of Ring-Closing Methathesis to the Synthesis of Rigidified Amino Acids and Peptides; Journal of American Chemical Society; 1996; vol. 118; pp. 9606-9614.
Mitsunobu; The Use of Diethyl Azodicarboxylate and Triphenylphosphine in Synthesis and Transformation of Natural Products; Synthesis (Reviews); pp. 1-28.
Rano, et al; Solid Phase Synthesis of Aryl Ethers via the Mitsunobu Reaction; Tetrahedron Letters; 1995; vol. 36; No. 22; pp. 3789-3792.
Still, et al; Rapid Chromatographic Technique for Preparative Separations with Moderate Resolution; Journal of Organic Chemistry; 1978; vol. 43; No. 14.
Llinas-Brunet, et al; Peptide-Based Inhibitors of the Hepatitis C Virus Serine Protease; Bioorganic & Medicinal Chemistry Letters; 1998; vol. 8; No. 13; pp. 1713-1718.
Ingallinella, et al; Potent Peptide Inhibitors of Human Hepatitis C Virus NS3 Protease Are Obtained by Optimizing the Cleavage Products; Biochemistry; 1998; vol. 37; pp. 8906-8914.
Landro; Mechanistic Role of an NS4A Peptide Cofactor with the Truncated NS3 Protease of Hepatitis C. Virus: Elucidation of the NS4A Stimulatory Effect via Kinetic Analysis and Inhibitor Mapping; Biochemistry; 1997; vol. 36; pp. 9340-9348.
Mori, et al; The N-Terminal Region of NS3 Serin Proteinase of Hepatitis C Virus Is Important to Maintain Its Enzymatic Integrity; Biochemical and Biophysical Research Communications; 1997; vol. 231; No. 3; pp. 738-742.
Chu, et al; Structure of Sch 68631: A New Hepatitis C Virus Proteinase Inhibitor from *Streptomyces* sp; Tetrahedron Letters; 1996; vol. 37; No. 40; pp. 7229-7232.

Matsumoto, et al; 3D Modeling of HCV Protease and Computer Screening of its Inhibitors; Antiviral Research; 1996; vol. 30; No. 1; pp. A23 (abstract 19).
Steinkuehler; et al; Product Inhibition of the Hepatitis C Virus NS3 Protease; Biochemistry; 1998; vol. 37; pp. 8899-8905.
Derwent Abstract: AN 2001-435746 [47] (JP2001103993).
Derwent Abstract: AN 1999-040664 [04] (JP10298151).
Derwent Abstract: AN 1999-350322 [30] (JP11127861).
Derwent Abstract: AN 2000-018687 [02] (JP11292840).
Derwent Abstract: AN 1999-186214 [16] (JP11035478).
Derwent Abstract: AN 1999-374374 [32] (JP11137252).
Naps and Johns; Optically Active Mono-substituted Succinic Acids and Derivatives; Journal of American Chemical Society; vol. 62; 1940, pp. 2450-2457.
Sibal, et al; Nonhuman Primates: A Critical Role in Current Disease Research; ILAR Journal; 2001; vol. 42; No. 2; pp. 74-84.

* cited by examiner

HEPATITIS C INHIBITOR DIPEPTIDE ANALOGS

RELATED APPLICATIONS

This application is a divisional of U.S. application Ser. No. 11/185,671, filed on Jul. 19, 2005, and benefit of U.S. Provisional Application Ser. No. 60/589,435, filed on Jul. 20, 2004, is hereby claimed.

FIELD OF THE INVENTION

The present invention relates to compounds, processes for their synthesis, compositions and methods for the treatment of hepatitis C virus (HCV) infection. In particular, the present invention provides novel peptide analogs, pharmaceutical compositions containing such analogs and methods for using these analogs in the treatment of HCV infection.

BACKGROUND OF THE INVENTION

Hepatitis C virus (HCV) is the major etiological agent of post-transfusion and community-acquired non-A non-B hepatitis worldwide. It is estimated that over 200 million people worldwide are infected by the virus. A high percentage of carriers become chronically infected and many progress to chronic liver disease, so-called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis, however, the Center for Disease Control does not presently recommend immunoglobulin treatment for this purpose. The lack of an effective protective immune response is hampering the development of a vaccine or adequate post-exposure prophylaxis measures, so in the near-term, hopes are firmly pinned on antiviral interventions.

Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Interferon in combination with ribavirin has been approved for the treatment of patients with chronic hepatitis C. However, side effects caused by IFN (such as retinopathy, thyroiditis, acute pancreatitis, depression) are not alleviated with this combination therapy. Pegylated forms of interferons such as PEG-Intron® and Pegasys® can apparently partially address these deleterious side effects but antiviral drugs still remain the avenue of choice for oral treatment of HCV.

Therefore, a need exists for the development of effective antiviral agents for treatment of HCV infection that overcome the limitations of existing pharmaceutical therapies.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature nonstructural proteins (NS2, NS3, NS4A, NS4B, NS5A, and NS5B) is effected by two viral proteases. The first cleaves at the NS2-NS3 junction (henceforth referred to as NS2/3 protease); the second is a serine protease contained within the N-terminal region of NS3 (NS3 protease) and mediates all the subsequent cleavages downstream of NS3, both in cis, at the NS3-NS4A cleavage site, and in trans, for the remaining NS4A-NS4B, NS4B-NS5A and NS5A-NS5B sites. The NS4A protein appears to serve multiple functions, acting as a cofactor for the NS3 protease and possibly assisting in the membrane localization of NS3 and other viral replicase components. The complex formation of the NS3 protease with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

A general strategy for the development of antiviral agents is to inactivate virally encoded enzymes that are essential for the replication of the virus. In a two day clinical trial, it has been shown that the HCV NS3 protease inhibitor BILN 2061 is effective in rapidly reducing viral loads in patients infected with the hepatitis C virus (*Gastroenterology* (2004) 127(5): 1347-1355), thus providing proof of principle of the clinical antiviral activity of HCV NS3 protease inhibitors.

The NS3 protease has been found to potentially have an additional impact by blocking the IFN-mediated cellular antiviral activity in the infected cell (Foy et al., *Science* (2003) 300: 1145-1148). This lends credence to a hypothesis that the NS3/NS4A protease may represent a dual therapeutic target, the inhibition of which may both block viral replication and restore Interferon response of HCV infected cells.

Inhibitors of the HCV NS3 protease have been described in WO 00/09543 (Boehringer Ingelheim), WO 03/064456 (Boehringer Ingelheim), WO 03/064416 (Boehringer Ingelheim), WO 2004/101602 (Boehringer Ingelheim), WO 2004/101605 (Boehringer Ingelheim), WO 2004/103996 (Boehringer Ingelheim), WO 02/060926 (Bristol-Myers Squibb), WO 03/053349 (Bristol-Myers Squibb), WO 03/099316 (Bristol-Myers Squibb), WO 03/099274 (Bristol-Myers Squibb), WO 2004/032827 (Bristol-Myers Squibb) and WO 2004/043339 (Bristol-Myers Squibb). As well, phenethylamide dipeptide inhibitors of the HCV NS3 protease have been described in Orvieto et al, *Bioorganic & Medicinal Chemistry Letters* (2003) 13: 2745-8 and in Nizi et al, *Bioorganic & Medicinal Chemistry Letters* (2004) 14: 2151-4.

In WO 2004/043339, WO 03/099274, WO 03/053349, and WO 02/060926, dipeptide synthetic intermediates bearing a tert-butyloxycarbonyl group are described.

The present invention now provides novel compounds that are inhibitory to the NS3 protease. Furthermore, compounds being active in cell culture are provided.

An advantage of one aspect of the present invention resides in the fact that compounds according to this invention specifically inhibit the NS3 protease and do not show significant inhibitory activity against other serine proteases such as human leukocyte elastase (HLE), porcine pancreatic elastase (PPE), or bovine pancreatic chymotrypsin, or cysteine proteases such as human liver cathepsin B (Cat B).

SUMMARY OF THE INVENTION

Included in the scope of the invention is a compound of formula (I):

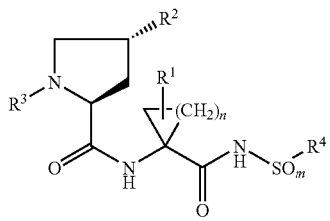

(I)

wherein
n is 1 or 2;
m is 1 or 2;
$R^1$ is $(C_{1-6})$alkyl, $(C_{2-6})$alkenyl, or $(C_{2-6})$alkynyl; wherein the $(C_{1-6})$alkyl, $(C_{2-6})$alkenyl, and $(C_{2-6})$alkynyl are optionally substituted at one or more substitutable positions with from one to three halogen atoms;
$R^2$ is selected from —NH—$R^{20}$, —O—$R^{20}$, —S—$R^{20}$, —SO—$R^{20}$, —SO$_2$—$R^{20}$, —OCH$_2$—$R^{20}$, and —CH$_2$O—$R^{20}$, wherein
  $R^{20}$ is aryl or Het, the aryl and Het each being optionally substituted with $R^{200}$, wherein
  $R^{200}$ is one to four substituents each independently selected from H, halogen, cyano, $(C_{1-6})$alkyl, $(C_{3-7})$cycloalkyl, aryl-$(C_{1-6})$alkyl-, aryl, Het, oxo, thioxo, —OR$^{201}$, —SR$^{201}$, —SOR$^{201}$, —SO$_2$R$^{201}$, —N(R$^{202}$)R$^{201}$ and —CON(R$^{202}$)R$^{201}$; wherein each of the alkyl, cycloalkyl, aryl and Het is optionally further substituted with $R^{2000}$;
  $R^{201}$ in each case is independently selected from H, $(C_{1-6})$alkyl, aryl, $(C_{2-4})$alkenyl, $(C_{2-4})$alkynyl, —CO—$(C_{1-6})$alkyl and —CO—O—$(C_{1-6})$alkyl, wherein each of the alkyl and aryl is optionally further substituted with $R^{2000}$;
  $R^{202}$ is H or $(C_{1-6})$alkyl;
  $R^{2000}$ is one to three substituents each independently selected from halogen, $R^{2003}$, aryl, Het, —OR$^{2001}$, —SR$^{2001}$, —SOR$^{2001}$, —SO$_2$R$^{2001}$, cyano and —N(R$^{2002}$)(R$^{2001}$), wherein the aryl and Het are each optionally substituted with one, two or three substituents each independently selected from $(C_{1-6})$alkyl and —O—$(C_{1-6})$alkyl;
  $R^{2001}$ in each case is independently selected from aryl, aryl-$(C_{1-6})$alkyl-, —C(O)—R$^{2003}$, —C(O)O—R$^{2003}$, —CON(R$^{2002}$)(R$^{2004}$) and R$^{2004}$;
  $R^{2002}$ in each case is independently selected from H and $(C_{1-6})$alkyl;
  $R^{2003}$ in each case is independently selected from $(C_{1-8})$alkyl, $(C_{3-7})$cycloalkyl and $(C_{3-7})$cycloalkyl-$(C_{1-4})$alkyl-, wherein the $(C_{3-7})$cycloalkyl and $(C_{3-7})$cycloalkyl-$(C_{1-4})$alkyl- are each optionally substituted with one to three substituents each independently selected from $(C_{1-3})$alkyl; and
  $R^{2004}$ in each case is independently selected from H and $R^{2003}$;

$R^3$ is selected from:
  (i) —C(O)OR$^{31}$ wherein R$^{31}$ is $(C_{1-6})$alkyl or aryl, wherein the $(C_{1-6})$alkyl is optionally substituted with one to three halogen substituents;
  (ii) —C(O)NR$^{32}$R$^{33}$, wherein R$^{32}$ and R$^{33}$ are each independently selected from H, $(C_{1-6})$alkyl, and Het;
  (iii) —SO$_v$R$^{34}$ wherein v is 1 or 2 and R$^{34}$ is selected from: $(C_{1-6})$alkyl, aryl, Het, and NR$^{32}$R$^{33}$ wherein R$^{32}$ and R$^{33}$ are as defined above; and
  (iv) —C(O)—R$^{35}$, wherein R$^{35}$ is selected from $(C_{1-8})$alkyl, $(C_{3-7})$cycloalkyl, $(C_{3-7})$cycloalkyl-$(C_{1-4})$alkyl-, aryl, aryl-$(C_{1-6})$alkyl-, Het and Het-$(C_{1-6})$alkyl, each of which are optionally substituted with one or more substituents each independently selected from halo, $(C_{1-6})$alkyl, $(C_{3-7})$cycloalkyl, aryl, Het, hydroxyl, —O—$(C_{1-6})$alkyl, —S—$(C_{1-6})$alkyl, —SO—$(C_{1-6})$alkyl, —SO$_2$—$(C_{1-6})$alkyl, —O-aryl, —S-aryl, —SO-aryl and —SO$_2$-aryl, wherein the aryl portion of the —O-aryl, —S-aryl, —SO-aryl and —SO$_2$-aryl are each optionally substituted with one to five halo substituents;

$R^4$ is $(C_{1-6})$alkyl, $(C_{2-6})$alkenyl, $(C_{3-7})$cycloalkyl, $(C_{3-7})$cycloalkyl-$(C_{1-6})$alkyl-, aryl, Het, aryl-$(C_{1-4})$alkyl-, or Het-$(C_{1-4})$alkyl-;
  a) the $(C_{1-6})$alkyl, $(C_{2-6})$alkenyl, aryl, Het, $(C_{3-7})$cycloalkyl-$(C_{1-6})$alkyl-, aryl-$(C_{1-4})$alkyl-, and Het-$(C_{1-4})$alkyl- optionally being substituted with one, two or three substituents each independently selected from halogen, nitro, hydroxy, cyano, $(C_{1-6})$alkyl, O—$(C_{1-6})$alkyl, O-aryl, —CO—NH$_2$, —CO—NH$(C_{1-4})$alkyl, —CO—N$((C_{1-4})$alkyl$)_2$, —NH$_2$, —NH$(C_{1-4})$alkyl and —N$((C_{1-4})$alkyl$)_2$, wherein the $(C_{1-6})$alkyl and O—$(C_{1-6})$alkyl are optionally substituted with one to three halogen substituents; and
  b) the $(C_{3-7})$cycloalkyl being optionally substituted with one or more substituents each independently selected from nitro, halogen, hydroxy, cyano, —O—$(C_{1-6})$alkyl, $(C_{2-4})$alkenyl, —OCF$_3$, —NH$_2$, —NH$(C_{1-4})$alkyl, —N$((C_{1-4})$alkyl$)_2$, tri$(C_{1-6})$alkylsilyl, R$^{41}$, —C(=O)—R$^{41}$, —C(=O)OR$^{41}$, —C(=O)N(R$^{42}$)R$^{41}$, —SO$_2$R$^{41}$, and —OC(=O)—R$^{41}$; wherein R$^{41}$ in each case is independently selected from:
    i) H, $(C_{3-7})$cycloalkyl, $(C_{4-7})$cycloalkenyl, Het, or aryl-$(C_{1-4})$alkyl-O—;
    ii) aryl or aryloxy, each of which being optionally substituted with $(C_{1-6})$alkyl; and
    iii) $(C_{1-8})$alkyl optionally substituted with one or more substituents each independently selected from —O—$(C_{1-6})$alkyl, hydroxy, halogen, $(C_{2-10})$alkenyl, $(C_{2-10})$alkynyl, $(C_{3-7})$cycloalkyl, $(C_{4-7})$cycloalkenyl, aryl, Het, aryloxy, and aryl-$(C_{1-4})$alkyl-O—, wherein each of the aryl and aryloxy is optionally substituted with $(C_{1-6})$alkyl; and
  $R^{42}$ is selected from H and $(C_{1-6})$alkyl; or
$R^4$ is —N(R$^{N2}$)(R$^{N1}$), wherein R$^{N1}$ and R$^{N2}$ are each independently selected from H, $(C_{1-6})$alkyl, —O—$(C_{1-6})$alkyl, $(C_{3-7})$cycloalkyl, $(C_{3-7})$cycloalkyl-$(C_{1-6})$alkyl-, aryl and aryl-$(C_{1-6})$alkyl-; wherein the $(C_{1-6})$alkyl, —O—$(C_{1-6})$alkyl, $(C_{3-7})$cycloalkyl, $(C_{3-7})$cycloalkyl-$(C_{1-6})$alkyl-, aryl and aryl-$(C_{1-6})$alkyl- are each optionally substituted with one or more substituents each independently selected from halogen, $(C_{1-6})$alkyl, hydroxy, cyano, O—$(C_{1-6})$alkyl, —NH$_2$, —NH$(C_{1-4})$alkyl, —N$((C_{1-4})$alkyl$)_2$, —CO—NH$_2$, —CO—NH$(C_{1-4})$alkyl, —CO—N$((C_{1-4})$alkyl$)_2$, —COOH, and —COO$(C_{1-6})$alkyl; or $R^{N2}$ and $R^{N1}$ are linked, together with the nitrogen to which they are bonded, to form a 3- to 7-membered monocyclic saturated or unsaturated heterocycle optionally fused to at least one other cycle to form a heteropolycycle, the heterocycle and heteropolycycle each optionally containing from one to three further heteroatoms each independently selected from N, S and O and being optionally substituted with one or more substituents each independently selected from halogen, $(C_{1-6})$alkyl, hydroxy, cyano, O—$(C_{1-6})$alkyl, —$NH_2$, —$NH(C_{1-4})$alkyl, —$N((C_{1-4})$alkyl$)_2$, —$CO$—$NH_2$, —$CO$—$NH(C_{1-4})$alkyl, —$CO$—$N((C_{1-4})$alkyl$)_2$, —$COOH$, and —$COO(C_{1-6})$alkyl;

wherein Het as used herein is defined as a 3- to 7-membered heterocycle having 1 to 4 heteroatoms each independently selected from O, N and S, which may be saturated, unsaturated or aromatic, and which is optionally fused to at least one other cycle to form a 4- to 14-membered heteropolycycle having wherever possible 1 to 5 heteroatoms, each independently selected from 0 N and S, the heteropolycycle being saturated, unsaturated or aromatic;

with the proviso that when n is 1; m is 2; $R^1$ is ethyl or ethenyl; and $R^2$ is —O—$R^{20}$, wherein $R^{20}$ is Het, wherein the Het is selected from:

and wherein the Het is optionally substituted with $R^{200}$, wherein $R^{200}$ is one or two substituents each independently selected from methyl, methoxy, chloro, fluoro, hydroxy, phenyl, 4-methoxyphenyl, 4-(dimethylamino)phenyl, 4-cyanophenyl, and a group selected from:

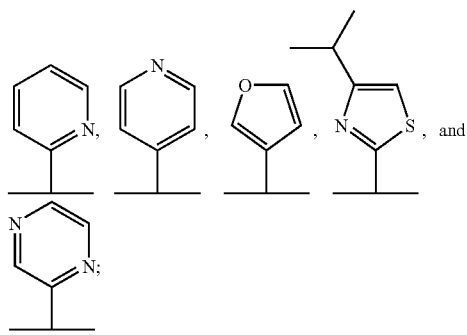

and $R^4$ is cyclopropyl optionally substituted with propyl, cyclopropylmethyl or phenylmethyl; and $R^3$ is —$COOR^{31}$;

then $R^{31}$ is not 1,1-dimethylethyl;

or a racemate, diastereoisomer, or optical isomer thereof, including a salt thereof.

One aspect of the invention provides a pharmaceutical composition comprising an anti-hepatitis C virally effective amount of a compound of formula I, or a pharmaceutically acceptable salt thereof; and a pharmaceutically acceptable carrier medium or auxiliary agent.

According to an embodiment of this aspect, the pharmaceutical composition according to this invention additionally comprises a therapeutically effective amount of at least one other antiviral agent.

Another important aspect of the invention involves a method of treating or preventing a hepatitis C viral infection in a mammal by administering to the mammal an anti-hepatitis C virally effective amount of a compound of formula (I), a pharmaceutically acceptable salt thereof, or a composition as described above, alone or in combination with at least one other antiviral agent, administered together or separately.

Also within the scope of this invention is the use of a compound of formula (I) as described herein, or a pharmaceutically acceptable salt thereof, for the treatment or prevention of hepatitis C viral infection in a mammal.

Further encompassed within the scope of this invention is the use of a compound of formula (I) as described herein, or a pharmaceutically acceptable salt thereof, for the manufacture of a medicament for the treatment or prevention of hepatitis C viral infection in a mammal.

A further aspect of the invention provides the use of a compound of formula (I), as described herein, or a pharmaceutically acceptable salt thereof, in combination with at least one other antiviral agent, for the manufacture of a medicament for the treatment or prevention of hepatitis C viral infection.

Still another aspect of this invention relates to a method of inhibiting the replication of hepatitis C virus by exposing the virus to a hepatitis C viral NS3 protease inhibiting amount of the compound of formula (I) according to this invention, or a pharmaceutically acceptable salt thereof.

Further included in the scope of the invention is the use of a compound of formula (I) according to this invention, or a pharmaceutically acceptable salt thereof, to inhibit the replication of hepatitis C virus.

An additional aspect of this invention refers to an article of manufacture comprising a composition effective to treat an HCV infection or to inhibit the NS3 protease of HCV; and packaging material comprising a label which indicates that the composition can be used to treat infection by the hepatitis C virus; wherein the composition comprises a compound of formula (I) according to this invention or a pharmaceutically acceptable salt thereof.

In a further aspect of this invention is provided a process for the preparation of a compound of formula (I), comprising the steps of:

a) reacting a compound of formula (II):

wherein $R^4$ and m are as defined herein, with a strong base so as to form the corresponding amide anion and b) reacting an azalactone of formula (III):

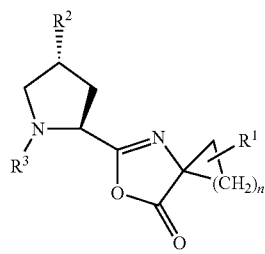

wherein $R^1$, $R^2$, $R^3$, and n are as defined herein, with the amide anion formed in step a).

In yet a further aspect of the present invention is provided an azalactone intermediate compound of formula (III):

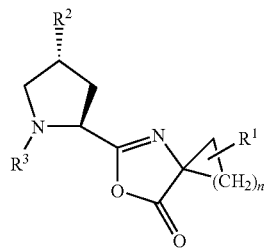

wherein $R^1$, $R^2$, $R^3$ and n are as defined herein.

A further aspect of this invention is the use of the intermediate azalactone of formula (III) as described hereinbefore in the preparation of an HCV NS3 protease inhibitor peptide analog.

Another aspect of this invention is the use of the intermediate azalactone of formula (III) as described hereinbefore in the preparation of an HCV NS3 protease inhibitor of formula (I) as described herein.

DETAILED DESCRIPTION OF PREFERRED EMBODIMENTS

Definitions

As used herein, the following definitions apply unless otherwise noted.

With reference to the instances where (R) or (S) is used to designate the absolute configuration of a substituent or asymmetric center of a compound of formula (I), the designation is done in the context of the whole compound and not in the context of the substituent or asymmetric center alone.

The designations "P2, P1 and P1'" as used herein refer to the position of the amino acid residues starting from the N-terminus of the peptide analogs and extending towards and beyond the cleavage site, i.e. the bond in a substrate of the protease enzyme which is normally cleaved by the catalytic action of the protease enzyme. Thus, P2 refers to position 2 from the C-terminal side of the cleavage site, etc. The bond between the P1 and P1' residues corresponds to the cleavage site. Thus, the P1' position corresponds to the first position on the N-terminal side of the cleavage site (see Berger A. & Schechter I., Transactions of the Royal Society London series B257, 249-264 (1970)). In the context of the compounds of formula (I) herein described, these positions are as designated in the following formula:

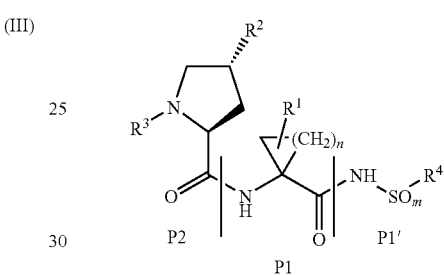

The term "$(C_{1-n})$alkyl" as used herein, wherein n is an integer, either alone or in combination with another substituent, means acyclic, straight or branched chain alkyl substituents containing from 1 to n carbon atoms. "$(C_{1-6})$alkyl" includes, but is not limited to, methyl, ethyl, n-propyl, n-butyl, 1-methylethyl (iso-propyl), 1-methylpropyl, 2-methylpropyl, 1,1-dimethylethyl (tert-butyl), pentyl and hexyl. The abbreviation Me denotes a methyl group and Et denotes an ethyl group.

The term "$(C_{2-n})$alkenyl", as used herein, wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl (vinyl), 1-propenyl, 2-propenyl, and 1-butenyl. Unless specified otherwise, the term "$(C_{2-n})$alkenyl" is understood to encompass individual stereoisomers where possible, including but not limited to (E) and (Z) isomers, and mixtures thereof. When a $(C_{2-n})$ alkenyl group is substituted, it is understood to be substituted on any carbon atom thereof which would otherwise bear a hydrogen atom, unless specified otherwise.

The term "$(C_{2-n})$alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals include, but are not limited to, ethynyl, 1-propynyl, 2-propynyl, and 1-butynyl. When a $(C_{2-n})$alkynyl group is substituted, it is understood to be substituted on any carbon atom thereof which would otherwise bear a hydrogen atom, unless specified otherwise.

The term "$(C_{3-m})$cycloalkyl" as used herein, wherein m is an integer, either alone or in combination with another substituent, means a cycloalkyl substituent containing from 3 to m carbon atoms and includes, but is not limited to, cyclopropyl, cyclobutyl, cyclopentyl, cyclohexyl and cycloheptyl.

The term "($C_{3-m}$)cycloalkyl-($C_{1-n}$)alkyl-" as used herein, wherein n and m are both integers, means an alkyl radical containing from 1 to n carbon atoms to which a cycloalkyl radical containing from 3 to m carbon atoms is directly linked; including, but not limited to, cyclopropylmethyl, cyclobutylmethyl, cyclopentylmethyl, 1-cyclopentylethyl, 2-cyclopentylethyl, cyclohexylmethyl, 1-cyclohexylethyl and 2-cyclohexylethyl. Unless specified otherwise, a ($C_{3-m}$)cycloalkyl-($C_{1-n}$)alkyl- group may be substituted on either the cycloalkyl or the alkyl portion thereof, or both.

The term "aryl" as used herein, either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl.

As used herein, the term "aryl-($C_{1-n}$)alkyl-" means an alkyl radical containing from 1 to n carbon atoms, wherein n is an integer, to which an aryl radical is bonded. Examples of aryl-($C_{1-3}$)alkyl- include, but are not limited to, benzyl (phenylmethyl), 1-phenylethyl, 2-phenylethyl and phenylpropyl. Unless specified otherwise, an aryl-($C_{1-n}$)alkyl- group may be substituted on either the cycloalkyl or the alkyl portion thereof, or both.

As used herein, the term "Het" defines a 3- to 7-membered heterocycle having 1 to 4 heteroatoms each independently selected from O, N and S, which may be saturated, unsaturated or aromatic, and which is optionally fused to at least one other cycle to form a 4- to 14-membered heteropolycycle having wherever possible 1 to 5 heteroatoms, each independently selected from O, N and S, the heteropolycycle being saturated, unsaturated or aromatic, unless specified otherwise.

As used herein the term "heteroatom" means O, S or N.

As used herein, the term "heterocycle", either alone or in combination with another radical, means a monovalent radical derived by removal of a hydrogen from a three- to seven-membered saturated or unsaturated (including aromatic) heterocycle containing from one to four heteroatoms each independently selected from nitrogen, oxygen and sulfur. Examples of such heterocycles include, but are not limited to, azetidine, pyrrolidine, furan, tetrahydrofuran, thiazolidine, pyrrole, thiophene, hydantoin, diazepine, 1H-imidazole, isoxazole, thiazole, tetrazole, piperidine, piperazine, homopiperidine, homopiperazine, pyran, tetrahydropyran, 1,4-dioxane, 4-morpholine, 4-thiomorpholine, pyridine, pyridine-N-oxide or pyrimidine, or the following heterocycles:

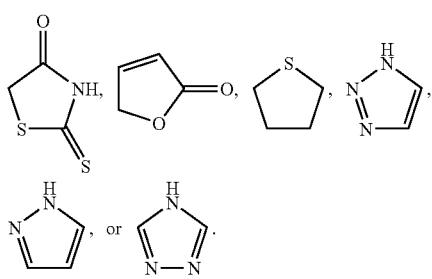

As used herein, the term "heteropolycycle" either alone or in combination with another radical, means a heterocycle as defined above fused to one or more other cycle, be it a heterocycle or any other cycle. Examples of such heteropolycycles include, but are not limited to, indole, benzimidazole, thiazolo[4,5-b]-pyridine, quinoline, isoquinoline, or coumarin, or the following:

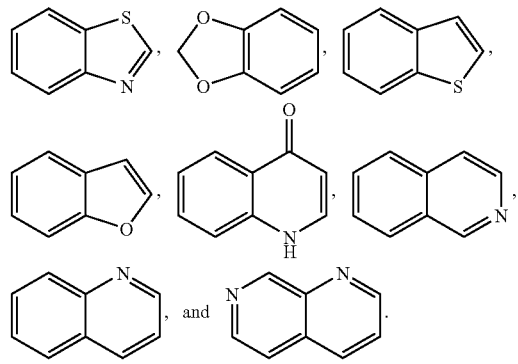

The term "O—($C_{1-n}$)alkyl" or "($C_{1-n}$)alkoxy" as used herein interchangeably, either alone or in combination with another radical, means the radical —O—($C_{1-n}$)alkyl wherein alkyl is as defined above containing from 1 to n carbon atoms, and includes, but is not limited to, methoxy, ethoxy, propoxy, 1-methylethoxy, butoxy and 1,1-dimethylethoxy. The latter radical is known commonly as tert-butoxy. When an O—($C_{1-n}$)alkyl radical is substituted, it is understood to be substituted on the ($C_{1-n}$)alkyl portion thereof.

As used herein, the term "—S—($C_{1-n}$)alkyl" or "($C_{1-n}$)alkylthio", used interchangeably, refers to a sulfur atom further bonded to an alkyl radical as defined above containing from 1 to n carbon atoms. Examples of ($C_{1-6}$)alkylthio include, but are not limited to, methylthio ($CH_3S$—), ethylthio ($CH_3CH_2S$—), propylthio ($CH_3CH_2CH_2S$—), 1-methylethylthio (isopropylthi; $(CH_3)_2CHS$—), 1,1-dimethylethylthio (tert-butylthio; $(CH_3)_3CS$—), etc. When an —S—($C_{1-n}$)alkyl radical is substituted, it is understood to be substituted on the ($C_{1-n}$)alkyl portion thereof.

The term "halo" or "halogen" as used herein interchangeably means a halogen substituent selected from fluoro, chloro, bromo or iodo.

The term "oxo" as used herein means an oxygen atom attached as a substituent by a double bond (=O).

The term "thioxo" as used herein means an sulfur atom attached as a substituent by a double bond (=S).

The term "salt thereof" means any acid and/or base addition salt of a compound according to the invention; preferably a pharmaceutically acceptable salt thereof.

The term "pharmaceutically acceptable salt" means a salt of a compound of formula (I) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, sulfuric acid, sulfamic acid, nitric acid, phosphoric acid, and the like, and organic acids such as acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethane-sulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic non-toxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "mammal" as it is used herein is meant to encompass humans, as well as non-human mammals which are susceptible to infection by hepatitis C virus including domestic animals, such as cows, pigs, horses, dogs and cats, and non-domestic animals.

The term "antiviral agent" as used herein means an agent (compound or biological) that is effective to inhibit the formation and/or replication of a virus in a mammal. This includes agents that interfere with either host or viral mechanisms necessary for the formation and/or replication of a virus in a mammal. Such agents include but are not limited to another anti-HCV agent, an HIV inhibitor, an HAV inhibitor and an HBV inhibitor. Antiviral agents include, for example, ribavirin, amantadine, VX-497 (merimepodib, Vertex Pharmaceuticals), VX-498 (Vertex Pharmaceuticals), Levovirin, Viramidine, Ceplene (maxamine), XTL-001 and XTL-002 (XTL Biopharmaceuticals).

The term "other anti-HCV agent" as used herein means those agents that are effective for diminishing or preventing the progression of hepatitis C related symptoms of disease. Such agents can be selected from: immunomodulatory agents, inhibitors of HCV NS3 protease, inhibitors of HCV polymerase or inhibitors of another target in the HCV life cycle.

The term "immunomodulatory agent" as used herein means those agents (compounds or biologicals) that are effective to enhance or potentiate the immune system response in a mammal. Immunomodulatory agents include, for example, class I interferons (such as α-, β-, δ- and omega interferons, tau-interferons, consensus interferons and asialo-interferons), class II interferons (such as γ-interferons), pegylated interferons and conjugated interferons, including but not limited to interferons conjugated with other proteins including but not limited to human albumin.

The term "inhibitor of HCV NS3 protease" as used herein means an agent (compound or biological) that is effective to inhibit the function of HCV NS3 protease in a mammal. Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/037855, WO 2004/101602, WO 2004/101605, WO 2004/103996 and co-pending patent application Ser. Nos. 10/945,518, 11/039,698; herein incorporated by reference in their entirety (all by Boehringer Ingelheim), WO 02/060926, WO 03/053349, WO 03/099274, WO 03/099316, WO 2004/032827, WO 2004/043339, WO 2004/094452 (all by BMS), WO 2004/072243, WO 2004/093798, WO 2004/113365, WO 2005/010029 (all by Enanta) and WO 2005/037214 (Intermune), and the Vertex candidate identified as VX-950.

The term "inhibitor of HCV polymerase" as used herein means an agent (compound or biological) that is effective to inhibit the function of an HCV polymerase in a mammal. This includes, but is not limited to, non-nucleoside and nucleoside inhibitors of HCV NS5B polymerase.

Examples of inhibitors of HCV polymerase include but are not limited to those compounds described in: WO 02/04425 (Boehringer Ingelheim) WO 03/007945 (Boehringer Ingelheim), WO 03/010140 (Boehringer Ingelheim), WO 03/010141 (Boehringer Ingelheim), WO 2004/064925 (Boehringer Ingelheim), WO 2004/065367 (Boehringer Ingelheim), WO 2005/012288 (Genelabs), WO 2004/087714 (IRBM), WO 03/101993 (Neogenesis), WO 03/026587 (BMS), WO 03/000254 (Japan Tobacco), and WO 01/47883 (Japan Tobacco), and the clinical candidates JTK-003 (Japan Tobacco), HCV 086 (ViroPharma/Wyeth), R-803 (Rigel) and NM 283 (Idenix/Novartis).

The term "inhibitor of another target in the HCV life cycle" as used herein means an agent (compound or biological) that is effective to inhibit the formation and/or replication of HCV in a mammal other than by inhibiting the function of the HCV NS3 protease. This includes agents that interfere with either host or HCV viral mechanisms necessary for the formation and/or replication of HCV in a mammal. Inhibitors of another target in the HCV life cycle include, for example, agents that inhibit a target selected from a helicase, a NS2/3 protease and an internal ribosome entry site (IRES) and agents that interfere with the function of other viral targets including but not limited to an NS5A protein.

The term "HIV inhibitor" as used herein means an agents (compound or biological) that is effective to inhibit the formation and/or replication of HIV in a mammal. This includes agents that interfere with either host or viral mechanisms necessary for the formation and/or replication of HIV in a mammal. HIV inhibitors include, for example, nucleoside inhibitors, non-nucleoside inhibitors, protease inhibitors, fusion inhibitors and integrase inhibitors.

The term "HAV inhibitor" as used herein means an agent (compound or biological) that is effective to inhibit the formation and/or replication of HAV in a mammal. This includes agents that interfere with either host or viral mechanisms necessary for the formation and/or replication of HAV in a mammal. HAV inhibitors include Hepatitis A vaccines, for example, Havrix® (GlaxoSmithKline), VAQTA® (Merck) and Avaxim® (Aventis Pasteur).

The term "HBV inhibitor" as used herein means an agent (compound or biological) that is effective to inhibit the formation and/or replication of HBV in a mammal. This includes agents that interfere with either host or viral mechanisms necessary for the formation and/or replication of HBV in a mammal. HBV inhibitors include, for example, agents that inhibit HBV viral DNA polymerase or HBV vaccines. Specific examples of HBV inhibitors include Lamivudine (Epivir-HBV®), Adefovir Dipivoxil, Entecavir, FTC (Coviracil®), DAPD (DXG), L-FMAU (Clevudine®), AM365 (Amrad), Ldt (Telbivudine), monoval-LdC (Valtorcitabine), ACH-126,443 (L-Fd4C) (Achillion), MCC478 (Eli Lilly), Racivir (RCV), Fluoro-L and D nucleosides, Robustaflavone, ICN 2001-3 (ICN), Bam 205 (Novelos), XTL-001 (XTL), Imino-Sugars (Nonyl-DNJ) (Synergy), HepBzyme; and immunomodulator products such as: interferon alpha 2b, HE2000 (Hollis-Eden), Theradigm (Epimmune), EHT899 (Enzo Biochem), Thymosin alpha-1 (Zadaxin®), HBV DNA vaccine (PowderJect), HBV DNA vaccine (Jefferon Center), HBV antigen (OraGen), BayHep B® (Bayer), Nabi-HB® (Nabi) and Anti-hepatitis B (Cangene); and HBV vaccine products such as the following: Engerix B, Recombivax HB, GenHevac B, Hepacare, Bio-Hep B, TwinRix, Comvax, Hexavac.

The term "class I interferon" as used herein means an interferon selected from a group of interferons that all bind to receptor type I. This includes both naturally and synthetically produced class I interferons. Examples of class I interferons include α-, β-, δ-, ω-interferons, τ-interferons, consensus interferons, asialo-interferons and pegylated forms thereof.

The term "class II interferon" as used herein means an interferon selected from a group of interferons that all bind to receptor type II. Examples of class II interferons include γ-interferons.

Specific preferred examples of some of these agents are listed below:

antiviral agents: ribavirin and amantadine;
immunomodulatory agents: class I interferons, class II interferons, pegylated interferons and conjugated interferons;
HCV polymerase inhibitors: nucleoside analogs and non-nucleosides;
inhibitor of another target in the HCV life cycle: agents that inhibit a target selected from a helicase, a NS2/3 protease and an internal ribosome entry site (IRES) and agents that interfere with the function of other viral targets including but not limited to an NS5A protein;
HIV inhibitors: nucleoside inhibitors, non-nucleoside inhibitors, protease inhibitors, fusion inhibitors and integrase inhibitors; or
HBV inhibitors: agents that inhibit viral DNA polymerase or is an HBV vaccine.

As discussed above, combination therapy is contemplated wherein a compound of formula (I), or a pharmaceutically acceptable salt thereof, is co-administered with at least one additional agent selected from: an antiviral agent, an immunomodulatory agent, another inhibitor of HCV NS3 protease, an inhibitor of HCV polymerase, an inhibitor of another target in the HCV life cycle, an HIV inhibitor, an HAV inhibitor and an HBV inhibitor. Examples of such agents are provided in the Definitions section above. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of wherein a compound of formula (I), or a pharmaceutically acceptable salt thereof.

As used herein, the term "treatment" means the administration of a compound or composition according to the present invention to alleviate or eliminate symptoms of the hepatitis C disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood.

As used herein, the symbol ⁓ used to represent a bond to or from a stereogenic centre means that the stereochemistry at that centre is mixed. For example, when the stereogenic centre is a chiral centre, the symbol ⁓ means that the stereochemistry at that centre is a mixture of (R) and (S). As an alternative example, when the stereogenic centre gives rise to geometric isomerism, the symbol ⁓ means that the stereochemistry at that centre is a mixture of (E) and (Z).

As used herein, the designation whereby a bond to a substituent R is drawn as emanating from the center of a ring, such as, for example,

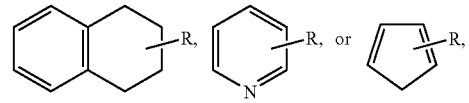

means that the substituent R may be attached to any free position on the ring that would otherwise be substituted with a hydrogen atom, unless specified otherwise. The following sign ┬ is used in sub-formulas to indicate the bond which is connected to the rest of the molecule as defined.

Preferred Embodiments

In the following preferred embodiments, groups and substituents of the compounds of formula (I) according to this invention are described in detail. Groups, substituents and indices are defined as hereinbefore unless stated otherwise.

m:
Preferred compounds of formula (I) of the present invention are those wherein m is 2.
Alternatively, preferred compounds of formula (I) are those wherein m is 1.
Any and each individual definition of m as set out herein may be combined with any and each individual definition of $R^1$, $R^2$, $R^3$, $R^4$, and n as set out herein.

n:
Preferred compounds of formula (I) are those wherein n is 1.

Any and each individual definition of n as set out herein may be combined with any and each individual definition of $R^1$, $R^2$, $R^3$, $R^4$, and m as set out herein.

$R^1$:

Preferably, $R^1$ is $(C_{2-6})$alkenyl or $(C_{2-6})$alkyl.

More preferably, $R^1$ is ethyl or ethenyl.

Any and each individual definition of $R^1$ as set out herein may be combined with any and each individual definition of $R^2$, $R^3$, $R^4$, n, and m as set out herein.

In the moiety P1, the substituent $R^1$ and the carbonyl preferably take a syn orientation. Therefore, in the case $R^1$ is ethyl, the asymmetric carbon atoms in the cyclopropyl group take the R,R configuration according to the subformula:

In the case $R^1$ is ethenyl, the asymmetric carbon atoms in the cyclopropyl group preferably take the R,S configuration according to the subformula:

Therefore, in a preferred embodiment, the compounds of the present invention have the formula (Ia):

(Ia)

(I)

In another preferred embodiment of the present invention, m is 2, n is 1, and $R^1$ is ethyl or ethenyl, wherein $R^2$, $R^3$ and $R^4$ are as defined hereinbefore and hereinafter.

$R^2$:

Preferably, $R^2$ is selected from —O—$R^{20}$ and —S—$R^{20}$, wherein $R^{20}$ is as defined herein.

More preferably, $R^2$ is —O—$R^{20}$, and $R^{20}$ is aryl or Het, wherein the aryl and Het are optionally substituted with $R^{200}$, wherein $R^{200}$ is as defined herein.

Even more preferably, $R^2$ is —O—$R^{20}$, wherein $R^{20}$ is Het, wherein the Het is optionally substituted with $R^{200}$ wherein $R^{200}$ is as defined herein.

Still more preferably, when $R^2$ is —O—$R^{20}$ and $R^{20}$ is Het, Het preferably is a heterocycle or heteropolycycle, each of which containing at least one nitrogen heteroatom, and the Het is unsubstituted or substituted with $R^{200}$, wherein $R^{200}$ is as defined herein.

Yet more preferably, when $R^2$ is —O—$R^{20}$ and $R^{20}$ is Het, Het is preferably selected from wherein the Het is unsubstituted or substituted with $R^{200}$ wherein $R^{200}$ is as defined herein.

Preferably, $R^2$ is —O—$R^{20}$ and $R^{20}$ is Het selected from wherein the Het is unsubstituted or substituted with $R^{200}$
  wherein $R^{200}$ is one to four substituents each independently selected from H, halogen, cyano, $(C_{1-6})$alkyl, aryl, Het, —O$R^{201}$, —S$R^{201}$ —SO$R^{201}$ and —SO$_2R^{201}$;
  wherein $(C_{1-6})$alkyl, aryl and Het are each optionally further substituted with $R^{2000}$;
  $R^{201}$ is in each case independently selected from $(C_{1-6})$alkyl optionally further substituted with $R^{2000}$;
  $R^{2000}$ is in each case independently one to three substituents each independently selected from halogen, $R^{2003}$, aryl, Het, —O$R^{2001}$; —S$R^{2001}$, —SO$R^{2001}$, SO$_2R^{2001}$, cyano, and —N($R^{2002}$)($R^{2001}$); wherein the aryl and Het are each optionally substituted with one, two or three substituents each independently selected from $(C_{1-6})$alkyl and —O—$(C_{1-6})$alkyl;
  $R^{2001}$ is in each case independently selected from aryl, aryl-$(C_{1-6})$alkyl-, —C(O)—$R^{2003}$, —C(O)O—$R^{2003}$— CON($R^{2002}$)($R^{2004}$) and $R^{2004}$;
  $R^{2002}$ is in each case independently selected from H and $(C_{1-6})$alkyl;
  $R^{2003}$ is in each case independently selected from $(C_{1-8})$alkyl, $(C_{3-7})$cycloalkyl and $(C_{3-7})$cycloalkyl-$(C_{1-4})$alkyl-, wherein the $(C_{3-7})$cycloalkyl and $(C_{3-7})$cycloalkyl-$(C_{1-4})$alkyl- are each optionally substituted with one to three substituents each independently selected from $(C_{1-3})$alkyl;
  $R^{2004}$ is in each case independently selected from H and $R^{2003}$; and
  Het is in each case independently a 5- 6- or 7-membered monocyclic saturated, unsaturated or aromatic heterocycle containing 1 to 4 heteroatoms each independently selected from N, O and S.

Also preferred are compounds of formula (I) wherein $R^2$ is —O—$R^{20}$ and $R^{20}$ is Het of the formula

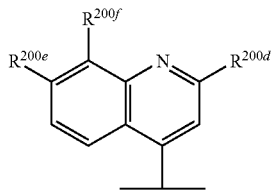

wherein
$R^{200d}$ is H, aryl, Het, or —$OR^{201}$, wherein Het is a 5- 6- or 7-membered monocyclic saturated, unsaturated or aromatic heterocycle containing 1 to 4 heteroatoms each independently selected from N, O and S and wherein the aryl and Het are each optionally further substituted with $R^{2000}$;
$R^{200e}$ is H or —$OR^{201}$; and
$R^{200f}$ is H, $(C_{1-6})$alkyl, halogen, —$SR^{201}$, —$SO_2R^{201}$, or —$OR^{201}$; wherein the $(C_{1-6})$alkyl is optionally further substituted with $R^{2000}$; wherein
$R^{201}$ is in each case independently selected from $(C_{1-6})$alkyl optionally further substituted with $R^{2000}$;
$R^{2000}$ is in each case independently one to three substituents each independently selected from halogen, $(C_{3-7})$cycloalkyl, aryl, —$OR^{2001}$ cyano, and —$N(R^{2002})(R^{2001})$;
$R^{2001}$ is in each case independently selected from H, $(C_{1-6})$alkyl and —$COR^{2003}$;
$R^{2002}$ is in each case independently selected from H and $(C_{1-6})$alkyl; and
$R^{2003}$ is in each case independently selected from $(C_{1-8})$alkyl, $(C_{3-7})$cycloalkyl and $(C_{3-7})$cycloalkyl-$(C_{1-4})$alkyl-.

Even more preferred are compounds wherein $R^2$ is —O—$R^{20}$, $R^{20}$ is Het and Het is

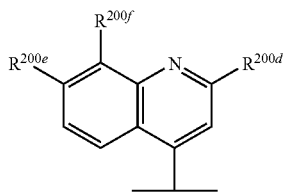

wherein
$R^{200d}$ is —$OR^{201}$ wherein $R^{201}$ is $(C_{1-6})$alkyl;
$R^{200e}$ is H or —$OR^{201}$ wherein $R^{201}$ is $(C_{1-6})$alkyl; and
$R^{200f}$ is $(C_{1-6})$alkyl, halogen, —$OR^{201}$ or —$SR^{201}$, wherein $R^{201}$ is $(C_{1-6})$alkyl.

Most preferably, $R^2$ is selected from:

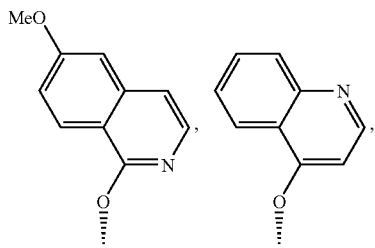

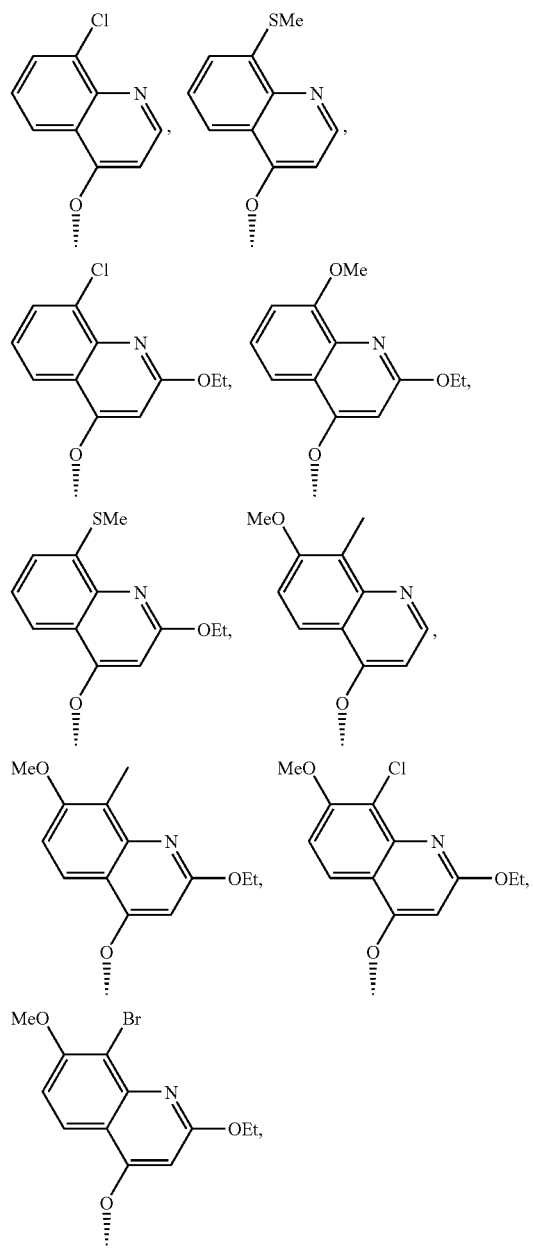

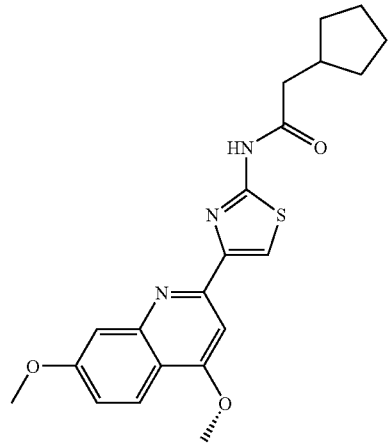

and

-continued

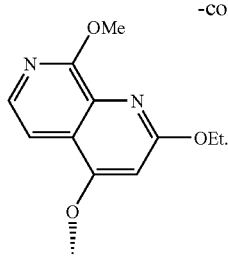

Any and each individual definition of $R^2$ as set out herein may be combined with any and each individual definition of $R^1$, $R^3$, $R^4$, n and m as set out herein.

$R^4$:

In a preferred embodiment of the present invention, $R^4$ is selected from methyl, ethyl, propyl, 1-methylethyl, butyl, 1-methylpropyl, 2-methylpropyl, 1,1-dimethylethyl, ethenyl, 1-propenyl, 2-propenyl, cyclopropylmethyl, cyclobutylmethyl, cyclopentylmethyl, cyclohexylmethyl, phenyl, naphthyl, Het, phenylmethyl, naphthylmethyl and Het-methyl;

a) each of which optionally being substituted with one to three substituents each independently selected from fluoro and methyl; and
b) each of which optionally being substituted with one or two substituents each independently selected from hydroxy, trifluoromethyl, methoxy, phenoxy and trifluoromethoxy; and
c) each of which optionally being substituted with a substituent selected from chloro, bromo, cyano, nitro, —CO—NH$_2$, —CO—NHCH$_3$, —CO—N(CH$_3$)$_2$, —NH$_2$, —NH(CH$_3$) and —N(CH$_3$)$_2$;

wherein Het is selected from thienyl, furyl, thiazolyl, benzothiazolyl, pyrrolyl, imidazolyl, pyrazolyl, pyridinyl, pyrazinyl, pyrimidinyl, pyridazinyl, indolizinyl, isoindolyl, 3H-indolyl, indolyl, quinolinyl, isoquinolinyl, tetrahydrothienyl, tetrahydrofuryl, thiadiazolyl, isoxazolyl, benzothienyl, piperidinyl, piperazinyl, morpholinyl, triazolyl, tetrazolyl, and

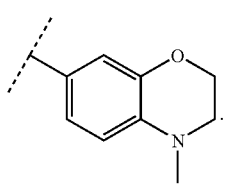

Even more preferably in this embodiment, $R^4$ is phenyl, optionally substituted with halogen.

In an alternative preferred embodiment, $R^4$ is selected from cyclopropyl, cyclobutyl, cyclopentyl or cyclohexyl;
a) each of which optionally being substituted with one, two or three fluoro substituents; and
b) each of which optionally being substituted with one or two substituents each independently selected from hydroxy, trifluoromethyl, methoxy and trifluoromethoxy; and
c) each of which optionally being substituted with a substituent selected from chloro, bromo, cyano, nitro, —CO—NH$_2$, —CO—NHCH$_3$, —CO—N(CH$_3$)$_2$, —NH$_2$, —NH(CH$_3$) and —N(CH$_3$)$_2$; and
d) each of which being optionally substituted with (C$_{1-8}$)alkyl, wherein the (C$_{1-8}$)alkyl is optionally substituted with one or more substituents each independently selected from —O—(C$_{1-6}$)alkyl, hydroxy, halogen, (C$_{2-10}$)alkenyl, (C$_{2-10}$)alkynyl, (C$_{3-7}$)cycloalkyl, (C$_{4-7}$)cycloalkenyl, aryl, aryloxy, and aryl-(C$_{1-4}$)alkyl-O—, wherein each of the aryl and aryloxy is optionally substituted with (C$_{1-6}$)alkyl.

More preferably, the group $R^4$ is selected from methyl, ethyl, 1-methylethyl, propyl, ethenyl, cyclopropyl, cyclobutyl, cyclopentyl, Het and phenyl; wherein Het is selected from

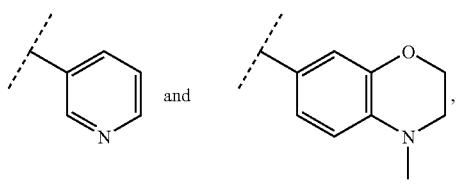

the Het being optionally substituted with phenoxy; and wherein the phenyl is optionally substituted with halogen; and wherein the cyclopropyl is optionally substituted at the 1-position with methyl, ethyl, propyl or butyl, each of the methyl, ethyl, propyl and butyl being optionally further substituted with phenyl, (C$_{3-6}$)cycloalkyl, (C$_{2-6}$)alkenyl or (C$_{1-4}$)alkoxy.

Even more preferably, $R^4$ is cyclopropyl, 1-methylcyclopropyl, 1-ethylcyclopropyl, 1-benzylcyclopropyl,

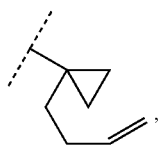

phenyl, 3-chlorophenyl, 4-chlorophenyl,

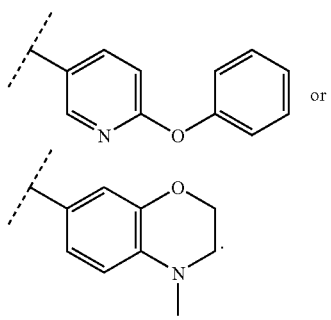

Most preferably, $R^4$ is cyclopropyl or 1-methylcyclopropyl.

In another alternative preferred embodiment, $R^4$ is —N(R$^{N2}$)(R$^{N1}$), wherein R$^{N1}$ and R$^{N2}$ are each independently selected from H, methyl, ethyl, propyl, 1-methylethyl, methoxy, ethoxy, propoxy, 1-methylethoxy, cyclopropyl, cyclobutyl, cyclopentyl, cyclohexyl, phenyl and phenylmethyl; wherein the methyl, ethyl, propyl, 1-methylethyl, methoxy, ethoxy, propoxy, 1-methylethoxy, cyclopropyl, cyclobutyl, cyclopentyl, cyclohexyl, phenyl and phenylmethyl are optionally substituted with one or more substituents each independently selected from halogen, (C$_{1-4}$)alkyl, hydroxy, cyano, O—(C$_{1-4}$)alkyl, —NH$_2$, —NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-4}$)alkyl; or R$^{N2}$ and R$^{N1}$ are linked, together with the nitrogen to which they are bonded, to form a 3- 4-, 5- or 6-membered monocyclic saturated or unsaturated heterocycle, optionally containing from one to three further heteroatoms each independently selected from N, S and O and optionally substituted with one, two or three substituents each independently selected from halogen, (C$_{1-4}$)alkyl, hydroxy, cyano, O—(C$_{1-4}$)alkyl, —NH$_2$, —NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-4}$)alkyl.

In another alternative preferred embodiment, R$^4$ is —N(R$^{N2}$)(R$^{N1}$), wherein R$^{N1}$ and R$^{N2}$ are each independently selected from methyl, ethyl, propyl, 1-methylethyl, methoxy, ethoxy, propoxy, 1-methylethoxy, cyclopropyl, cyclobutyl, cyclopentyl, cyclohexyl, phenyl and phenylmethyl; wherein the methyl, ethyl, propyl, 1-methylethyl, methoxy, ethoxy, propoxy, 1-methylethoxy, cyclopropyl, cyclobutyl, cyclopentyl, cyclohexyl, phenyl and phenylmethyl are optionally substituted with one or more substituents each independently selected from halogen, (C$_{1-4}$)alkyl, hydroxy, cyano, O—(C$_{1-4}$)alkyl, —NH$_2$, —NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-4}$)alkyl; or R$^{N2}$ and R$^{N1}$ are linked, together with the nitrogen to which they are bonded, to form a 3- 4-, 5- or 6-membered monocyclic saturated or unsaturated heterocycle, optionally containing from one to three further heteroatoms each independently selected from N, S and O and optionally substituted with one, two or three substituents each independently selected from halogen, (C$_{1-4}$)alkyl, hydroxy, cyano, O—(C$_{1-4}$)alkyl, —NH$_2$, —NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-4}$)alkyl.

More preferably in this embodiment, R$^4$ is selected from . . .

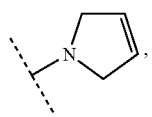

—N(CH$_3$)—OCH$_3$ and —N(CH$_3$)$_2$.

Most preferably, R$^4$ is —N(CH$_3$)$_2$.

Therefore preferably, R$^4$ is selected from methyl, ethyl, propyl, 1-methylethyl, butyl, 1-methylpropyl, 2-methylpropyl, 1,1-dimethylethyl, ethenyl, 1-propenyl, 2-propenyl, cyclopropylmethyl, cyclobutylmethyl, cyclopentylmethyl, cyclohexylmethyl, phenyl, naphthyl, Het, phenylmethyl, naphthylmethyl and Het-methyl;
a) each of which optionally being substituted with one, two or three substituents each independently selected from fluoro and methyl; and
b) each of which optionally being substituted with one or two substituents each independently selected from hydroxy, trifluoromethyl, methoxy, phenoxy and trifluoromethoxy; and
c) each of which optionally being substituted with a substituent selected from chloro, bromo, CF$_3$, cyano, nitro, —CO—NH$_2$, —CO—NHCH$_3$, —CO—N(CH$_3$)$_2$, —NH$_2$, —NH(CH$_3$) and —N(CH$_3$)$_2$;

wherein Het is selected from thienyl, furyl, thiazolyl, benzothiazolyl, pyrrolyl, imidazolyl, pyrazolyl, pyridinyl, pyrazinyl, pyrimidinyl, pyridazinyl, indolizinyl, isoindolyl, 3H-indolyl, indolyl, quinolinyl, isoquinolinyl, tetrahydrothienyl, tetrahydrofuryl, thiadiazolyl, isoxazolyl, benzothienyl, piperidinyl, piperazinyl, morpholinyl, triazolyl, tetrazolyl, and

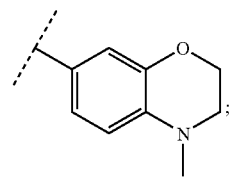

or R$^4$ is selected from cyclopropyl, cyclobutyl, cyclopentyl or cyclohexyl;
a) each of which optionally being substituted with one, two or three fluoro substituents; and
b) each of which optionally being substituted with one or two substituents selected from hydroxy, trifluoromethyl, methoxy and trifluoromethoxy; and
c) each of which optionally being substituted with a substituent selected from chloro, bromo, cyano, nitro, —CO—NH$_2$, —CO—NHCH$_3$, —CO—N(CH$_3$)$_2$, —NH$_2$, —NH(CH$_3$) and —N(CH$_3$)$_2$; and
d) each of which being optionally substituted with (C$_{1-8}$)alkyl, wherein the (C$_{1-8}$)alkyl is optionally substituted with one or more substituents each independently selected from —O—(C$_{1-6}$)alkyl, hydroxy, halogen, (C$_{2-10}$)alkenyl, (C$_{2-10}$)alkynyl, (C$_{3-7}$)cycloalkyl, (C$_{4-7}$)cycloalkenyl, aryl, aryloxy, and aryl-(C$_{1-4}$)alkyl-O—, wherein each of the aryl and aryloxy is optionally substituted with (C$_{1-6}$)alkyl;

or R$^4$ is —N(R$^{N2}$)(R$^{N1}$), wherein R$^{N1}$ and R$^{N2}$ are each independently selected from H, methyl, ethyl, propyl, 1-methylethyl, methoxy, ethoxy, propoxy, 1-methylethoxy, cyclopropyl, cyclobutyl, cyclopentyl, cyclohexyl, phenyl and phenylmethyl; wherein the methyl, ethyl, propyl, 1-methylethyl, methoxy, ethoxy, propoxy, 1-methylethoxy, cyclopropyl, cyclobutyl, cyclopentyl, cyclohexyl, phenyl and phenylmethyl are optionally substituted with one or more substituents each independently selected from halogen, (C$_{1-4}$)alkyl, hydroxy, cyano, O—(C$_{1-4}$)alkyl, —NH$_2$, —NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-4}$)alkyl; or R$^{N2}$ and R$^{N1}$ are linked, together with the nitrogen to which they are bonded, to form a 3- 4-, 5- or 6-membered monocyclic saturated or unsaturated heterocycle, optionally containing from one to three further heteroatoms each independently selected from N, S and O and optionally substituted with one, two or three substituents each independently selected from halogen, (C$_{1-4}$)alkyl, hydroxy, cyano, O—(C$_{1-4}$)alkyl, —NH$_2$, —NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-4}$)alkyl.

More preferably, R$^4$ is selected from methyl, ethyl, 1-methylethyl, propyl, ethenyl, cyclopropyl, cyclobutyl, cyclopentyl, Het, phenyl,

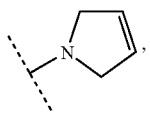

—N(CH₃)—OCH₃ and —N(CH₃)₂; wherein Het is selected from

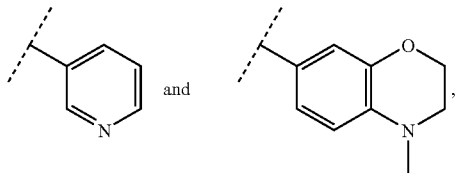

the Het being optionally substituted with phenoxy; and wherein the phenyl is optionally substituted with halogen; and wherein the cyclopropyl is optionally substituted at the 1-position with methyl, ethyl, propyl or butyl, each of the methyl, ethyl, propyl and butyl being optionally further substituted with phenyl, $(C_{3-6})$cycloalkyl, $(C_{2-6})$alkenyl or $(C_{1-4})$alkoxy.

Even more preferably, $R^4$ is cyclopropyl, 1-methylcyclopropyl, 1-ethylcyclopropyl, 1-benzylcyclopropyl,

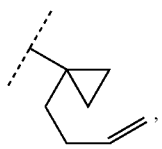

phenyl, 3-chlorophenyl, 4-chlorophenyl,

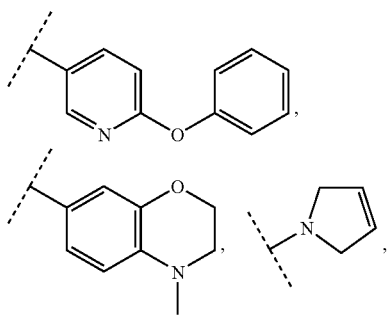

—N(CH₃)—OCH₃ or —N(CH₃)₂.

Most preferably, $R^4$ is cyclopropyl, 1-methylcyclopropyl or —N(CH₃)₂.

Any and each individual definition of $R^4$ as set out herein may be combined with any and each individual definition of $R^1$, $R^2$, $R^3$, n and m as set out herein.

$R^3$:

In a preferred embodiment of the present invention, $R^3$ is —C(O)OR³¹, wherein $R^{31}$ is as defined herein;

with the proviso that when n is 1; m is 2; $R^1$ is ethyl or ethenyl; and $R^2$ is —O—$R^{20}$, wherein $R^{20}$ is Het, wherein the Het is selected from:

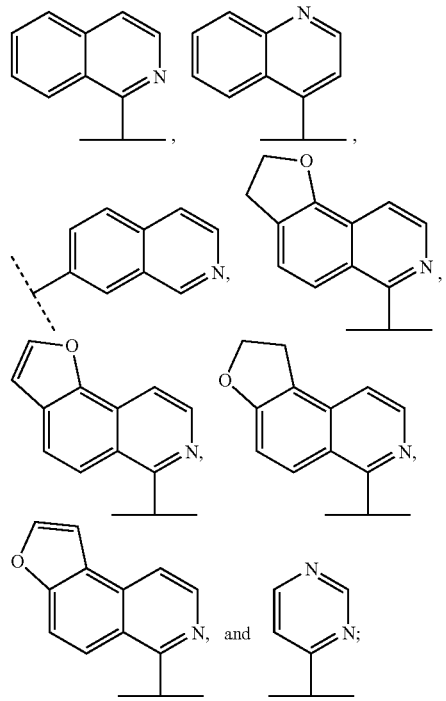

and wherein the Het is optionally substituted with $R^{200}$, wherein $R^{200}$ is one or two substituents each independently selected from methyl, methoxy, chloro, fluoro, hydroxy, phenyl, 4-methoxyphenyl, 4-(dimethylamino)phenyl, 4-cyanophenyl, and a group selected from:

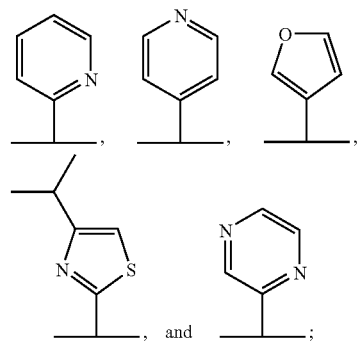

and $R^4$ is cyclopropyl optionally substituted with propyl, cyclopropylmethyl or phenylmethyl;

then $R^{31}$ is not 1,1-dimethylethyl.

Preferably, when $R^3$ is —C(O)OR³¹, $R^{31}$ is $(C_{1-6})$alkyl optionally substituted with one to three halogen substituents;

with the proviso that when n is 1; m is 2; $R^1$ is ethyl or ethenyl; and $R^2$ is —O—$R^{20}$, wherein $R^{20}$ is Het, wherein the Het is selected from:

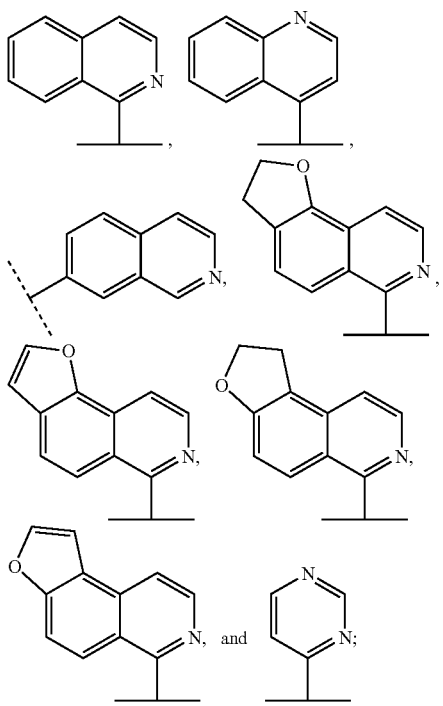

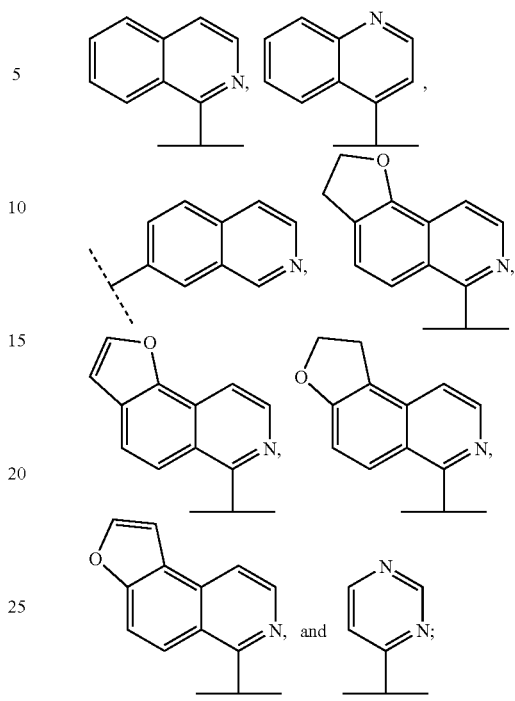

and wherein the Het is optionally substituted with $R^{200}$, wherein $R^{200}$ is one or two substituents each independently selected from methyl, methoxy, chloro, fluoro, hydroxy, phenyl, 4-methoxyphenyl, 4-(dimethylamino)phenyl, 4-cyanophenyl, and a group selected from:

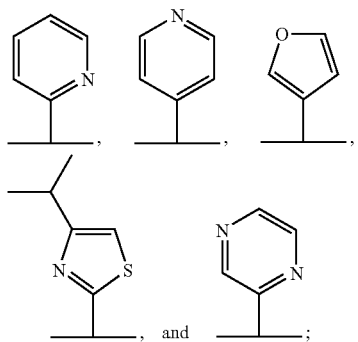

and $R^4$ is cyclopropyl optionally substituted with propyl, cyclopropylmethyl or phenylmethyl;

then $R^{31}$ is not 1,1-dimethylethyl.

More preferably, $R^{31}$ is selected from methyl, ethyl, propyl, 1-methylethyl, butyl, 1-methylpropyl, 2-methylpropyl and 1,1-dimethylethyl, each of which being optionally substituted with one to three substituents each independently selected from fluoro, chloro and bromo;

with the proviso that when n is 1; m is 2; $R^1$ is ethyl or ethenyl; and $R^2$ is —O—$R^{20}$, wherein $R^{20}$ is Het, wherein the Het is selected from:

and wherein the Het is optionally substituted with $R^{200}$, wherein $R^{200}$ is one or two substituents each independently selected from methyl, methoxy, chloro, fluoro, hydroxy, phenyl, 4-methoxyphenyl, 4-(dimethylamino)phenyl, 4-cyanophenyl, and a group selected from:

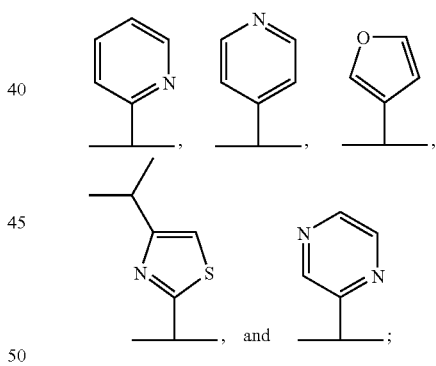

and $R^4$ is cyclopropyl optionally substituted with propyl, cyclopropylmethyl or phenylmethyl;

then $R^{31}$ is not 1,1-dimethylethyl.

Most preferably, $R^{31}$ is selected from methyl, ethyl, 1-methylethyl and 2,2,2-trichloro-1,1-dimethylethyl.

In an alternative preferred embodiment, $R^3$ is —C(O)NR$^{32}$R$^{33}$, wherein $R^{32}$ and $R^{33}$ are as defined herein.

More preferably in this embodiment, $R^{32}$ and $R^{33}$ are each independently selected from H, $(C_{1-6})$alkyl, and Het, wherein Het is a 5- or 6-membered saturated, unsaturated or aromatic monocyclic heterocycle containing one to three heteroatoms each independently selected from N, O and S.

Even more preferably, $R^{32}$ is H and $R^{33}$ is selected from methyl, ethyl, propyl, 1-methylethyl, butyl, 1-methylpropyl, 2-methylpropyl, 1,1-dimethylethyl and Het, wherein Het is selected from furyl, thienyl, pyrrolyl and pyridyl.

Most preferably, $R^{32}$ is H and $R^{33}$ is selected from ethyl, 1-methylethyl, 1,1-dimethylethyl and 2-thienyl.

In another alternative preferred embodiment, $R^3$ is $SO_vR^{34}$, wherein v and $R^{34}$ are as defined herein.

Preferably in this embodiment, v is 2 and $R^{34}$ is as defined herein.

More preferably, v is 2 and $R^{34}$ is selected from $(C_{1-6})$alkyl and $NR^{32}R^{33}$, where $R^{32}$ and $R^{33}$ are each independently selected from H and $(C_{1-6})$alkyl.

Even more preferably, v is 2 and $R^{34}$ is selected from methyl, ethyl, propyl, 1-methylethyl, butyl, 1-methylpropyl, 2-methylpropyl, 1,1-dimethylethyl and $NR^{32}R^{33}$ where $R^{32}$ and $R^{33}$ are each independently selected from H, methyl and ethyl.

Most preferably, v is 2 and $R^{34}$ is ethyl, propyl or $N(CH_3)_2$.

In yet another alternative preferred embodiment, $R^3$ is —C(O)—$R^{35}$, wherein $R^{35}$ is as defined herein.

Preferably in this embodiment, $R^{35}$ is selected from:
(a) $(C_{1-8})$alkyl optionally substituted with one to three substituents each independently selected from halo, hydroxyl, —O—$(C_{1-6})$alkyl, —S—$(C_{1-6})$alkyl, —SO—$(C_{1-6})$alkyl, —SO$_2$—$(C_{1-6})$alkyl, —O-phenyl, —S-phenyl, —SO-phenyl and —SO$_2$-phenyl, wherein the phenyl portion of the —O-phenyl, —S-phenyl, —SO-phenyl and —SO$_2$-phenyl are each optionally substituted with one to five halo substituents;
(b) $(C_{3-7})$cycloalkyl or $(C_{3-7})$cycloalkyl-$(C_{1-4})$alkyl-, each of which being optionally substituted with one to three substituents each independently selected from halo, $(C_{1-6})$alkyl, aryl and hydroxyl; and
(c) phenyl, tetrahydronaphthyl, phenyl-$(C_{1-6})$alkyl- or Het-$(C_{1-6})$alkyl-, each of which being optionally substituted with one to three substituents each independently selected from $(C_{1-6})$alkyl and hydroxyl; wherein Het is a 5- or 6-membered monocyclic heterocycle which is saturated, unsaturated or aromatic, containing one to three heteroatoms each independently selected from N, O and S.

More preferably, $R^{35}$ is selected from:
(a) methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1-ethylpropyl, 1,1-dimethylpropyl, 1,2-dimethylpropyl, 2,2-dimethylpropyl, hexyl, 2,2-dimethylbutyl, 1-ethyl-1-methylpropyl or 2-ethyl-2-methylbutyl, each of which being optionally substituted with one to three substituents each independently selected from fluoro, chloro, bromo, hydroxyl, methoxy, ethoxy, methylthio, ethylthio, —SOCH$_3$, —SOCH$_2$CH$_3$, —SO$_2$CH$_3$, —SO$_2$CH$_2$CH$_3$, —O-phenyl, —S-phenyl, —SO-phenyl and —SO$_2$-phenyl, wherein the phenyl portion of the —O-phenyl, —S-phenyl, —SO-phenyl and —SO$_2$-phenyl are each optionally substituted with one to five halo substituents;
(b) cyclopropyl, cyclobutyl, cyclopentyl, cyclohexyl, cyclopropylmethyl, cyclobutylmethyl, cyclopentylmethyl or cyclohexylmethyl, each of which being optionally substituted with one to three substituents each independently selected from fluoro, chloro, bromo, methyl, ethyl, phenyl and hydroxyl; and
(c) phenyl, tetrahydronaphthyl, phenylmethyl, phenylethyl, Het-methyl or Het-ethyl, each of which being optionally substituted with one to three substituents each independently selected from methyl, ethyl and hydroxyl; wherein Het is selected from

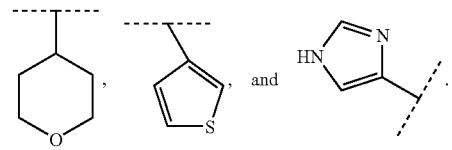

Yet more preferably, $R^{35}$ is selected from $(C_{1-8})$alkyl, $(C_{3-7})$cycloalkyl-$(C_{1-4})$alkyl-, phenyl-$(C_{1-6})$alkyl- and Het-$(C_{1-6})$alkyl-, each of which being optionally substituted with hydroxyl.

Still more preferably, $R^{35}$ is $(C_{1-6})$alkyl optionally substituted with hydroxyl.

Even more preferably, $R^{35}$ is

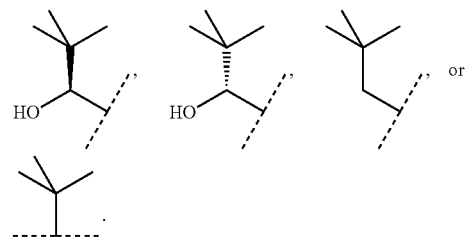

Most preferably, $R^{35}$ is

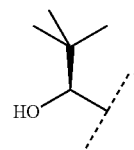

Preferably, $R^3$ is selected from:
(i) —C(O)OR$^{31}$, wherein R$^{31}$ is $(C_{1-6})$alkyl optionally substituted with one to three halogen substituents;
with the proviso that
when n is 1; m is 2; $R^1$ is ethyl or ethenyl; and
$R^2$ is —O—$R^{20}$ wherein $R^{20}$ is Het, wherein the Het is selected from:

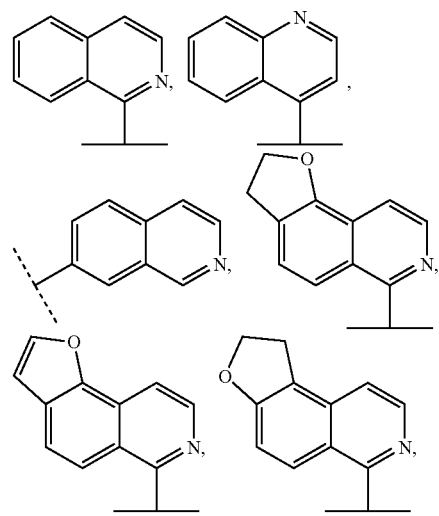

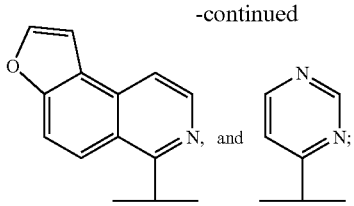

and wherein the Het is optionally substituted with $R^{200}$, wherein $R^{200}$ is one or two substituents each independently selected from methyl, methoxy, chloro, fluoro, hydroxy, phenyl, 4-methoxyphenyl, 4-(dimethylamino)phenyl, 4-cyanophenyl, and a group selected from:

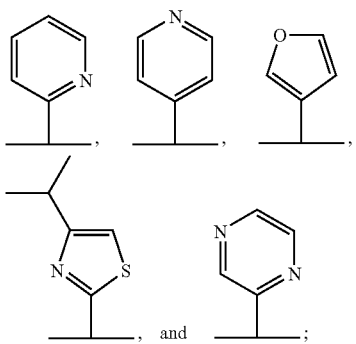

and $R^4$ is cyclopropyl optionally substituted with propyl, cyclopropylmethyl or phenylmethyl;
then $R^{31}$ is not 1,1-dimethylethyl;

(ii) —C(O)$NR^{32}R^{33}$, wherein $R^{32}$ and $R^{33}$ are each independently selected from H, $(C_{1-6})$alkyl, and Het, wherein Het is a 5- or 6-membered saturated, unsaturated or aromatic monocyclic heterocycle containing one to three heteroatoms each independently selected from N, O and S;

(iii) $SO_vR^{34}$ wherein v is 2 and $R^{34}$ is selected from $(C_{1-6})$alkyl and $NR^{32}R^{33}$, where $R^{32}$ and $R^{33}$ are each independently selected from H and $(C_{1-6})$alkyl; and (iv) —C(O)—$R^{35}$ wherein $R^{35}$ is selected from:

(a) $(C_{1-8})$alkyl optionally substituted with one to three substituents each independently selected from halo, hydroxyl, —O—$(C_{1-6})$alkyl, —S—$(C_{1-6})$alkyl, —SO—$(C_{1-6})$alkyl, —$SO_2$—$(C_{1-6})$alkyl, —O-phenyl, —S-phenyl, —SO-phenyl and —$SO_2$-phenyl, wherein the phenyl portion of the —O-phenyl, —S-phenyl, —SO-phenyl and —$SO_2$-phenyl are each optionally substituted with one to five halo substituents;

(b) $(C_{3-7})$cycloalkyl or $(C_{3-7})$cycloalkyl-$(C_{1-4})$alkyl-, each of which being optionally substituted with one to three substituents each independently selected from halo, $(C_{1-6})$alkyl, aryl and hydroxyl; and (c) phenyl, tetrahydronaphthyl, phenyl-$(C_{1-6})$alkyl- or Het-$(C_{1-6})$alkyl-, each of which being optionally substituted with one to three substituents each independently selected from $(C_{1-6})$alkyl and hydroxyl; and wherein Het is a 5- or 6-membered monocyclic heterocycle which is saturated, unsaturated or aromatic, containing one to three heteroatoms each independently selected from N, O and S.

More preferably, $R^3$ is selected from:

(i) —C(O)$OR^{31}$, wherein $R^{31}$ is selected from methyl, ethyl, propyl, 1-methylethyl butyl, 1-methylpropyl, 2-methylpropyl and 1,1-dimethylethyl, each of which being optionally substituted with one to three substituents each independently selected from fluoro, chloro and bromo;

with the proviso that
when n is 1; m is 2; $R^1$ is ethyl or ethenyl; and
$R^2$ is —O—$R^{20}$, wherein $R^{20}$ is Het, wherein the Het is selected from:

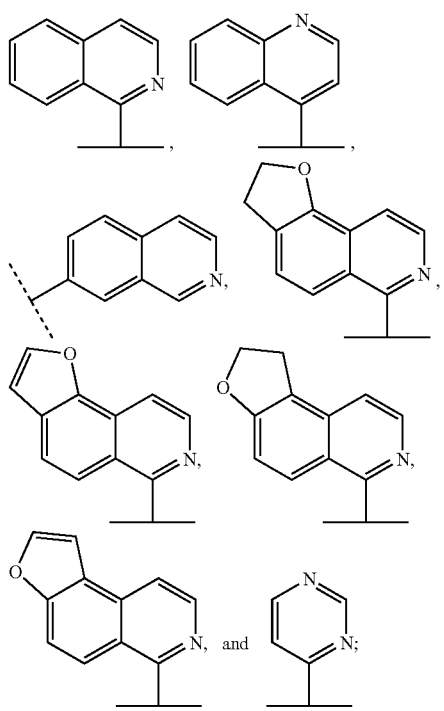

and wherein the Het is optionally substituted with $R^{200}$, wherein $R^{200}$ is one or two substituents each independently selected from methyl, methoxy, chloro, fluoro, hydroxy, phenyl, 4-methoxyphenyl, 4-(dimethylamino)phenyl, 4-cyanophenyl, and a group selected from:

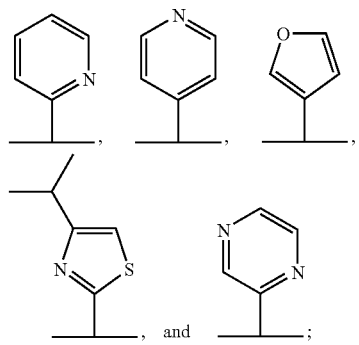

and $R^4$ is cyclopropyl optionally substituted with propyl, cyclopropylmethyl or phenylmethyl;
then $R^{31}$ is not 1,1-dimethylethyl;

(ii) —C(O)NR$^{32}$R$^{33}$, wherein R$^{32}$ is H and R$^{33}$ is selected from methyl, ethyl, propyl, 1-methylethyl, butyl, 1-methylpropyl, 2-methylpropyl, 1,1-dimethylethyl and Het, wherein Het is selected from furyl, thienyl, pyrrolyl and pyridyl;

(iii) SO$_v$R$^{34}$ wherein v is 2 and R$^{34}$ is methyl, ethyl, propyl, 1-methylethyl, butyl, 1-methylpropyl, 2-methylpropyl, 1,1-dimethylethyl and NR$^{32}$R$^{33}$, where R$^{32}$ and R$^{33}$ are each independently selected from H, methyl and ethyl; and (iv) —C(O)—R$^{35}$ wherein R$^{35}$ is selected from:
- (a) methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1-ethylpropyl, 1,1-dimethylpropyl, 1,2-dimethylpropyl, 2,2-dimethylpropyl, hexyl, 2,2-dimethylbutyl, 1-ethyl-1-methylpropyl or 2-ethyl-2-methylbutyl, each of which being optionally substituted with one to three substituents each independently selected from fluoro, chloro, bromo, hydroxyl, methoxy, ethoxy, methylthio, ethylthio, —SOCH$_3$, —SOCH$_2$CH$_3$, —SO$_2$CH$_3$, —SO$_2$CH$_2$CH$_3$, —O-phenyl, —S-phenyl, —SO-phenyl and —SO$_2$-phenyl, wherein the phenyl portion of the —O-phenyl, —S-phenyl, —SO-phenyl and —SO$_2$-phenyl are each optionally substituted with one to five halo substituents;
- (b) cyclopropyl, cyclobutyl, cyclopentyl, cyclohexyl, cyclopropylmethyl, cyclobutylmethyl, cyclopentylmethyl or cyclohexylmethyl, each of which being optionally substituted with one to three substituents each independently selected from fluoro, chloro, bromo, methyl, ethyl, phenyl and hydroxyl; and
- (c) phenyl, tetrahydronaphthyl, phenylmethyl, phenylethyl, Het-methyl or Het-ethyl, each of which being optionally substituted with one to three substituents each independently selected from methyl, ethyl and hydroxyl; wherein Het is selected from

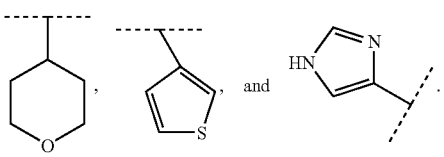

Even more preferably, R$^3$ is selected from:

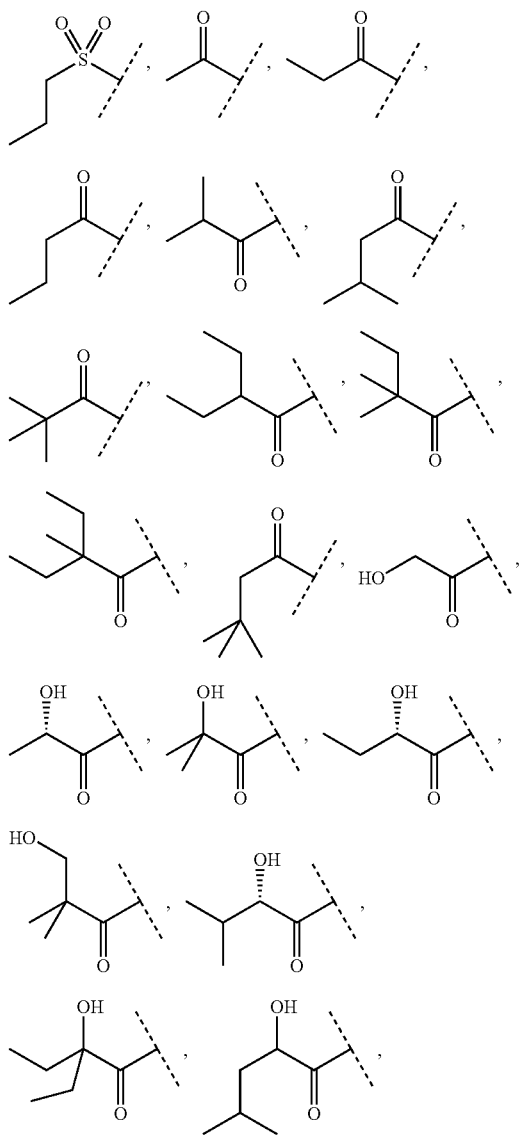

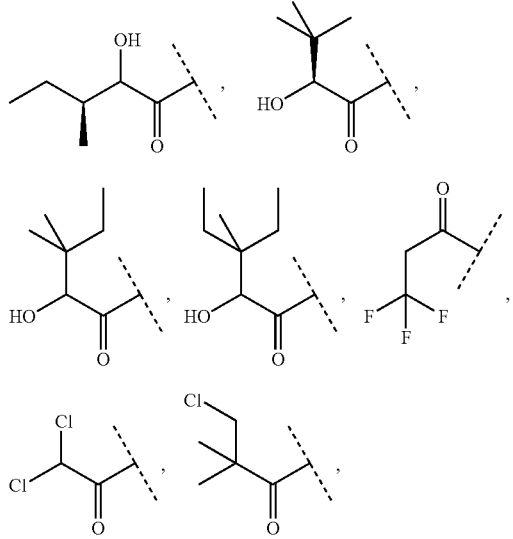

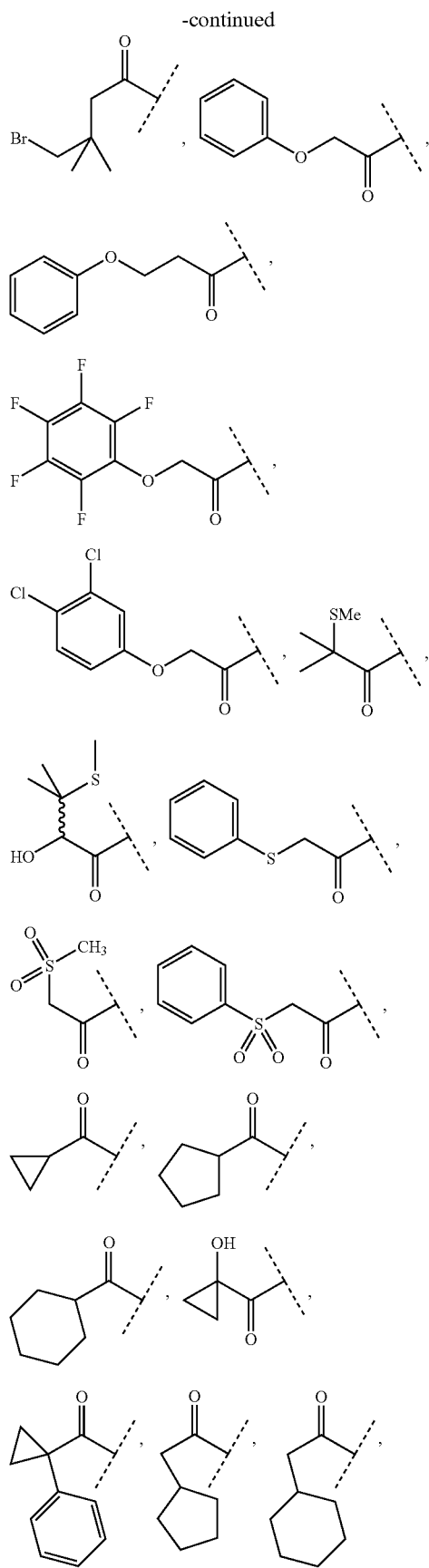
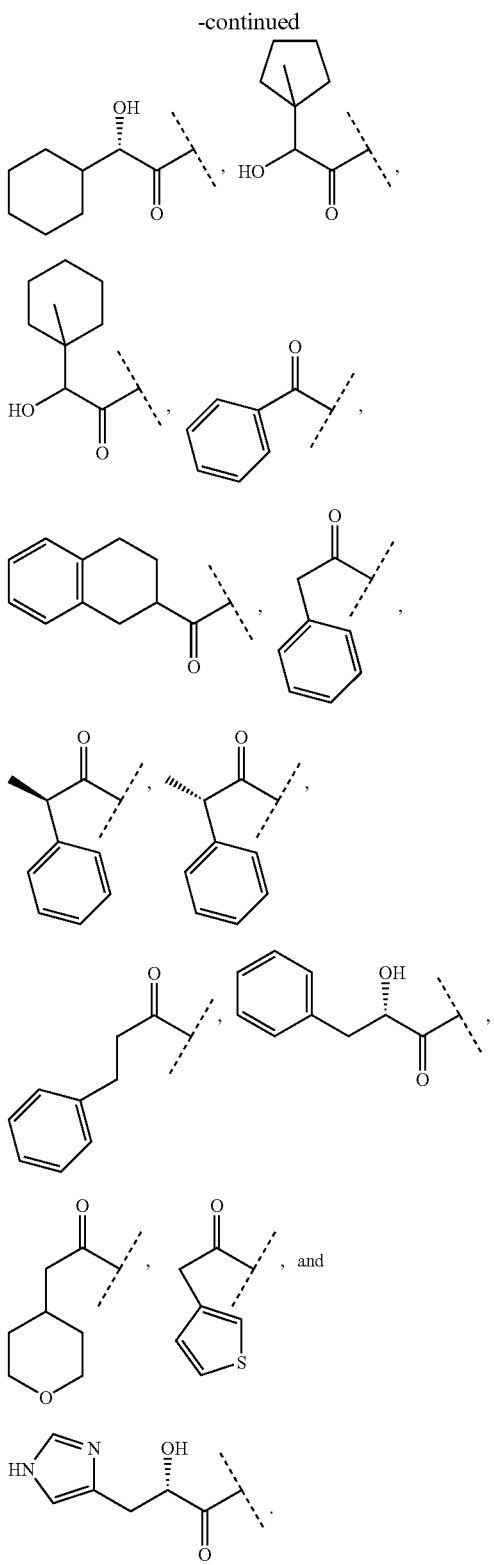
Any and each individual definition of $R^3$ as set out herein may be combined with any and each individual definition of $R^1$, $R^2$, $R^4$, n and m as set out herein.
Therefore one embodiment of the invention provides a compound of formula (I):

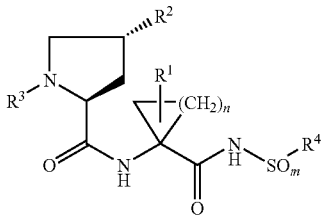

(I)

wherein
n is 1 or 2;
m is 1 or 2;
$R^1$ is $(C_{1-6})$alkyl, $(C_{2-6})$alkenyl, or $(C_{2-6})$alkynyl; wherein the $(C_{1-6})$alkyl, $(C_{2-6})$alkenyl, and $(C_{2-6})$alkynyl are optionally substituted at one or more substitutable positions with from one to three halogen atoms;
$R^2$ is selected from —NH—$R^{20}$, —O—$R^{20}$, —S—$R^{20}$, —SO—$R^{20}$, —SO$_2$—$R^{20}$, —OCH$_2$—$R^{20}$, and —CH$_2$O—$R^{20}$, wherein
  $R^{20}$ is aryl or Het, wherein the aryl and Het are optionally substituted with $R^{200}$, wherein
  $R^{200}$ is one to four substituents each independently selected from H, halogen, cyano, $(C_{1-6})$alkyl, $(C_{3-7})$cycloalkyl, aryl-$(C_{1-6})$alkyl-, aryl, Het, oxo, thioxo, —$R^{201}$, —SR$^{201}$, —SOR$^{201}$, —SO$_2$R$^{201}$, —N(R$^{202}$)R$^{201}$, and —CON(R$^{202}$)R$^{201}$; wherein each of the alkyl, cycloalkyl, aryl and Het is optionally further substituted with $R^{2000}$;
  $R^{201}$ in each case is independently selected from H, $(C_{1-6})$alkyl, aryl, $(C_{2-4})$alkenyl, $(C_{2-4})$alkynyl, —CO—$(C_{1-6})$alkyl and —CO—O—$(C_{1-6})$alkyl, wherein each of the alkyl and aryl is optionally further substituted with $R^{2000}$;
  $R^{202}$ is H or $(C_{1-6})$alkyl;
  $R^{2000}$ is one to three substituents each independently selected from halogen, $R^{2003}$, aryl, Het, —OR$^{2001}$, —SR$^{2001}$, —SOR$^{2001}$, —SO$_2$R$^{2001}$, cyano and —N(R$^{2002}$)(R$^{2001}$), wherein the aryl and Het are optionally substituted with one, two or three substituents each independently selected from $(C_{1-6})$alkyl and —O—$(C_{1-6})$alkyl;
  $R^{2001}$ in each case is independently selected from aryl, aryl-$(C_{1-6})$alkyl-, —C(O)—$R^{2003}$, —C(O)O—$R^{2003}$, —CON(R$^{2002}$)(R$^{2004}$) and $R^{2004}$;
  $R^{2002}$ in each case is independently selected from H and $(C_{1-6})$alkyl;
  $R^{2003}$ in each case is independently selected from $(C_{1-8})$alkyl, $(C_{3-7})$cycloalkyl or $(C_{3-7})$cycloalkyl-$(C_{1-4})$alkyl-, wherein the $(C_{3-7})$cycloalkyl and $(C_{3-7})$cycloalkyl-$(C_{1-4})$alkyl- are optionally substituted with one to three substituents each independently selected from $(C_{1-3})$alkyl; and
  $R^{2004}$ in each case is independently selected from H or $R^{2003}$;
$R^3$ is selected from:
  (i) —C(O)OR$^{31}$ wherein $R^{31}$ is $(C_{1-6})$alkyl or aryl, wherein the $(C_{1-6})$alkyl is substituted with one to three halogen substituents;
  (ii) —C(O)NR$^{32}$R$^{33}$, wherein $R^{32}$ and $R^{33}$ are each independently selected from H, $(C_{1-6})$alkyl, and Het;
  (iii) —SO$_v$R$^{34}$ wherein v is 1 or 2 and $R^{34}$ is selected from: $(C_{1-6})$alkyl, aryl, Het, and NR$^{32}$R$^{33}$ wherein $R^{32}$ and $R^{33}$ are as defined above; and
  (iv) —C(O)—$R^{35}$, wherein $R^{35}$ is selected from $(C_{1-6})$alkyl, $(C_{3-7})$cycloalkyl, $(C_{3-7})$cycloalkyl-$(C_{1-4})$alkyl-, aryl and aryl-$(C_{1-6})$alkyl-, each of which are optionally substituted at one to three substitutable positions with one or more substituents each independently selected from halo, $(C_{1-6})$alkyl, $(C_{3-7})$cycloalkyl, Het, —O—$(C_{1-6})$alkyl, hydroxyl, and aryl;
$R^4$ is $(C_{1-6})$alkyl, $(C_{2-6})$alkenyl, $(C_{3-7})$cycloalkyl, $(C_{3-7})$cycloalkyl-$(C_{1-6})$alkyl-, aryl, Het, aryl-$(C_{1-4})$alkyl-, or Het-$(C_{1-4})$alkyl-;
  a) the $(C_{1-6})$alkyl, $(C_{2-6})$alkenyl, aryl, Het, $(C_{3-7})$cycloalkyl-$(C_{1-6})$alkyl-, aryl-$(C_{1-4})$alkyl-, and Het-$(C_{1-4})$alkyl- optionally being substituted with nitro or substituted with one to three substituents each independently selected from halogen, hydroxy, cyano, $(C_{1-6})$alkyl, O—$(C_{1-6})$alkyl, O-aryl, —CO—NH$_2$, —CO—NH$(C_{1-4})$alkyl, —CO—N$((C_{1-4})$alkyl)$_2$, —NH$_2$, —NH$(C_{1-4})$alkyl and —N$((C_{1-4})$alkyl)$_2$, wherein the $(C_{1-6})$alkyl and O—$(C_{1-6})$alkyl are optionally substituted with one to three halogen substituents; and
  b) the $(C_{3-7})$cycloalkyl being optionally substituted with one or more substituents each independently selected from nitro, halogen, hydroxy, cyano, —O—$(C_{1-6})$alkyl, $(C_{2-4})$alkenyl, —OCF$_3$, —NH$_2$, —NH$(C_{1-4})$alkyl, —N$((C_{1-4})$alkyl)$_2$, tri$(C_{1-6})$alkylsilyl, $R^{41}$, —C(=O)—$R^{41}$, —C(=O)OR$^{41}$, —C(=O)N(R$^{42}$)R$^{41}$, —SO$_2$R$^{41}$, and —OC(=O)—$R^{41}$; wherein $R^{41}$ in each case is independently selected from:
    i) H, $(C_{3-7})$cycloalkyl, $(C_{4-7})$cycloalkenyl, Het, or aryl-$(C_{1-4})$alkyl-O—;
    ii) aryl or aryloxy, each of which being optionally substituted with $(C_{1-6})$alkyl; and
    iii) $(C_{1-8})$alkyl optionally substituted with one or more substituents each independently selected from —O—$(C_{1-6})$alkyl, hydroxy, halogen, $(C_{2-10})$alkenyl, $(C_{2-10})$alkynyl, $(C_{3-7})$cycloalkyl, $(C_{4-7})$cycloalkenyl, aryl, Het, aryloxy, and aryl-$(C_{1-4})$alkyl-O—, wherein each of the aryl and aryloxy is optionally substituted with $(C_{1-6})$alkyl; and
  $R^{42}$ is selected from H and $(C_{1-6})$alkyl; or
$R^4$ is N(R$^{N2}$)(R$^{N1}$), wherein $R^{N1}$ and $R^{N2}$ are each independently selected from H, $(C_{1-6})$alkyl, $(C_{3-7})$cycloalkyl, $(C_{3-7})$cycloalkyl-$(C_{1-6})$alkyl-, aryl and aryl-$(C_{1-6})$alkyl-; wherein the $(C_{1-6})$alkyl, $(C_{3-7})$cycloalkyl, $(C_{3-7})$cycloalkyl-$(C_{1-6})$alkyl-, aryl and aryl-$(C_{1-6})$alkyl- are optionally substituted with one or more substituents each independently selected from halogen, $(C_{1-6})$alkyl, hydroxy, cyano, O—$(C_{1-6})$alkyl, —NH$_2$, —NH$(C_{1-4})$alkyl, —N$((C_{1-4})$alkyl)$_2$, —CO—NH$_2$, —CO—NH$(C_{1-4})$alkyl, —CO—N$((C_{1-4})$alkyl)$_2$, —COOH, and —COO$(C_{1-6})$alkyl; or
$R^{N2}$ and $R^{N1}$ are linked, together with the nitrogen to which they are bonded, to form a 3- to 7-membered monocyclic saturated or unsaturated heterocycle optionally fused to at least one other cycle to form a heteropolycycle, the heterocycle and heteropolycycle optionally containing from one to three further heteroatoms each independently selected from N, S and O, and being optionally substituted with one or more substituents each independently selected from halogen, $(C_{1-6})$alkyl, hydroxy, cyano, O—$(C_{1-6})$alkyl, —NH$_2$, —NH$(C_{1-4})$alkyl, —N$((C_{1-4})$alkyl)$_2$, —CO—NH$_2$, —CO—NH$(C_{1-4})$alkyl, —CO—N$((C_{1-4})$alkyl)$_2$, —COOH, and —COO$(C_{1-6})$alkyl;

wherein Het as used herein is defined as a 3- to 7-membered heterocycle having 1 to 4 heteroatoms each independently selected from O, N and S, which may be saturated, unsaturated or aromatic, and which is optionally fused to at least one other cycle to form a 4- to 14-membered heteropolycycle having wherever possible 1 to 5 heteroatoms, each independently selected from O, N and S, the heteropolycycle being saturated, unsaturated or aromatic;

with the proviso that when n is 1; m is 2; $R^1$ is ethyl or ethenyl; and
$R^2$ is —O—$R^{20}$, wherein $R^{20}$ is Het, wherein the Het is selected from:

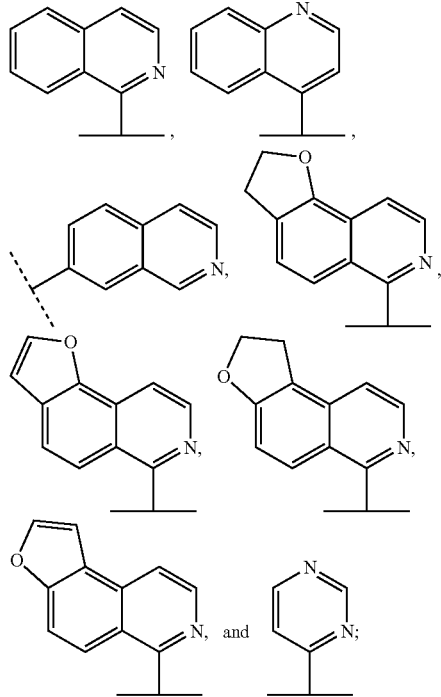

and wherein the Het is optionally substituted with $R^{200}$, wherein $R^{200}$ is one or two substituents each independently selected from methyl, methoxy, chloro, fluoro, hydroxy, phenyl, 4-methoxyphenyl, 4-(dimethylamino)phenyl, 4-cyanophenyl, and a group selected from:

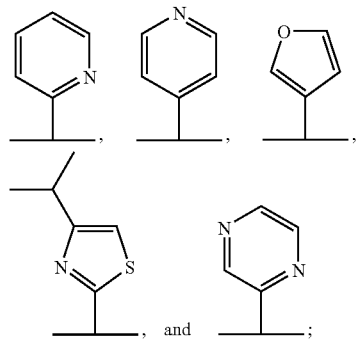

and
$R^4$ is cyclopropyl optionally substituted with propyl, cyclopropylmethyl or phenylmethyl; and
$R^3$ is —COO$R^{31}$;

then $R^{31}$ is not 1,1-dimethylethyl;

or a racemate, diastereoisomer, or optical isomer thereof, including a pharmaceutically acceptable salt thereof.

A preferred embodiment of the present invention provides compounds of formula (I) wherein:
m is 2;
n is 1;
$R^1$ is $(C_{2-6})$alkenyl or $(C_{2-6})$alkyl;
$R^2$ is —O—$R^{20}$ and $R^{20}$ is Het selected from

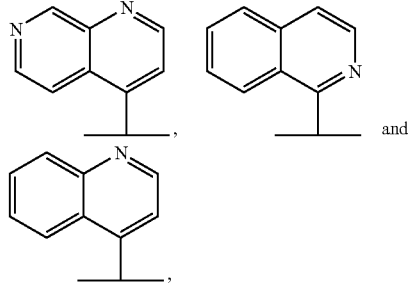

wherein the Het is unsubstituted or substituted with $R^{200}$, wherein $R^{200}$ is one to four substituents each independently selected from H, halogen, cyano, $(C_{1-6})$alkyl, aryl, Het, —O$R^{201}$, —S$R^{201}$, —SO$R^{201}$ and —SO$_2R^{201}$; wherein $(C_{1-6})$alkyl, aryl and Het are each optionally further substituted with $R^{2000}$;

$R^{201}$ is in each case independently selected from $(C_{1-6})$alkyl optionally further substituted with $R^{2000}$;

$R^{2000}$ is in each case independently one to three substituents each independently selected from halogen, $R^{2003}$, aryl, Het, —O$R^{2001}$, —S$R^{2001}$, —SO$R^{2001}$, —SO$_2R^{2001}$, cyano, and —N($R^{2002}$)($R^{2001}$); wherein the aryl and Het are each optionally substituted with one, two or three substituents each independently selected from $(C_{1-6})$alkyl and —O—$(C_{1-6})$alkyl;

$R^{2001}$ is in each case independently selected from aryl, aryl-$(C_{1-6})$alkyl-, —C(O)—$R^{2003}$, —C(O)O—$R^{2003}$, —CON($R^{2002}$)($R^{2004}$) and $R^{2004}$;

$R^{2002}$ is in each case independently selected from H and $(C_{1-6})$alkyl;

$R^{2003}$ is in each case independently selected from $(C_{1-8})$alkyl, $(C_{3-7})$cycloalkyl and $(C_{3-7})$cycloalkyl-$(C_{1-4})$alkyl-, wherein the $(C_{3-7})$cycloalkyl and $(C_{3-7})$cycloalkyl-$(C_{1-4})$alkyl- are each optionally substituted with one to three substituents each independently selected from $(C_{1-3})$alkyl;

$R^{2004}$ is in each case independently selected from H and $R^{2003}$; and

Het is in each case independently a 5- 6- or 7-membered monocyclic saturated, unsaturated or aromatic heterocycle containing 1 to 4 heteroatoms each independently selected from N, O and S.

$R^3$ is selected from:
(i) —C(O)O$R^{31}$, wherein $R^{31}$ is $(C_{1-6})$alkyl optionally substituted with one to three halogen substituents;
(ii) —C(O)N$R^{32}R^{33}$ wherein $R^{32}$ and $R^{33}$ are each independently selected from H, $(C_{1-6})$alkyl, and Het, wherein Het is a 5- or 6-membered saturated, unsaturated or aromatic monocyclic heterocycle containing one to three heteroatoms each independently selected from N, O and S;
(iii) SO$_vR^{34}$, wherein v is 2 and $R^{34}$ is selected from $(C_{1-6})$alkyl and N$R^{32}R^{33}$, where $R^{32}$ and $R^{33}$ are each independently selected from H and $(C_{1-6})$alkyl; and (iv) —C(O)—R$^{35}$ wherein R$^{35}$ is selected from:
  (a) (C$_{1-8}$)alkyl optionally substituted with one to three substituents each independently selected from halo, hydroxyl, —O—(C$_{1-6}$)alkyl, —S—(C$_{1-6}$)alkyl, —SO—(C$_{1-6}$)alkyl, —SO$_2$—(C$_{1-6}$)alkyl, —O-phenyl, —S-phenyl, —SO-phenyl and —SO$_2$-phenyl, wherein the phenyl portion of the —O-phenyl, —S-phenyl, —SO-phenyl and —SO$_2$-phenyl are each optionally substituted with one to five halo substituents;
  (b) (C$_{3-7}$)cycloalkyl or (C$_{3-7}$)cycloalkyl-(C$_{1-4}$)alkyl-, each of which being optionally substituted with one to three substituents each independently selected from halo, (C$_{1-6}$)alkyl, aryl and hydroxyl; and
  (c) phenyl, tetrahydronaphthyl, phenyl-(C$_{1-6}$)alkyl- or Het-(C$_{1-6}$)alkyl-, each of which being optionally substituted with one to three substituents each independently selected from (C$_{1-6}$)alkyl and hydroxyl; and wherein Het is a 5- or 6-membered monocyclic heterocycle which is saturated, unsaturated or aromatic, containing one to three heteroatoms each independently selected from N, O and S;

R$^4$ is selected from methyl, ethyl, propyl, 1-methylethyl, butyl, 1-methylpropyl, 2-methylpropyl, 1,1-dimethylethyl, ethenyl, 1-propenyl, 2-propenyl, cyclopropylmethyl, cyclobutylmethyl, cyclopentylmethyl, cyclohexylmethyl, phenyl, naphthyl, Het, phenylmethyl, naphthylmethyl and Het-methyl;
  a) each of which optionally being substituted with one to three substituents each independently selected from fluoro and methyl; and
  b) each of which optionally being substituted with one or two substituents each independently selected from hydroxy, trifluoromethyl, methoxy, phenoxy and trifluoromethoxy; and
  c) each of which optionally being substituted with a substituent selected from chloro, bromo, CF$_3$, cyano, nitro, —CO—NH$_2$, —CO—NHCH$_3$, —CO—N(CH$_3$)$_2$, —NH$_2$, —NH(CH$_3$) and —N(CH$_3$)$_2$;
  wherein Het is selected from thienyl, furyl, thiazolyl, benzothiazolyl, pyrrolyl, imidazolyl, pyrazolyl, pyridinyl, pyrazinyl, pyrimidinyl, pyridazinyl, indolizinyl, isoindolyl, 3H-indolyl, indolyl, quinolinyl, isoquinolinyl, tetrahydrothienyl, tetrahydrofuryl, thiadiazolyl, isoxazolyl, benzothienyl, piperidinyl, piperazinyl, morpholinyl, triazolyl, tetrazolyl, and

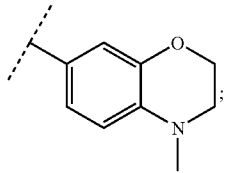

or R$^4$ is selected from cyclopropyl, cyclobutyl, cyclopentyl or cyclohexyl;
  a) each of which optionally being substituted with one to three fluoro substituents; and
  b) each of which optionally being substituted with one or two substituents each independently selected from hydroxy, trifluoromethyl, methoxy and trifluoromethoxy; and
  c) each of which optionally being substituted with a substituent selected from chloro, bromo, cyano, nitro, —CO—NH$_2$, —CO—NHCH$_3$, —CO—N(CH$_3$)$_2$, —NH$_2$, —NH(CH$_3$) and —N(CH$_3$)$_2$; and d) each of which being optionally substituted with (C$_{1-8}$)alkyl, wherein the (C$_{1-8}$)alkyl is optionally substituted with one or more substituents each independently selected from —O—(C$_{1-6}$)alkyl, hydroxy, halogen, (C$_{2-10}$)alkenyl, (C$_{2-10}$)alkynyl, (C$_{3-7}$)cycloalkyl, (C$_{4-7}$)cycloalkenyl, aryl, aryloxy, and aryl-(C$_{1-4}$)alkyl-O—, wherein each of the aryl and aryloxy is optionally substituted with (C$_{1-6}$)alkyl;

or R$^4$ is —N(R$^{N2}$)(R$^{N1}$), wherein R$^{N1}$ and R$^{N2}$ are each independently selected from H, methyl, ethyl, propyl, 1-methylethyl, methoxy, ethoxy, propoxy, 1-methylethoxy, cyclopropyl, cyclobutyl, cyclopentyl, cyclohexyl, phenyl and phenylmethyl; wherein the methyl, ethyl, propyl, 1-methylethyl, methoxy, ethoxy, propoxy, 1-methylethoxy, cyclopropyl, cyclobutyl, cyclopentyl, cyclohexyl, phenyl and phenylmethyl are optionally substituted with one or more substituents each independently selected from halogen, (C$_{1-4}$)alkyl, hydroxy, cyano, O—(C$_{1-4}$)alkyl, —NH$_2$, —NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-4}$)alkyl; or R$^{N2}$ and R$^{N1}$ are linked, together with the nitrogen to which they are bonded, to form a 3- 4-, 5- or 6-membered monocyclic saturated or unsaturated heterocycle, optionally containing from one to three further heteroatoms each independently selected from N, S and O, and optionally substituted with one, two or three substituents each independently selected from halogen, (C$_{1-4}$)alkyl, hydroxy, cyano, O—(C$_{1-4}$)alkyl, —NH$_2$—NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-4}$)alkyl;

with the proviso that when R$^1$ is ethyl or ethenyl; and

R$^2$ is —O—R$^{20}$, wherein R$^{20}$ is Het, wherein the Het is selected from:

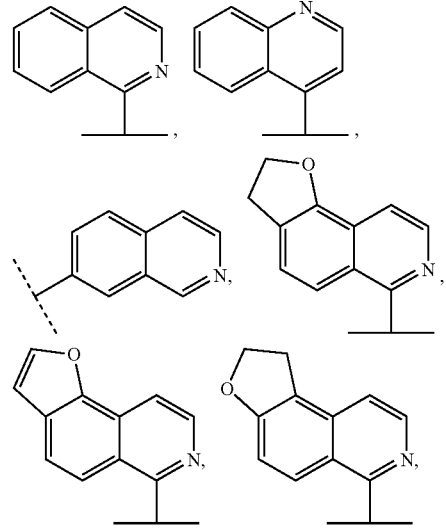

-continued

[chemical structures: furo-isoquinoline and pyrimidine]

and wherein the Het is optionally substituted with $R^{200}$, wherein $R^{200}$ is one or two substituents each independently selected from methyl, methoxy, chloro, fluoro, hydroxy, phenyl, 4-methoxyphenyl, 4-(dimethylamino)phenyl, 4-cyanophenyl, and a group selected from:

[chemical structures: pyridin-2-yl, pyridin-4-yl, furan-3-yl, 4-isopropylthiazol-2-yl, and pyrazin-2-yl]

and
$R^4$ is cyclopropyl optionally substituted with propyl, cyclopropylmethyl or phenylmethyl; and
$R^3$ is —COOR$^{31}$;
then $R^{31}$ is not 1,1-dimethylethyl.

A more preferred embodiment of the present invention provides compounds of formula (I) wherein:
n is 1;
m is 2;
$R^1$ is ethyl or ethenyl;
$R^2$ is —O—$R^{20}$ wherein $R^{20}$ is Het of the formula

[chemical structure: substituted quinoline with $R^{200d}$, $R^{200e}$, $R^{200f}$]

wherein
$R^{200d}$ is H, aryl, Het, or —OR$^{201}$, wherein Het is a 5- 6- or 7-membered monocyclic saturated, unsaturated or aromatic heterocycle containing 1 to 4 heteroatoms each independently selected from N, O and S and wherein the aryl and Het are each optionally further substituted with $R^{2000}$;
$R^{200e}$ is H or —OR$^{201}$; and
$R^{200f}$ is H, (C$_{1-6}$)alkyl, halogen, —SR$^{201}$, —SO$_2$R$^{201}$ or —OR$^{201}$; wherein the (C$_{1-6}$)alkyl is optionally further substituted with $R^{2000}$; wherein
$R^{201}$ is in each case independently selected from (C$_{1-6}$) alkyl optionally further substituted with $R^{2000}$;
$R^{2000}$ is in each case independently one to three substituents each independently selected from halogen, (C$_{3-7}$) cycloalkyl, aryl, —OR$^{2001}$ cyano, and —N(R$^{2002}$) (R$^{2001}$);
$R^{2001}$ is in each case independently selected from H, (C$_{1-6}$) alkyl and —COR$^{2003}$;
$R^{2002}$ is in each case independently selected from H and (C$_{1-6}$)alkyl; and
$R^{2003}$ is in each case independently selected from (C$_{1-8}$) alkyl, (C$_{3-7}$)cycloalkyl and (C$_{3-7}$)cycloalkyl-(C$_{1-4}$) alkyl-;
$R^3$ is selected from:
(i) —C(O)OR$^{31}$, wherein $R^{31}$ is selected from methyl, ethyl, propyl, 1-methylethyl, butyl, 1-methylpropyl, 2-methylpropyl and 1,1-dimethylethyl, each of which being optionally substituted with one to three substituents each independently selected from fluoro, chloro and bromo;
(ii) —C(O)NR$^{32}$R$^{33}$, wherein $R^{32}$ is H and $R^{33}$ is selected from methyl, ethyl, propyl, 1-methylethyl, butyl, 1-methylpropyl, 2-methylpropyl, 1,1-dimethylethyl and Het, wherein Het is selected from furyl, thienyl, pyrrolyl and pyridyl;
(iii) SO$_v$R$^{34}$, wherein v is 2 and $R^{34}$ is methyl, ethyl, propyl, 1-methylethyl, butyl, 1-methylpropyl, 2-methylpropyl, 1,1-dimethylethyl and NR$^{32}$R$^{33}$ where $R^{32}$ and $R^{33}$ are each independently selected from H, methyl and ethyl; and
(iv) —C(O)—R$^{35}$ wherein $R^{35}$ is selected from:
(a) methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1-ethylpropyl, 1,1-dimethylpropyl, 1,2-dimethylpropyl, 2,2-dimethylpropyl, hexyl, 2,2-dimethylbutyl, 1-ethyl-1-methylpropyl or 2-ethyl-2-methylbutyl, each of which being optionally substituted with one to three substituents each independently selected from fluoro, chloro, bromo, hydroxyl, methoxy, ethoxy, methylthio, ethylthio, —SOCH$_3$, —SOCH$_2$CH$_3$, —SO$_2$CH$_3$, —SO$_2$CH$_2$CH$_3$, —O-phenyl, —S-phenyl, —SO-phenyl and —SO$_2$-phenyl, wherein the phenyl portion of the —O-phenyl, —S-phenyl, —SO-phenyl and —SO$_2$-phenyl are each optionally substituted with one to five halo substituents;
(b) cyclopropyl, cyclobutyl, cyclopentyl, cyclohexyl, cyclopropylmethyl, cyclobutylmethyl, cyclopentylmethyl or cyclohexylmethyl, each of which being optionally substituted with one to three substituents each independently selected from fluoro, chloro, bromo, methyl, ethyl, phenyl and hydroxyl; and
(c) phenyl, tetrahydronaphthyl, phenylmethyl, phenylethyl, Het-methyl or Het-ethyl, each of which being optionally substituted with one to three substituents each independently selected from methyl, ethyl and hydroxyl; wherein Het is selected from

[chemical structures: tetrahydropyran-4-yl, thiophen-3-yl, and imidazolyl]

$R^4$ is selected from methyl, ethyl, 1-methylethyl, propyl, ethenyl, cyclopropyl, cyclobutyl, cyclopentyl, Het, phenyl,

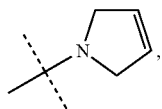

—N(CH$_3$)—OCH$_3$ and —N(CH$_3$)$_2$; wherein Het is selected from

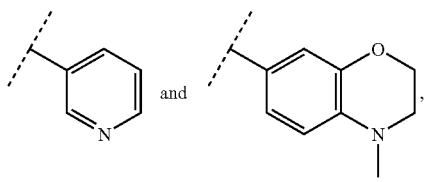

the Het being optionally substituted with phenoxy; and wherein the phenyl is optionally substituted with halogen; and wherein the cyclopropyl is optionally substituted at the 1-position with methyl, ethyl, propyl or butyl, each of the methyl, ethyl, propyl and butyl being optionally further substituted with phenyl, (C$_{3-6}$)cycloalkyl, (C$_{2-6}$)alkenyl or (C$_{1-4}$)alkoxy;

with the proviso that when R$^1$ is ethyl or ethenyl; and
R$^2$ is —O—R$^{20}$, wherein R$^{20}$ is Het, wherein the Het is selected from:

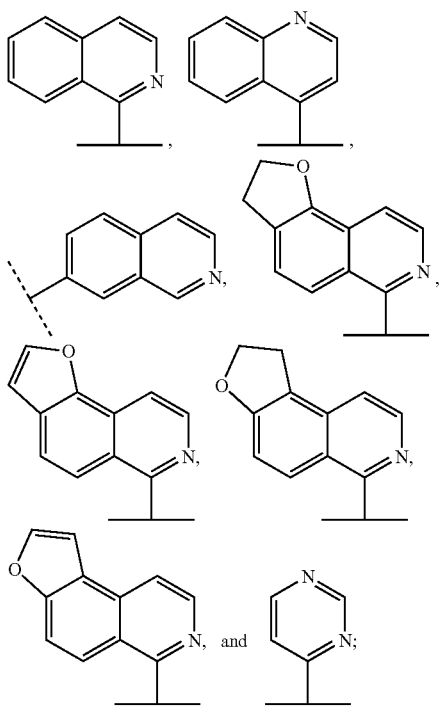

and wherein the Het is optionally substituted with R$^{200}$, wherein R$^{200}$ is one or two substituents each independently selected from methyl, methoxy, chloro, fluoro, hydroxy, phenyl, 4-methoxyphenyl, 4-(dimethylamino)phenyl, 4-cyanophenyl, and a group selected from:

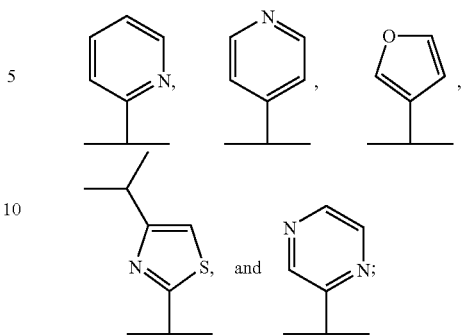

and
R$^4$ is cyclopropyl optionally substituted with propyl, cyclopropylmethyl or phenylmethyl; and
R$^3$ is —COOR$^{31}$;

then R$^{31}$ is not 1,1-dimethylethyl.

Examples of preferred compounds according to this invention are each single compound contained in Tables 1 and 2.

As discussed above, included within the scope of this invention is a pharmaceutical composition comprising an anti-hepatitis C virally effective amount of a compound of formula (I), or a pharmaceutically acceptable salt or ester thereof, and at least one pharmaceutically acceptable carrier medium or auxiliary agent.

According to a further aspect of this embodiment the pharmaceutical composition according to this invention further comprises a therapeutically effective amount of at least one other antiviral agent.

According to an alternate embodiment, the pharmaceutical composition of this invention may additionally comprise at least one other anti-HCV agent. Examples of anti-HCV agents include, but are not limited to, α-(alpha), β-(beta), δ-(delta), γ-(gamma), ω-(omega) and tau-interferon, pegylated α-interferon, ribavirin and amantadine.

According to another alternate embodiment, the pharmaceutical composition of this invention may additionally comprise at least one other inhibitor of HCV NS3 protease.

According to another alternate embodiment, the pharmaceutical composition of this invention may additionally comprise at least one inhibitor of HCV polymerase.

According to yet another alternate embodiment, the pharmaceutical composition of this invention may additionally comprise at least one inhibitor of other targets in the HCV life cycle, including but not limited to, an agent that inhibits a target selected from a helicase, an NS2/3 protease and an internal ribosome entry site (IRES) and an agent that interferes with the function of an NS5A protein.

The pharmaceutical composition of this invention may be administered orally, parenterally or via an implanted reservoir. Oral administration or administration by injection is preferred. The pharmaceutical composition of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical composition may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical composition of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", The Science and Practice of Pharmacy, 19$^{th}$ Ed. Mack Publishing Company, Easton, Pa., (1995).

Dosage levels of between about 0.001 and about 100 mg/kg body weight per day, preferably between about 0.01 and about 50 mg/kg body weight per day of the protease inhibitor compound described herein are useful in a monotherapy for the prevention and treatment of HCV mediated disease. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the composition of this invention comprises a combination of a compound of formula I, including a pharmaceutically acceptable salt thereof, and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts are formulated together with a pharmaceutically acceptable carrier, the resulting composition may be administered in vivo to mammals, such as man, to inhibit HCV NS3 protease or to treat or prevent HCV virus infection. Such treatment may also be achieved using a compound of this invention in combination with another antiviral agent. Preferred other antiviral agents are described within the Definitions section and the section of preferred pharmaceutical compositions according to this invention and include, but are not limited to: α-, β-, δ-, ω-, γ- and tau-interferon, ribavirin, amantadine; other inhibitors of HCV NS3 protease; inhibitors of HCV polymerase; inhibitors of other targets in the HCV life cycle, which include but are not limited to, agents that inhibit a target selected from a helicase, an NS2/3 protease and an internal ribosome entry site (IRES) and agents that interfere with the function of an NS5A protein; and combinations thereof. The additional agents may be combined with compounds of this invention to create a single dosage form. Alternatively these additional agents may be separately administered to a mammal as part of a multiple dosage form.

Accordingly, another embodiment of this invention provides a method of inhibiting HCV NS3 protease activity in a mammal by administering a compound of the formula (I), including a pharmaceutically acceptable salt thereof.

In a preferred embodiment, this method is useful in decreasing the NS3 protease activity of the hepatitis C virus infecting a mammal.

As discussed above, combination therapy is contemplated wherein a compound of formula (I), or a pharmaceutically acceptable salt thereof, is co-administered with at least one additional antiviral agent. Preferred antiviral agents are described hereinbefore and examples of such agents are provided in the Definitions section. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of formula (I), or a pharmaceutically acceptable salt thereof.

A compound of formula (I), or a pharmaceutically acceptable salt thereof, set forth herein may also be used as a laboratory reagent. Furthermore a compound of this invention, including a pharmaceutically acceptable salt thereof, may also be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

A compound of formula (I), including a pharmaceutically acceptable salt thereof, set forth herein may also be used as a research reagent. A compound of formula (I), including a pharmaceutically acceptable salt thereof, may also be used as positive control to validate surrogate cell-based assays or in vitro or in vivo viral replication assays.

In a further aspect of this invention is provided a process for the preparation of compounds of formula (I) comprising the steps of:

a) reacting a compound of formula (II):

(II)

wherein $R^4$ and m are as defined herein, with a strong base so as to form the corresponding amide anion of formula (IIa)

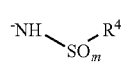
(IIa)

b) reacting an azalactone of formula (III):

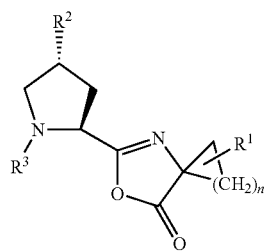
(III)

wherein $R^1$, $R^2$, $R^3$, and n are as defined herein, with the amide anion of formula (IIa). The strong base referred to in step a) is well known to one skilled in the art and includes, but is not limited to, an alkyllithium reagent (including, but not limited to, butyllithium, tert-butyllithium and the like) and the alkali metal salt of a secondary amine or silyl analog thereof (including, but not limited to, lithium hexamethyldisilazide, sodium hexamethyldisilazide, potassium hexamethyldisilazide, lithium diisopropylamide, lithium N-isopropylcyclohexylamide, lithium tetramethylpiperidide, potassium diisopropylamide, and the like).

In yet a further aspect of the present invention is provided an azalactone intermediate compound of formula (III):

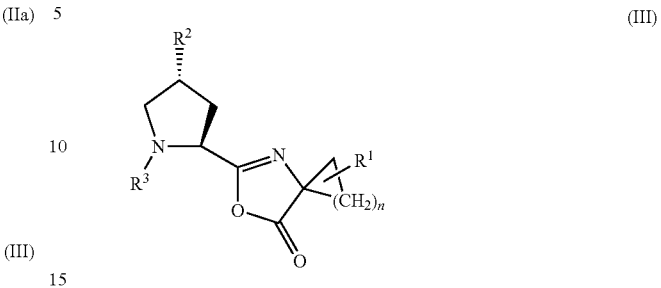
(III)

wherein $R^1$, $R^2$, $R^3$ and n are as defined herein.

A further aspect of this invention is the use of the intermediate azalactone of formula (III) as described hereinbefore in the preparation of an HCV NS3 protease inhibitor peptide analog.

Methodology

The compounds of the present invention are synthesized according to a general process wherein the P2, P1, and P1' fragments can be linked by well known peptide coupling techniques. The P2, P1, and P1' fragments may be linked together in any order as long as the final compound corresponds to compounds of formula (I), wherein $R^1$, $R^2$, $R^3$, m, n and Z are as defined herein. This process is illustrated in Scheme I (wherein CPG is a carboxyl protecting group, APG is an amino protecting group and LG is a group that may be displaced during the coupling reaction attaching $R^3$ to the P2 unit).

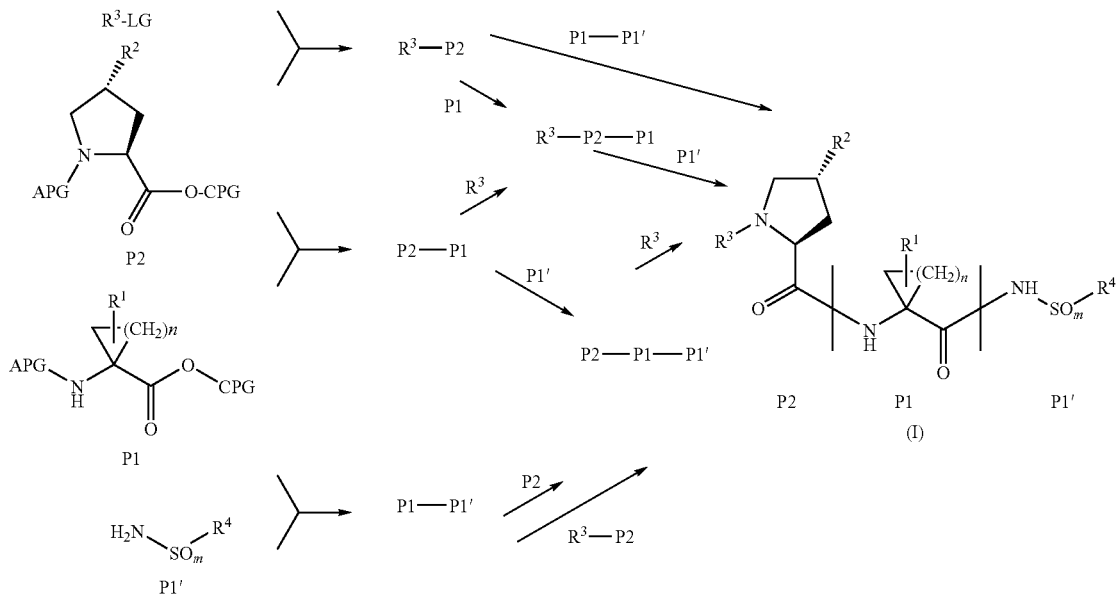

Scheme I

The P2 fragment is generally formed by attaching the $R^2$ moiety to the proline fragment using methodology as described in the examples below. This attachment may take place at any stage in this synthetic scheme, i.e., when P2 is an isolated fragment or when it has already been coupled to P1 or P1-P1'. In cases where the $R^2$ moiety is to be added at an intermediate stage after coupling to the P1 and/or P1-P1' fragments, the P2 fragment shown above is replaced with a suitable precursor fragment for the purposes of this scheme.

Generally, peptides are elongated by deprotecting the α-amino group of the N-terminal residue and coupling the unprotected carboxyl group of the next suitably N-protected amino acid through a peptide linkage using well known methods. This deprotection and coupling procedure is repeated until the desired sequence is obtained. This coupling can be performed with the constituent amino acid fragments in stepwise fashion or by solid phase peptide synthesis according to the method originally described in Merrifield, J. Am. Chem. Soc., (1963), 85, 2149-2154.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole. These coupling reactions can be performed in either solution (liquid phase) or solid phase.

More explicitly, the coupling step involves the dehydrative coupling of a free carboxyl of one reactant with the free amino group of the other reactant in the presence of a coupling agent to form a linking amide bond. Descriptions of such coupling agents are found in general textbooks on peptide chemistry, for example, M. Bodanszky, "Peptide Chemistry", 2nd rev ed., Springer-Verlag, Berlin, Germany, (1993). Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A practical and useful coupling agent is the commercially available (benzotriazol-1-yloxy)tris-(dimethylamino)-phosphonium hexafluorophosphate, either by itself or in the presence of 1-hydroxybenzotriazole. Another practical and useful coupling agent is commercially available 2-(1H-benzotriazol-1-yl)-N,N,N',N'-tetramethyluronium tetrafluoroborate. Still another practical and useful coupling agent is commercially available O-(7-azabenzotriazol-1-yl)-N,N,N',N'-tetramethyluronium hexafluorophosphate.

The coupling reaction is conducted in an inert solvent, e.g. dichloromethane, acetonitrile or dimethylformamide. An excess of a tertiary amine, e.g. diisopropylethylamine, N-methylmorpholine or N-methylpyrrolidine, is added to maintain the reaction mixture at a pH of about 8. The reaction temperature usually ranges between 0° C. and 50° C. and the reaction time usually ranges between 15 min and 24 h.

When a solid phase synthetic approach is employed, the C-terminal carboxylic acid is attached to an insoluble carrier (usually polystyrene). These insoluble carriers contain a group that will react with the carboxylic group to form a bond that is stable to the elongation conditions but readily cleaved later. Examples of which are: chloro- or bromomethyl resin, hydroxymethyl resin, trityl resin and 2-methoxy-4-alkoxybenzylalcohol resin.

Many of these resins are commercially available with the desired C-terminal amino acid already incorporated. Alternatively, the amino acid can be incorporated on the solid support by known methods (Wang, S.-S., J. Am. Chem. Soc., (1973), 95, 1328; Atherton, E.; Shepard, R. C. "Solid-phase peptide synthesis; a practical approach" IRL Press: Oxford, (1989); 131-148). In addition to the foregoing, other methods of peptide synthesis are described in Stewart and Young, "Solid Phase Peptide Synthesis", 2nd ed., Pierce Chemical Co., Rockford, Ill. (1984); Gross, Meienhofer, Udenfriend, Eds., "The Peptides: Analysis, Synthesis, Biology", Vol. 1, 2, 3, 5, and 9, Academic Press, New-York, (1980-1987); Bodansky et al., "The Practice of Peptide Synthesis" Springer-Verlag, New-York (1984) in the literature.

EXAMPLES

The present invention is illustrated in further detail by the following non-limiting examples.

Temperatures are given in degrees Celsius. Solution percentages express a weight to volume relationship, and solution ratios express a volume to volume relationship, unless stated otherwise. Nuclear magnetic resonance (NMR) spectra were recorded on a Bruker 400 MHz spectrometer; the chemical shifts (δ) are reported in parts per million. Flash chromatography was carried out on silica gel ($SiO_2$) according to Still's flash chromatography technique (W. C. Still et al., J. Org. Chem., (1978), 43, 2923). Analytical HPLC was carried out under standard conditions using a Combiscreen ODS-AQ C18 reverse phase column, YMC, 50×4.6 mm i.d., 5 µM, 120 Å at 220 nM, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
| --- | --- | --- | --- |
| 0 | 3.0 | 95 | 5 |
| 0.5 | 3.0 | 95 | 5 |
| 6.0 | 3.0 | 50 | 50 |
| 10.5 | 3.5 | 0 | 100 |

Abbreviations used in the examples include

AcOH: acetic acid;

Bn: benzyl;

Boc: tert-butyloxycarbonyl {$Me_3C$—O—C(O)};

brosyl: p-bromobenzenesulfonyl;

CDI: N,N'-Carbonyldiimidazole;

DBU: 1,8-diazabicyclo[5.4.0]undec-7-ene;

DCC: 1,3-dicyclohexylcarbodiimide;

DCM: dichloromethane;

DIC: diisopropylcarbodiimide;

DIPEA: diisopropylethylamine;

DMAP: 4-dimethylaminopyridine;

DME: 1,2-dimethoxyethane;

DMF: dimethylformamide;

DMSO: dimethylsulfoxide;

EDTA: ethylenediaminetetraacetic acid;

Et: ethyl;

EtOH: ethanol;

EtOAc: ethyl acetate;

Et$_2$O: diethyl ether;

HATU: [O-7-azabenzotriazol-1-yl)-1,1,3,3-tetramethyluronium hexafluorophosphate];

HOAt: 1-hydroxy-7-azabenzotriazole;

HPLC: high performance liquid chromatography;

IBCF: iso-butyl chloroformate;

LAH: lithium aluminum hydride;

LHMDS: lithium hexamethyldisilazide;

Me: methyl;

MeOH: methanol;

MS: mass spectrometry;

NaHMDS: sodium hexamethyldisilazide;

NMO: N-methylmorpholine-N-oxide;

NMP: N-methylpyrrolidone;

Pr: propyl;

$t_R$: retention time;

TBAF: tetra-n-butylammonium fluoride;

TBDMSCl: tert-butyldimethylsilyl chloride;

TBTU: 2-(1H-benzotriazole-1-yl)-1,1,3,3-tetramethyluronium tetrafluoroborate;

TEA: triethylamine;

TFA: trifluoroacetic acid;

THF: tetrahydrofuran;

TPAP: tetra-n-propylammonium perruthenate;

Tris/HCl: tris(hydroxymethyl)aminomethane hydrochloride;

Ts: tosyl (p-methylbenzenesulfonyl)

RT: room temperature.

Synthesis of P1 Fragments

The preparation, separation and identification of the stereoisomers of the P1 fragments of compounds of formula (I) were carried out using the protocols outlined in WO 00/59929, published Oct. 12, 2000, and WO 00/09543, published on Feb. 24, 2000. In particular, reference is made to pages 33-35, Example 1 of WO00/59929 and pages 56-69, Example 9-20 of WO 00/09543 for the preparation of 1-aminocyclopropylcarboxylic acid P1 moieties.

Synthesis of P2 Fragments

Generally, P2 moieties of compounds of formula (I) can be prepared using the protocols outlined in WO 00/59929, WO 00/09543, WO 03/064456 and WO 03/064416.

R$^2$ moieties of compounds of formula 1 are either commercially available, have been described previously in the literature or are synthesized according to methods provided in the examples below. General methods for the synthesis of some of these fragments are described in WO 00/59929, WO 00/09543, WO 03/064456 and WO 03/064416 and more specific and pertinent examples are provided below.

General methods for the introduction of the R$^2$ substituent on the proline to produce the required 4-substituted proline where R$^{20}$ is attached to the proline ring via an oxygen (—O—) or a sulfur (—S—), can be carried out as described in WO 00/59929, WO 00/09543, WO 03/064456 and WO 03/064416. Other analogs can also be synthesized using this methodology.

Preparation of P2 Aniline Moieties

The corresponding anilines in P2 fragments are commercially available or may require some well known chemical transformation. For example the nitro derivative may be commercially available and is then converted to the corresponding amine by using a reducing agent. Also when the carboxylic acid is commercially available, it can be transformed into the corresponding amine via a Curtius rearrangement.

Example 1A

Synthesis of P2 Building Block 2-methyl-3-methoxy Aniline (1a2)

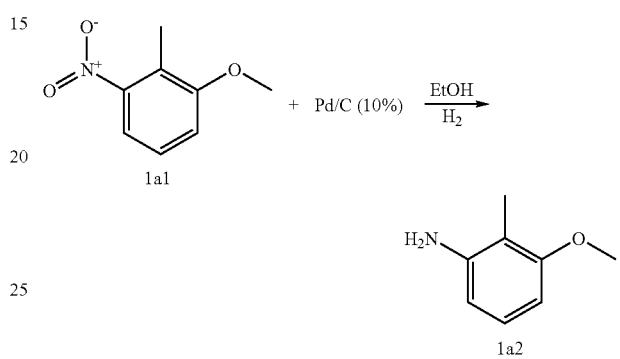

To a solution of 2-methyl-3-nitro anisole which is commercially available (1a1) (5.1 g; 30.33 mmol; requires ~30 min. to dissolve) in absolute ethanol (85 mL) was added 10% Pd/C catalyst (500 mg). The solution was hydrogenated under a hydrogen filled balloon at atmospheric pressure and room temperature for 19 h. The reaction mixture was filtered through a Celite pad, rinsed and evaporated to dryness to obtain the compound 1a2 as a deep mauve oil (4.1 g; 29.81 mmol; 98% yield). MS 137 (MH)+. Reverse Phase HPLC Homogeneity @ 220 nm (0.06% TFA; CH$_3$CN; H$_2$O): 99%.

Example 1B

Synthesis of P2 Moiety 2-bromo-3-methoxy Aniline (1B4)

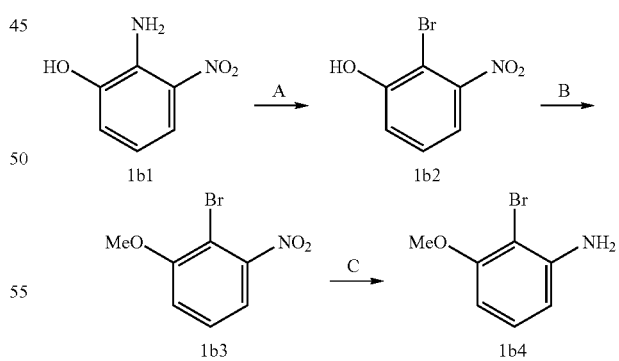

Step A: 2-Amino-3-nitrophenol 1b1 (5 g; 32.4 mmol) was dissolved in H$_2$O (29.5 mL) and 1,4-dioxane (14.7 mL). The mixture was heated to reflux and hydrobromic acid (48%; 16.7 mL; 147 mmol) was added dropwise over a period of 20 min. Upon completion of the addition, the reflux was maintained an additional 15 min. The reaction was cooled to 0° C. (ice bath), and sodium nitrite (2.23 g; 32.3 mmol) in H$_2$O (20 mL) was added over a period of 30 min. The stirring was continued for 15 min. at 0° C., the mixture transferred to a jacketed dropping funnel (0° C.) and added dropwise to a stirred mixture of Cu(I)Br (5.34 g; 37.2 mmol) in H$_2$O (29.5 mL) and HBr (48%; 16.7 mL; 147 mmol) at 0° C. The reaction was stirred for 15 min. at 0° C., warmed to 60° C., stirred for an additional 15 min., cooled to room temperature, and left to stir overnight. The reaction mixture was transferred to a separatory funnel and extracted with ether (3×150 mL). The organic layers were combined, washed with brine (1×), dried (Na$_2$SO$_4$), filtered and concentrated to afford the crude product (7.99 g) as a red-brown oil. The crude material was purified by flash column chromatography (1:25 ultra pure silica gel, 230-400 mesh, 40-60 mm, 60 angstroms; CH$_2$Cl$_2$ as the solvent) to afford pure 2-bromo-3-nitrophenol 1b2 (45%; 3.16 g) as an orange-brown solid. MS 217.8 (MH)$^+$. Homogeneity by HPLC (TFA) @ 220 nm: 97%.

Step B: The nitrophenol starting material 1b2 (3.1 g; 14.2 mmol) was dissolved in DMF (20 mL) and to the solution was added ground cesium carbonate (5.58 g; 17.1 mmol) followed by MeI (2.6 mL; 42.5 mmol). The mixture was stirred at room temperature overnight. The DMF was evaporated, the residue taken up in ether (1×200 mL), washed with water (1×200 mL), brine (4×100 mL), dried (MgSO$_4$), filtered and evaporated to afford the crude 2-bromo-3-nitroanisole 1b3 (94%; 3.1 g) as an orange solid. MS 234 (M+2H)$^+$; Homogeneity by HPLC (TFA) @ 220 nm: 98%

Step C: 2-Bromo-3-nitroanisole 1b3 (1.00 g; 4.31 mmol) was dissolved in glacial acetic acid (11.0 mL)/ethanol (11.0 mL) and to the solution was added iron powder (0.98 g; 17.5 mmol). The mixture was stirred at reflux for 3.5 hr and worked up. The reaction mixture was diluted with water (35 mL), neutralized with solid Na$_2$CO$_3$ and the product extracted with CH$_2$Cl$_2$ (3×50 mL). The extracts were dried (Na$_2$SO$_4$), filtered and concentrated in vacuo to afford the crude product, 2-bromo-3 methoxyaniline 1b4 (91%; 0.79 g) as a pale yellow oil. MS 201.8 (MH)$^+$; Homogeneity by HPLC (TFA) @ 220 nm: 95%

Example 1C

Synthesis of P2 Moiety 2-chloro-3-methoxy Aniline (1c3)

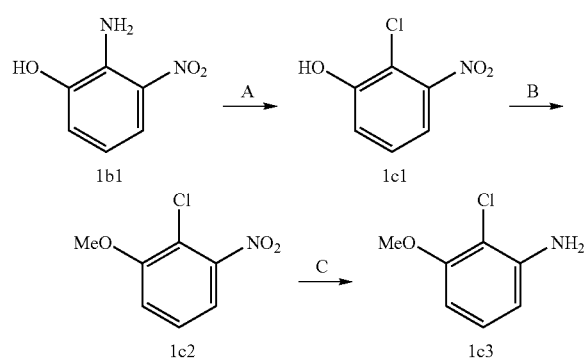

Step A: 2-Amino-3-nitrophenol 1b1 (5 g; 32.4 mmol) was dissolved in concentrated HCl (75 mL) and 1,4-dioxane (14.7 mL). The mixture was heated to 70° C. until most of the solids were in solution. The reaction mixture was cooled to 0° C. (ice bath), and sodium nitrite (2.23 g; 32.3 mmol) in H$_2$O (5.4 mL) was added over a period of 3 hours to the brown solution. The temperature was maintained below 10° C. during the addition and the stirring was continued for an additional 15 min. at 0° C. This diazonium intermediate was poured into a solution of Cu(I)Cl (3.8 g; 38.9 mmol) in H$_2$O (18.5 mL) and conc. HCl (18.5 mL) at 0° C. The reaction was stirred for 15 min. at 0° C., warmed to 60° C., and stirred for an additional 15 min. The reaction mixture was then brought to room temperature, and left to stir overnight. The reaction mixture was transferred to a separatory funnel and extracted with ether (3×150 mL). The organic layers were combined, washed with brine (1×), dried (Na$_2$SO$_4$), filtered and concentrated to afford the crude product (5.83 g) as a red-brown oil. The crude material was purified by flash column chromatography (1:25 ultra pure silica gel, 230-400 mesh, 40-60 mm, 60 angstroms; 3:1 hexane/EtOAc as the solvent) to afford pure 2-chloro-3-nitrophenol 1c1 (48%; 2.7 g) as an orange solid. MS 171.8 (MH)$^+$: Homogeneity by HPLC (TFA) @ 220 nm: 96%.

Relevant literature for the Sandmeyer Reaction: *J. Med. Chem.*, 1982, 25(4), 446-451.

Step B: The nitrophenol starting material 1c1 (1.3 g; 7.49 mmol) was dissolved in DMF (10 mL) and to this solution was added ground cesium carbonate (2.92 g; 8.96 mmol), followed by MeI (1.4 mL; 22.5 mmol). The mixture was stirred at room temperature overnight. The DMF was evaporated in vacuo and the residue taken up in ether (150 mL), washed with water (150 mL), brine (4×100 mL), and then dried over (MgSO$_4$). The organic phase was filtered and evaporated to afford the crude 2-chloro-3-nitroanisole 1c2 (98%; 1.38 g) as an orange solid.

Homogeneity by HPLC (TFA) @ 220 nm: 93%.

Step C: 2-Chloro-3-nitroanisole 1c2 (1.38 g; 7.36 mmol) was dissolved in a mixture of glacial acetic acid (19 mL)/ethanol (19 mL). To this solution was added iron powder (1.64 g; 29.4 mmol). The mixture was stirred at reflux for 3.5 hr and worked up. The reaction mixture was diluted with water (70 mL), neutralized with solid Na$_2$CO$_3$ and the product extracted with CH$_2$Cl$_2$ (3×150 mL). The extracts were combined and washed with sat. brine and then dried over (Na$_2$SO$_4$), filtered and concentrated in vacuo to afford the crude product, 2-chloro-3-methoxyaniline 1c3 (100%; 1.2 g) as a yellow oil. This material was used as such in the following steps. MS 157.9 (MH)$^+$; Homogeneity by HPLC (TFA) @ 220 nm: 86%.

Preparation of P2 Quinoline Moieties

Example 1D

General Protocol for the Preparation of 2-alkoxy Substituted 4-hydroxyquinolines (1d)

The following P2 hydroxyquinoline moieties bearing an alkoxy group (OR$^{201}$) at the 2-position, wherein R$^{200a}$ and R$^{200b}$ are each independently selected from R$^{200}$ wherein R$^{200}$ is as defined herein can be prepared according to the following scheme:

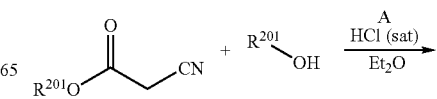

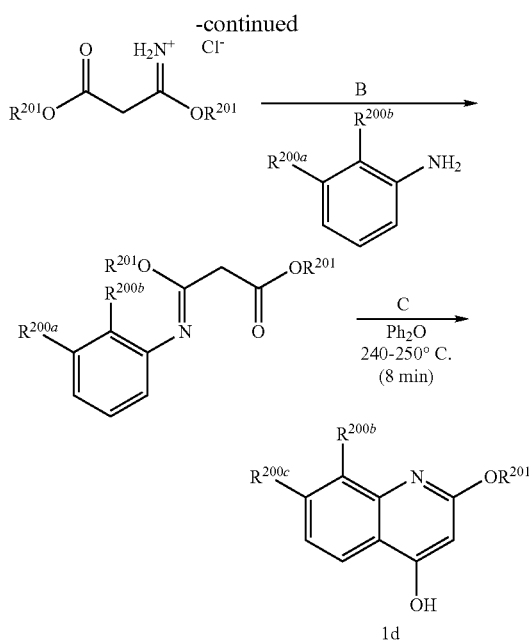

Briefly, following the known Pinner synthesis, a suitably functionalized cyanoester is condensed with the corresponding alcohol using a fully saturated HCl/Et$_2$O solution [Neilson, in Patai, "The Chemistry of Amidines and Imidates." pp. 385-489, Wiley, NY, 1975.]. The resulting imidate salt is then subsequently condensed with an appropriately substituted aniline to form the aniline derived imidate. Thermal cyclization affords the corresponding 2-alkoxy substituted 4-hydroxyquinolines 1d.

For example, when $R^{201}$ is Et in the above scheme, ethyl cyanoacetate and ethanol are used as reagents. When $R^{201}$ is Me in the above scheme, methyl cyanoacetate and methanol are used as reagents Example 1E General Protocol for the Preparation of 2-alkyl Substituted 4-hydroxyquinolines (1e)

The following P2 hydroxyquinoline moieties where $R^{200c}$ of the β-ketoester moiety is an alkyl group and wherein $R^{200a}$ and $R^{200b}$ are each independently selected from $R^{200}$ wherein $R^{200}$ is as defined herein can be prepared according to the following scheme:

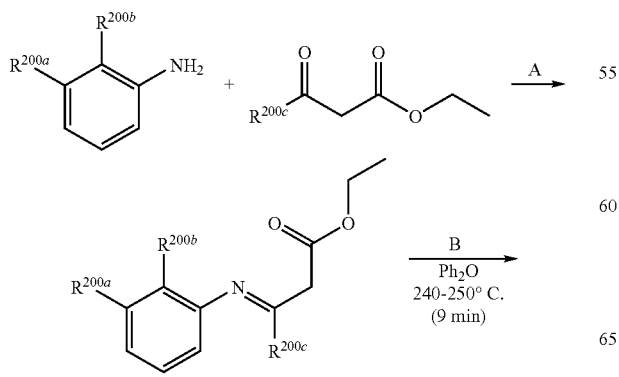

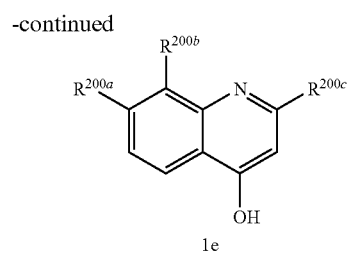

Briefly, appropriately substituted β-ketoesters are condensed with substituted anilines and subsequently thermally cyclized to afford the corresponding 2-alkyl substituted hydroxyquinolines 1e. For example, when the initial condensation reaction with the aniline (step A) is performed with the corresponding methyl ketone, a methyl group is incorporated in the 2-position of the resulting hydroxyquinoline.

Example 1F

General Protocol for the Preparation of 2-alkylthio Substituted 4-hydroxyquinolines (1f)

In general, various P2 hydroxyquinolines having a 2-alkylthio group (SR$^{201}$ wherein R$^{201}$ is (C$_{1-6}$)alkyl) at the 2-position wherein $R^{200a}$ and $R^{200b}$ are each independently selected from $R^{200}$ wherein $R^{200}$ is as defined herein were prepared as shown in the following scheme:

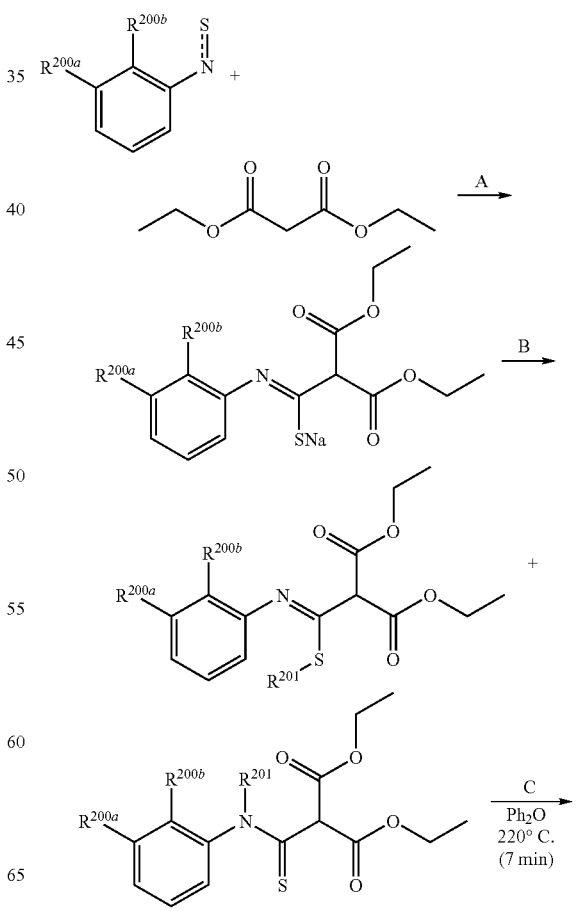

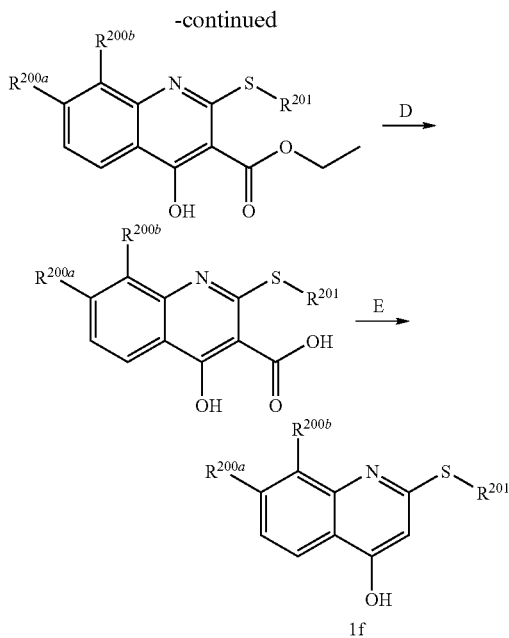

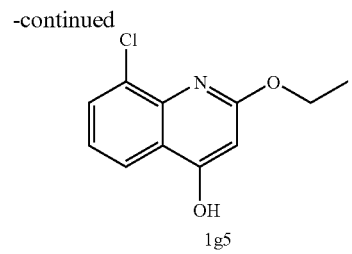

Briefly, condensation of diethyl malonate under basic conditions with a suitably functionalized isothiocyanate produces the malonate adduct as a salt. Treatment of the salt with an alkylating reagent (e.g. EtI) produces a mixture of S- and N-alkylated products. Thermal cyclization of this mixture gives the 3-ethyl carboxylate which is saponified and decarboxylated to produce the desired 2-alkylthio substituted hydroxyquinolines 1f. For example, utilization of EtI in the alkylation step results in the formation of the 2-ethylthio analog.

Example 1G

Synthesis of P2 Moiety
2-ethoxy-4-hydroxy-8-chloroquinoline (1g5)

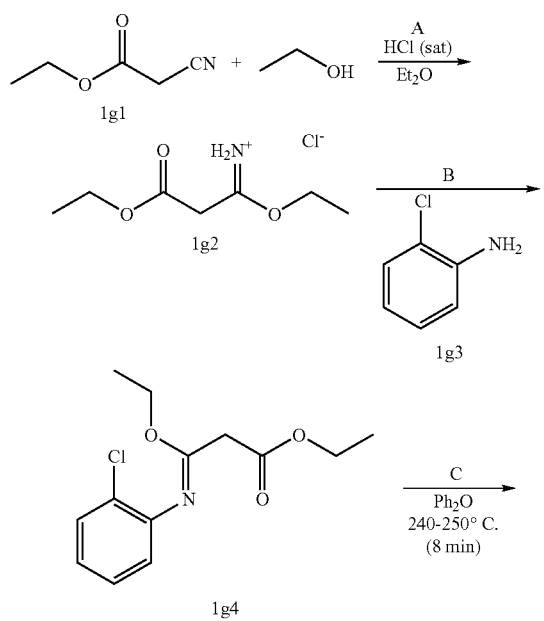

Step A: To ethyl cyanoacetate 1g1 (23 g, 0.203 mol) was added absolute ethanol (10 g, 12.7 mL, 0.22 mol) in diethyl ether (20 mL). The solution was cooled to 0° C. in an ice bath before being treated with HCl gas (bubbled through solution for 12 minutes resulted in an increase in weight of 12 g (~0.33 mol)). This solution was stirred at 0° C. for 6 h and then allowed to warm to RT and was stirred for 16 h. The resultant solid was broken up and washed several times with ether and then placed in vacuo for several hours. The imidate salt 1g2 was obtained as a white solid (36.4 g, 92%) and was stored under a nitrogen atmosphere. The $^1$H NMR was consistent with the desired product.

Step B: The imidate salt 1g2 (1.47 g, 7.5 mmol, 1 eq.) was combined with 2-chloroaniline 1g3 (0.96 g, 7.50 mmol, 1 eq.) in ethanol (15 mL) under an $N_2$ atmosphere. The reaction mixture was stirred at RT (16 h) and monitored by HPLC. The reaction mixture was concentrated and then purified directly over silica gel (eluent: 10% EtOAc/Hexanes) to afford the condensation product 1g4 as a clear oil (1.73 g, 86%). MS electrospray: (MH)$^+$; 270 and (M–H)$^-$; 268. TLC (UV) Rf=0.50 (10% EtOAc/hexane).

Step C: The condensation product 1g4 (1.73 g, 6.41 mmol) was dissolved in diphenyl ether (10 mL) and placed in a sand bath (300° C.). The internal temperature was monitored and allowed to stay between 240-250° C. for 8 minutes. The mixture was cooled and then directly loaded on a silica gel column and eluted first with hexanes, then with 30% EtOAc/Hexanes and finally 50% EtOAc/hexanes. The product was concentrated and dried in vacuo to give the corresponding 4-hydroxyquinoline derivative 1g5 as a beige crystalline solid (0.76 g, 53%). MS electrospray: (M+H)$^+$; 224 and (M–H)$^-$; 222.

Example 1H

Synthesis of P2 Moiety 4-hydroxy-8-chloroquinoline 1h3

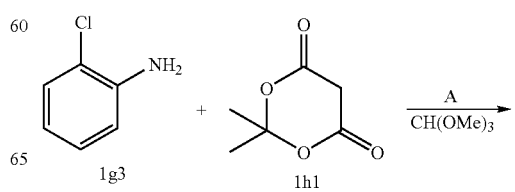

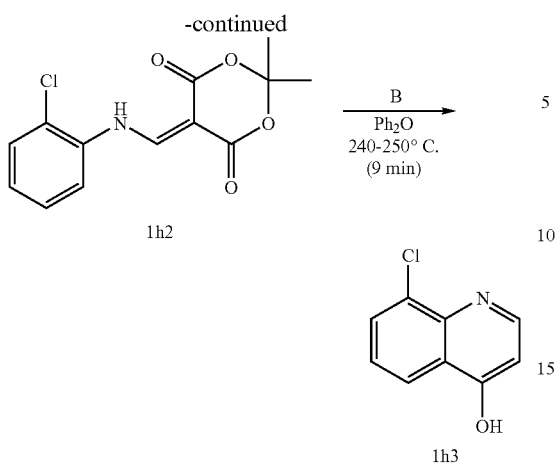

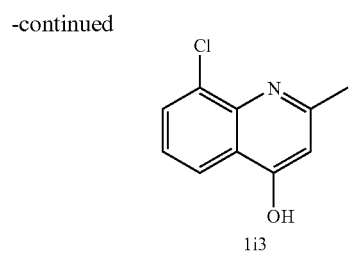

Step A: To 2-chloroaniline 1g3 (1.6 mL, 15.2 mmol, 1 eq) dissolved in anhydrous acetonitrile (50 mL) at RT was added Meldrum's acid 1h1 (2.41 g, 16.73 mmol, 1.1 eq), followed by trimethyl orthoformate (2.0 mL, 18.25 mmol, 1.2 eq). The resulting mixture was heated to reflux (95° C.) for 2 h and monitoring by analytical HPLC until complete. The resulting solution was cooled to RT and evaporated to dryness to afford a beige solid that was recrystallized from boiling MeOH. After drying in vacuo adduct 1 h2 was obtained as a bright yellow solid (2.29 g, 53%).

Step B: In a pre-heated sand bath (300-350° C.), diphenyl ether (6 mL) was heated until the internal temperature reached 220° C. Adduct 1 h2 (981 mg, 3.48 mmol) was added portionwise over ca. 4 min period (gas evolution) to the heated solvent. The temperature (220° C.) was maintained for another 5 min. after which the solution was allowed to cool. Upon cooling, the product crashed out of solution and was filtered and washed with diethyl ether. After drying in vacuo (16 h), product 1h3 was obtained as a beige solid (417 mg, 67%). MS: (M+H)$^+$; 180.

Example 1I

Synthesis of P2 Moiety
8-chloro-4-hydroxy-2-methylquinoline 2i3

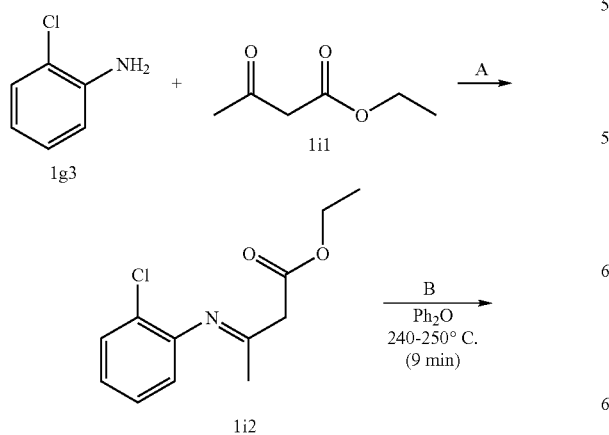

Step A: To a solution of ethyl acetoacetate 1i1 (1.21 mL, 9.51 mmol; 1 eq) in benzene (20 mL) was added 2-chloroaniline 1g3 (1.0 mL; 9.51 mmol; 1 eq) followed by catalytic PTSA (13 mg). The reaction flask was equipped with a Dean-Stark apparatus and heated to reflux for 2 hours. The solvent was removed and the residue purified by column chromatography using silica gel (eluent: 10% EtOAc/Hexanes; $R_f$=0.48) to give compound 1i2 (1.46 g, 64%) as a clear oil. MS: (M+H)$^+$; 240, HPLC homogeneity=99.5%.

Step B: In a pre-heated sand bath (300-350° C.), compound 1i2 (730 mg, 3.0 mmol) in diphenyl ether (8 mL) was heated until the internal temperature reached 220° C. and that temperature was maintained for 7 minutes after which the solution was allowed to cool. Upon cooling, a beige solid crashed out and was filtered and washed with diethyl ether. After drying, the desired quinoline 1i3 was obtained as a beige solid (452 mg, 77%). MS: (M+H)$^+$; 194, HPLC homogeneity=99%.

Example 1J

Synthesis of P2 Moiety
2-ethylthio-8-chloro-4-hydroxyquinoline (1j7)

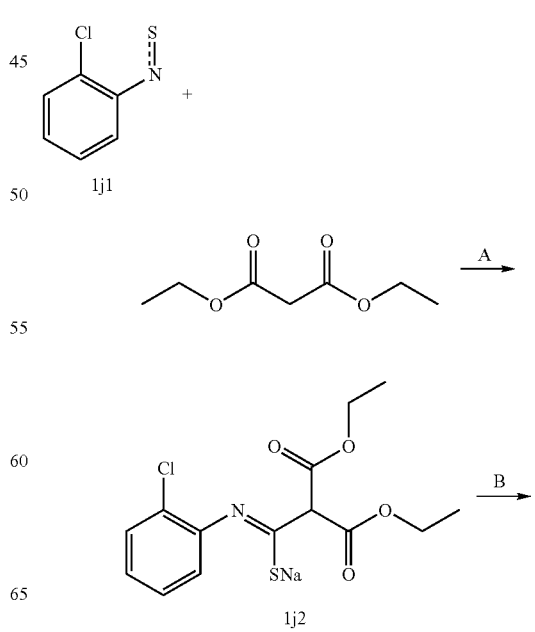

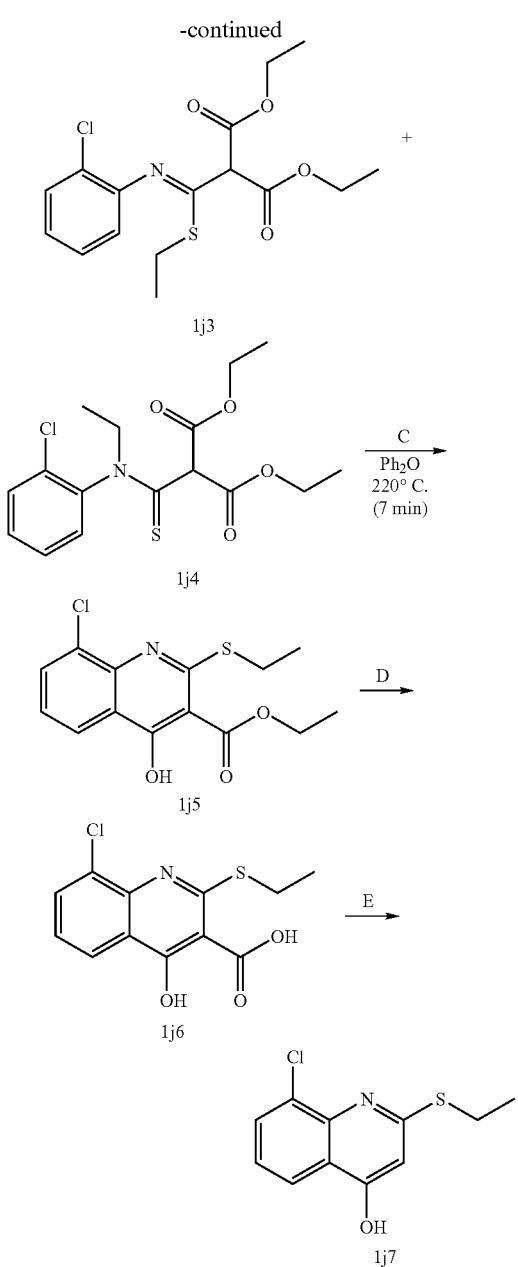

mixture of ether/hexanes (1:1, 3×150 mL). The combined organic fractions were washed with water (2×), dried over MgSO$_4$, filtered and concentrated to afford approximately a 1:1 mixture of 1j3 and 1j4 (S versus N alkylation)(6.1 g, 100%) as a yellow oil. This mixture can be used in the following step since only the S-alkylated analog will cyclize.

Step C: In a pre-heated sand bath (350° C.) a solution of compounds 1j3 and 1j4 (6.1 g, 17.05 mmol, 1 eq.) in diphenyl ether (60 mL) was heated until the internal temperature reached 220° C., which was maintained for 7 minutes. The solution was cooled to RT and the mixture loaded directly on a silica gel column, being eluted first with hexanes (1 L) to remove the diphenyl ether, and then 3% EtOAc/hexanes to afford the desired quinoline 1j5 (2.76 g, 52%) as a pale yellow solid.

Step D: To a solution of quinoline 1j5 (2.76 g crude; 8.85 mmol; 1 eq) in THF (10 mL) and methanol (10 mL) at RT was added 1N NaOH (45 mL; 45 mmol; 5.1 eq). The reaction was allowed to stir at reflux (85° C.) for 24 h (monitored by HPLC). The mixture was acidified using 4N HCl and extracted using methylene chloride (3×). The organic fractions were dried over MgSO$_4$, filtered and concentrated to afford the quinoline acid 1j6 (2.43 g, 97%) as a pale yellow solid. MS: (M+H)$^+$; 284. This material was used as is for the following reaction.

Step E: Compound 1j6 (2.43 g, 8.56 mmol) was added to diphenyl ether (20 mL) and the heterogeneous mixture was heated to 250° C. for 12 minutes before being cooled. The mixture was directly transferred to a silica gel column and eluted first with hexanes (to remove diphenyl ether), and then with 30% and 50% EtOAc/hexanes (R$_f$=0.48 in EtOAC/hexanes (1:1)). Evaporation of the solvent afforded the desired 2-ethylthio-8-chloro-4-hydroxyquinoline 1j7 (1.25 g, 61%) as a pale yellow solid. MS: (M+H)$^+$; 240, HPLC homogeneity=99%.

Example 1K

Synthesis of P2 Moiety
8-chloro-2-ethoxy-4-hydroxy-1,7-naphthyridine
(1k3)

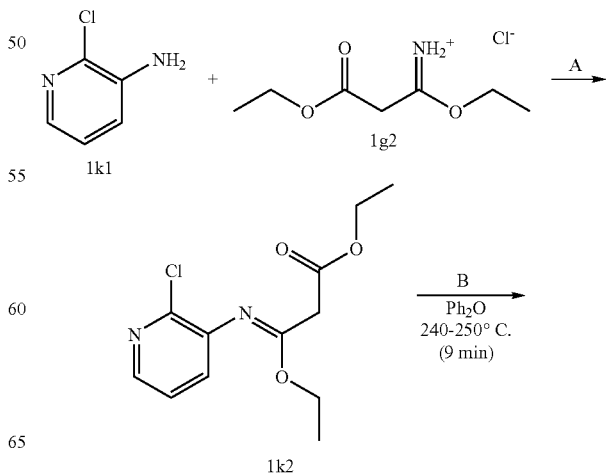

Step A: To THF (30 mL) was added sodium hydride (60% in oil, 920 mg, 23 mmol, 1.2 eq) before being cooled to 0° C. Diethyl malonate (2.91 mL, 19.15 mmol, 1.0 eq) was then added dropwise (gas evolution) and this solution was allowed to warm to RT and was stirred for 1 hr. This mixture was cooled down to 0° C. before the addition of 2-chlorophenyl isothiocyanate 1j1 (2.5 mL, 19.15 mmol, 1.0 eq). The resulting mixture was again allowed to warm to RT for 3 h until the starting material was consumed. The orange solution was concentrated down and dried in vacuo to afford the sodium salt adduct 1j2 (6.73 g, 100%) as an orange crystalline solid. This material was used as is for subsequent steps.

Step B: A solution of adduct 1j2 (6.0 g, 17.06 mmol, 1 eq) in DMF (50 mL) was cooled down to −45° C. Ethyl iodide (1.64 mL, 20.5 mmol, 1.2 eq) was then slowly added and the solution was stirred at −45° C. for 2 h and then at RT (16 h). Water was added and the mixture was extracted twice with a

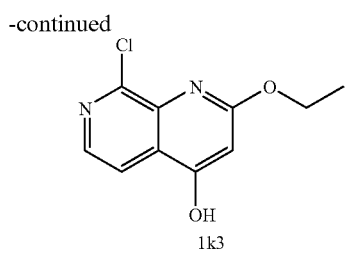

Step A: To 3-amino-2-chloro-pyridine 1k1 (964 mg, 7.5 mmol, 1 eq) was added imidate 1g2 (1.47 g, 7.5 mmol, 1 eq) in ethanol (15 mL) under a $N_2$ atmosphere. The mixture was stirred at RT for 24 h at which point the reaction was concentrated and purified directly on a silica gel column (eluent: EtOAc/Hexanes (1:9)) to afford adduct 1k2 (1.54 g, 76%) as a clear oil.

Step B: Adduct 1k2 (200 mg, 0.74 mmol) was dissolved in diphenyl ether (5 mL) and placed in a pre-heated sand bath (300° C.). The internal temperature was monitored and allowed to stay between 210° C.-225° C. for 7 minutes. The mixture was directly loaded on a silica gel column and eluted with hexanes to remove diphenyl ether, followed by a gradient of 30% to 50% EtOAc/hexanes: (Rf=0.48 in 1:1 EtOAc/hexanes). Concentration and drying in vacuo afforded the desired napthyridine 1k3 (32 mg, 19%) as a white solid. MS: 225 (M+H)$^+$.

Example 1L

Synthesis of P2 Moiety
2-ethoxy-8-methylthio-4-hydroxyquinoline (1l3)

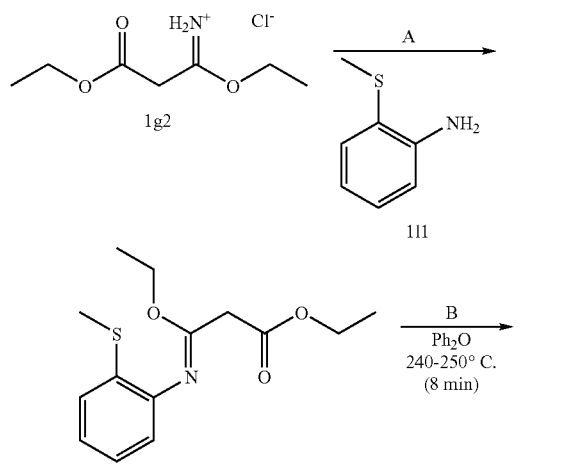

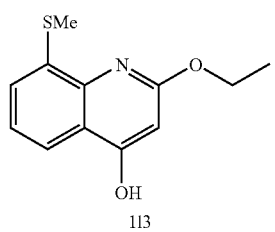

Step A: The imidate salt 1g2 (1.4 g, 7.2 mmol, 1 eq) was combined with 2-(methylthio)aniline 1l1 (0.96 g, 7.50 mmol, 1 eq.) in ethanol (15 mL) under an $N_2$ atmosphere. The reaction mixture was stirred at RT (1 h) and monitored by HPLC. The reaction mixture was concentrated and then ether was added and the mixture filtered. The solids were washed with ether and the combined ether washes concentrated in vacuo. The resulting adduct 1l2 was obtained as a yellow oil (1.66 g, 82%) and used as is in the next step. MS electrospray: (M+H)$^+$; 282 and (M−H)$^-$; 280.

Step B: The condensation product 1l2 (1.66 g, 5.90 mmol) was dissolved in diphenyl ether (10 mL) and placed in a sand bath (300° C.). The internal temperature was monitored and allowed to stay between 240-250° C. for 10 minutes. The mixture was cooled and then directly loaded on a silica gel column and eluted first with hexanes, then with 30% EtOAc/Hexanes and finally 50% EtOAc/hexanes. The product was concentrated and dried in vacuo to give the corresponding 4-hydroxyquinoline derivative 1l3 as a yellow solid (0.735 g, 53%). MS electrospray: (M+H)$^+$; 236 and (M−H)$^-$; 234.

Example 1M

Synthesis of P2 Moiety
2-ethoxy-7-methoxy-8-methyl-4-hydroxyquinoline (1m3)

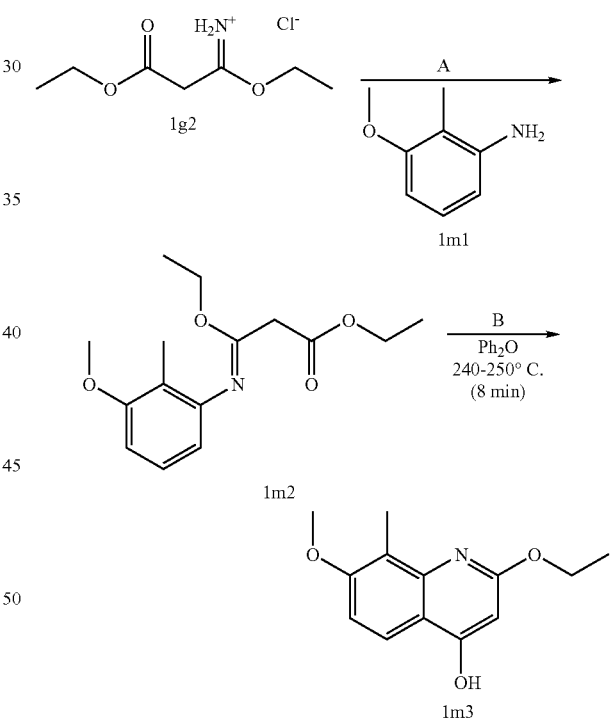

Step A: The imidate salt 1g2 (1.5 g, 7.65 mmol) was combined with 2-methyl-3-aminoanisole 1 ml (1.05 g, 7.65 mmol, 1 eq.) in ethanol (15 mL) under an $N_2$ atmosphere. The reaction mixture was stirred at RT (24 h) and monitored by HPLC. The reaction mixture was concentrated and then ether was added and the mixture filtered. The solids were washed with ether and the combined ether washes concentrated in vacuo. The resulting adduct 1m2 was purified by chromatography (SiO$_2$, 15% EtOAc/hexanes) to obtain as a yellow oil (2.11 g, 99%). MS electrospray: (M+H)$^+$; 280 and (M−H)$^-$; 278.

Step B: The condensation product 1m2 (2.1 g, 7.52 mmol) was dissolved in diphenyl ether (10 mL) and placed in a sand bath (300° C.). The internal temperature was monitored and allowed to stay between 240-250° C. for 10 minutes. The mixture was cooled and then directly loaded on a silica gel column and eluted first with hexanes, then with 30% EtOAc/Hexanes and finally 50% EtOAc/hexanes. The product was concentrated and dried in vacuo to give the corresponding 4-hydroxyquinoline derivative 1m3 as a yellow oil which solidified upon standing to a yellow solid (1.09 g, 62%). MS electrospray: (M+H)+; 233.4 and (M–H)−; 231.9.

Example 1N

Synthesis of P2 Building Block
2-ethoxy-8-methoxy-4-hydroxyquinoline (1n3)

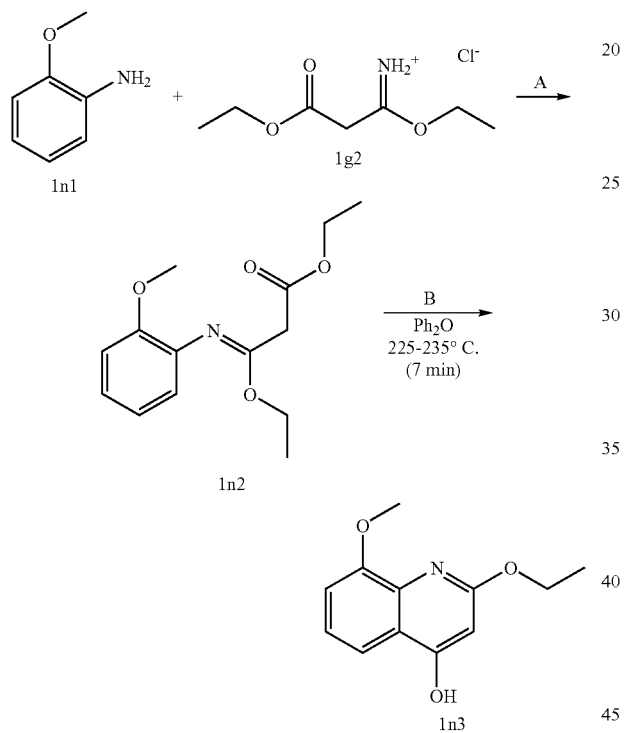

Step A and B: Beginning with ortho-anisidine 1n1 and following the same protocol as outlined in previous examples, the desired 8-methoxyquinoline derivative 1n3 was obtained in 38% overall yield as a pale yellow solid. MS: 220 (M+H)+.

Example 1O

Synthesis of P2 Building Block
8-bromo-2-ethoxy-4-hydroxy 7-methoxy-quinoline (1o2)

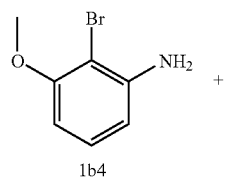

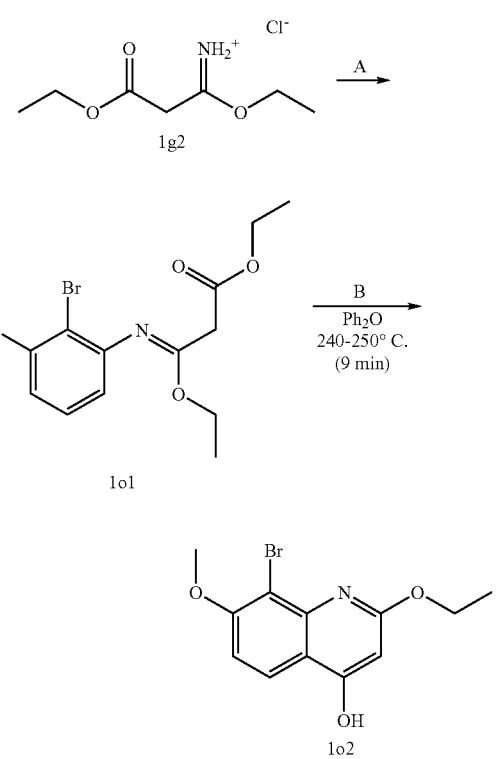

Step A: To 2-bromo-3-aminoanisole 1b4 (750 mg, 3.7 mmol, 1 eq) was added imidate 1g2 (0.73 g, 3.7 mmol, 1 eq) in ethanol (7 mL) under a N$_2$ atmosphere. The mixture was stirred at RT for 24 h at which point the reaction was concentrated and purified directly on a silica gel column (eluent: EtOAc/Hexanes (1:9)) to afford adduct 1o1 (1.12 g, 88%) as a pale yellow oil. MS: 344 (M+H)+ and 346 (MH+2)+.

Step B: Adduct 1o1 (1.12 g, 3.25 mmol) was dissolved in diphenyl ether (10 mL) and placed in a pre-heated sand bath (300° C.). The internal temperature was monitored and allowed to stay between 240° C.-250° C. for 8 minutes. The mixture was directly loaded on a silica gel column and eluted with hexanes to remove diphenyl ether, followed by a gradient of 30% to 50% EtOAc/hexanes: (R$_f$=0.25 in 1:1 EtOAc/hexanes). Concentration and drying in vacuo afforded the desired quinoline 1o2 (734 mg, 76%) as a white solid. MS: 298 (M+H)+ and 300 (MH+2)+.

Example 1P

Synthesis of P2 Moiety
5-ethoxy-thieno[3.2-b]pyridin-7-ol (1p3)

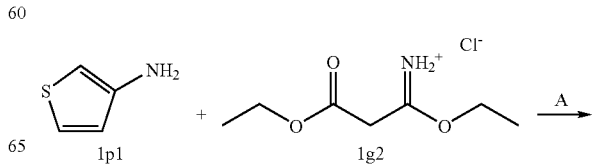

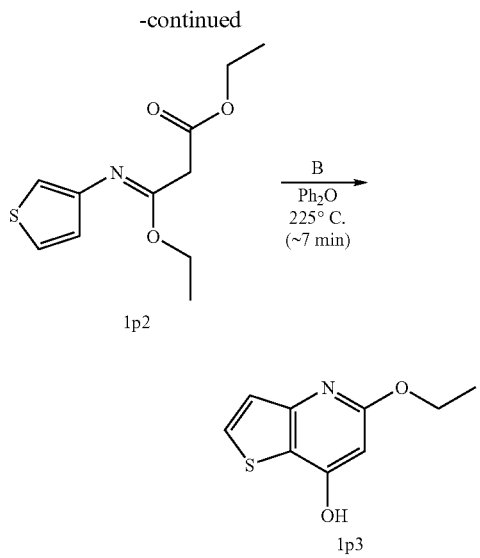

Step A: To available thiophen-3-ylamine 1p1 (0.50 g, 5.04 mmol) was added imidate 1g2 (1.08 g, 5.5 mmol) in ethanol (10 mL) under a N₂ atmosphere. The mixture was stirred at RT for 3 h at which point the reaction was concentrated. To the residue was added ether, and the suspension filtered and washed with ether to afford adduct 1p2 (1.0 g, 82%). This material was sufficiently clean to be used in the subsequent step. MS: 242.1 (MH)⁺.

Step B: Adduct 1p2 (1.0 g, 4.14 mmol) was dissolved in diphenyl ether (5 mL) and placed in a pre-heated sand bath (300° C.). The internal temperature was monitored and allowed to stay between 210° C.-225° C. for 7 minutes. The mixture was directly loaded on a silica gel column and eluted with hexanes to remove diphenyl ether, followed by a gradient of 30% EtOAc/hexane to neat EtOAc. Concentration and drying in vacuo afforded the desired thieno[3.2-b]pyridinol 1p3 (200 mg, 25%) as a brown solid. MS: 196 (MH)⁺.

Example 1Q

General Synthesis of P2 Moiety
6-substituted-2H-isoquinoline-1-one (1q3)

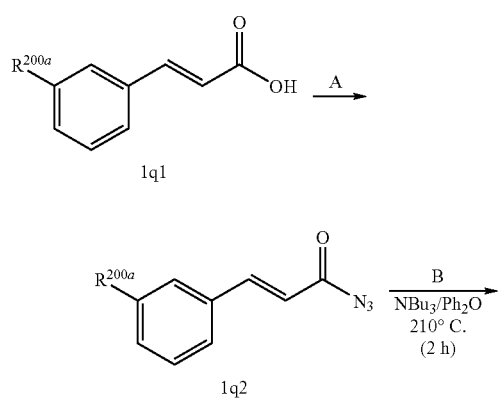

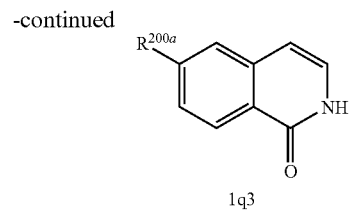

Briefly, 6-substituted isoquinolones, wherein $R^{200a}$ is $R^{200}$ as defined herein, can be made from 3-substituted cinnamic acid derivatives by first activation with a chloroformate in base followed by treatment with an azide source. The resulting acyl azide can undergo a Curtius rearrangement followed by thermal cyclization to afford the appropriately substituted isoquinolones. As described here, the cinnamic acid can be differentially substituted.

Example 1R

Preparation of 6-methoxy-2h-isoquinoline-1-one (1r3)

In general, the isoquinolines were prepared according to the following reference; Tetrahedron, 2002, 58, 5761-5766.

Step A: The 3-methoxycinnamic acid 1r1 (2.5 g, 14.03 mmol) was dissolved in acetone (40 mL) and treated with triethylamine (3.94 mL, 28.06 mmol). The solution was cooled to 0° C. and then treated dropwise with ethyl chloroformate (2.0 mL, 21 mmol). A white precipitate immediately formed upon addition of each drop. The solution was stirred for 1 h (with a suspension) before being treated with sodium azide (0.91 g, 14.03 mmol) in 10 mL of H₂O dropwise over 30 min. The mixture was allowed to stir at rt 16 h before being diluted with water (20 mL) and the volatiles removed in vacuo. The aqueous phase was extracted with toluene (2×60 mL), dried over MgSO₄, and then filtered and concentrated to give a yellow oil (2.23 g) which solidified to a yellow solid 1r2 upon standing.

Step B: The diphenyl ether (10 mL) and tributylamine (7 mL) were heated in a sand bath to 190° C. before the dropwise addition of the acyl azide 1r2 (behind an explosion shield) in toluene (5 mL) over several minutes. The toluene distilled off and the temperature was raised to 210° C. for 2 h. After cooling, the precipitated product was collected by filtration and washed with hexanes to give the desired isoquinoline 1r3 (0.47 g, 19%). MS (electrospray); (M+H)$^+$; 176 and (M−H)$^−$; 174. $^1$H NMR (400 MHz, DMSO-$d_6$) δ 11.05 (bs, 1H), 8.07 (d, J=8.8 Hz, 1H), 7.16-7.09 (m, 2H), 7.04 (dd, J=9, 2.4 Hz, 1H), 6.47 (d, J=7.0 Hz, 1H), 3.86 (s, 3H).

Example 1S

Synthesis of P2 Moiety
4-hydroxy-7-methoxy-8-methyl-quinoline (1s2)

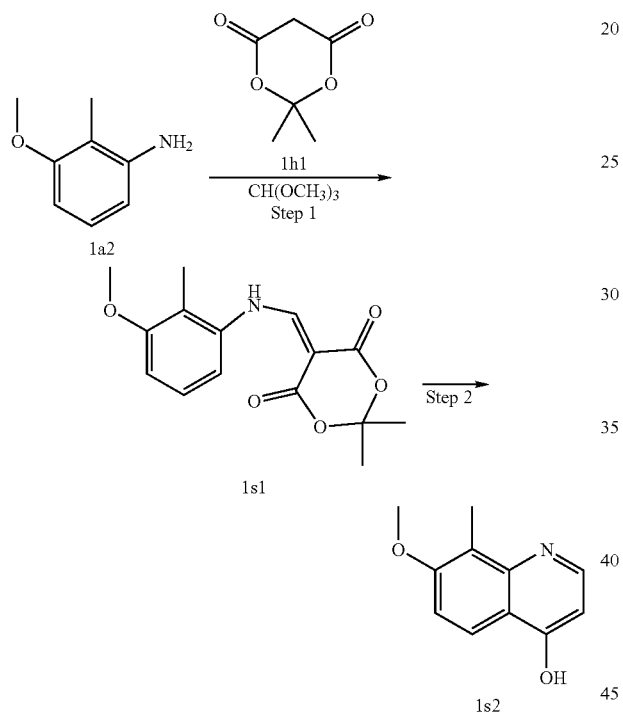

Step 1: To aniline 1a2 (Example 1A) (504 mg; 3.67 mmol) dissolved in anhydrous acetonitrile (5.0 mL) was added Meldrum's acid 1h1 (582.4 mg; 4.04 mmol) followed by trimethyl orthoformate (482.3 μL; 4.41 mmol). The resulting brown solution was refluxed for 2 hours and the reaction judged complete by HPLC and TLC (Hexane:EtOAc; 6:4) Note: With the onset of heat a grey precipitate formed rendering stirring difficult. Therefore, an additional 5 mL of acetonitrile was added to eventually obtain a clear yellow solution within the first hour. The reaction mixture was cooled to RT and evaporated to dryness. The crude yellow solid was dissolved in a minimum amount of boiling MeOH and water slowly added till just cloudy to precipitate the product which was filtered, rinsed with water and dried to provide a light tan crystalline solid 1s1 (845.5 mg; 79% yield). NMR (CDCl$_3$, 400 MHz) and MS 290.1 confirmed the product. Homogeneity by HPLC (TFA) @ 220 nm:99%.

Step 2: A three-neck flask containing diphenyl ether (1.9 mL; 11.75 mmol) was placed into a preheated sand bath heated to ~300° C. and the sand bath allowed to slowly heat further to ~330° C. so as the internal temperature was between 245-250° C. The aniline derivative 1s1 was added portion-wise (immediately seeing gas evolution) at a rate as to maintain the internal temperature at 240-245° C. (addition time 5-10 min). Once addition was complete, the yellow solution was maintained at 245-250° C. for 20 minutes. TLC (Hexane:EtOAc 6:4) indicated the consumption of starting material, however, the reaction mixture was left another 20 minutes to ensure complete intermediate decarboxylation. The mixture was worked-up by cooling the brownish solution to RT at which time a solid precipitated. The material was triturated with ether, filtered, rinsed and dried to provide the quinoline product 1s2 as a tan brown solid (216.7 mg; 83%). NMR (DMSO, 400 MHz) indicates the product to be mainly in the keto tautomer form. MS 187.9, 190.0 confirmed the product. Homogeneity by HPLC (TFA) @ 220 nm:97%.

Example 1T

Synthesis of P2 Moiety
4-hydroxy-8-methylthio-quinoline (1t3)

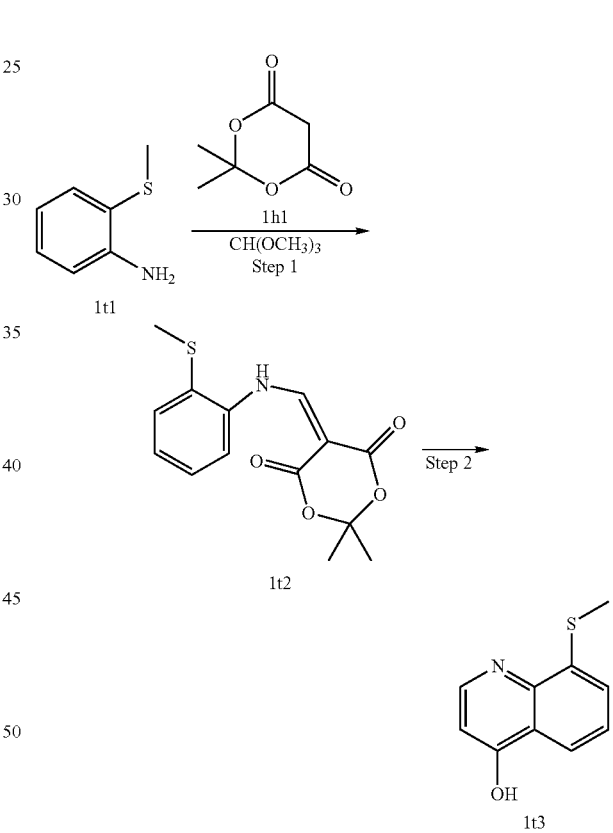

Step 1: 2-Methylthioaniline 1t1 (2 g, 14.36 mmol) was dissolved in anhydrous acetonitrile (50 mL) at RT. Meldrum's acid 1h1 (2.48 g, 17.3 mmol) was then added, followed by trimethyl orthoformate (2 mL, 18.6 mmol). The resulting mixture was then heated to reflux (95° C.) for 2 h. The solution was cooled to rt, and evaporated to dryness to obtained an orange solid that was triturated with MeOH, filtered and to afford 3.33 g of a pale yellow solid (79%) 1t2, which was used as such for the next step.

Step 2: In a pre-heated sand bath (300-350° C.), diphenyl ether (5 mL) was heated until the internal temperature reached 220° C., then 1t2 (3.34 g, 1.14 mmol) was added portionwise over a 4 min period (gas evolution). The same temperature was maintained for another 5 min after which the solution was cooled down. Ether was added. After stirring for 12 h, a beige solid precipitated, filtered and washed with diethyl ether, dried under vacuum to afford 669 mg of a beige solid 1t3 (30%). $^1$H NMR (400 MHz, DMSO-d$_6$) 11.06 (s, 1H), 8.00 (d, J=8 Hz, 1H), 7.81 (t, J=7.2 Hz, J=13.7 Hz, 1H), 7.75 (dd, J=1.0 Hz, J=7.2 Hz, 1H), 7.30 (t, J=7.8 Hz, J=15.5 Hz, 1H), 6.08 (d, J=7.4 Hz, 1H), 2.52 (s, 3H). MS (ESI) M+H=191.9, M−H=189.9

Synthesis of P1' Fragments

Example 2A

Synthesis of P1 Fragment Sulfamide 2A3

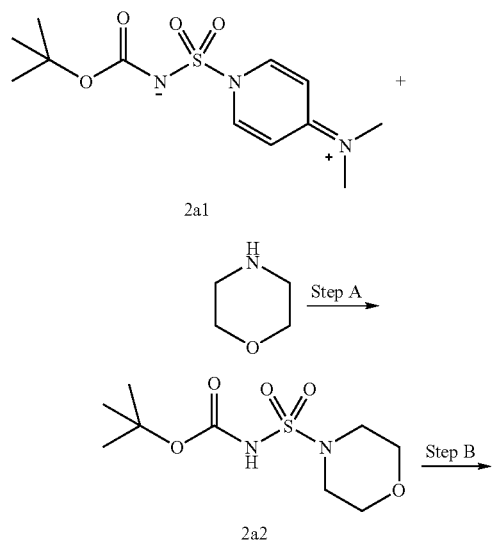

Step 1: Reagent 2a1 (0.3 g, 0.99 mmol) [prepared according to Winum, J-Y; Toupet, L; Barragan, V; Dewynter, G; Montero, J.-L., Org. Lett., 14(3), 2241-2243 (2001)] was suspended in CH$_2$Cl$_2$ before morpholine (0.086 mL, 0.99 mmol) was added and stirred for 5 h. The reaction was followed by TLC. On completion the reaction mixture was directly adsorbed on the silica gel and eluted the product with 6% MeOH in CHCl$_3$ to afford 0.258 g (98%) of compound 2a2 as a white solid.

Step 2: Compound 2a2 (0.150 g, 0.56 mmol) was dissolved in CH$_2$Cl$_2$ (5 mL) and treated with TFA (1 mL). The reaction was stirred for 4 h and monitored by TLC. Upon completion, the solvent was evaporated and the residue directly adsorbed on the silica gel and eluted with 5% MeOH in CHCl$_3$ to afford 0.075 g (80.2%) of compound 2a3 as a white solid.

Example 2B

Synthesis of P1' Fragment Sulfamide (2B2)

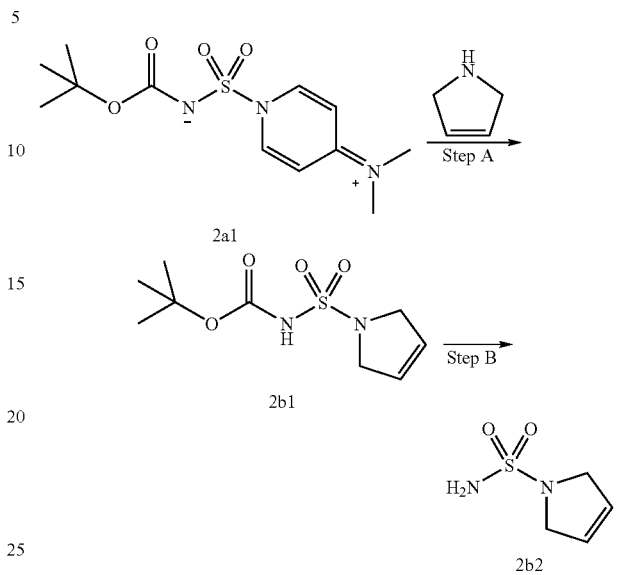

Step A: Reagent 2a1 (1.5 g, 4.98 mmol) was suspended in 12 mL of CH$_2$Cl$_2$ before the pyrroline (0.40 mL, 5.22 mmol, 1.05 equiv.) was added and stirred overnight. On completion, the reaction mixture was directly adsorbed on the silica gel and eluted the product with 1% AcOEt in CH$_2$Cl$_2$ to afford 0.919 g (74%) of compound 2b1 as a white solid.

Step B: Compound 2b1 (0.919 g, 3.70 mmol) was dissolved in 10 mL of CH$_2$Cl$_2$ and treated with TFA (2 mL). The reaction was stirred at room temperature for 4 h. The solvent was then evaporated in vacuo, the residue was dried under vacuum to afford 0.565 g (quantitative) of compound 2b2 as a beige solid.

Example 2C

Synthesis of P1' Fragment Sulfamide (2c2)

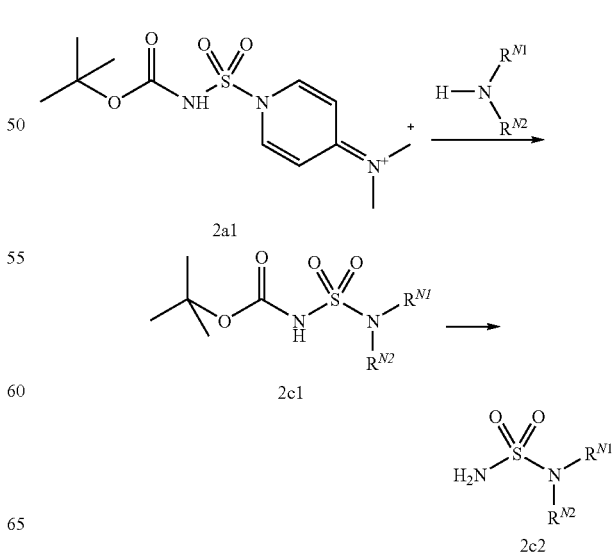

Step A: Note: the reaction was performed on a solid phase synthesizer (Advanced Chemtech ACT 396), using the 96-wells block. The starting material 2a1 (45.2 mg, 0.15 mmol) was weighed in 96 Eppendorf vials and 96 different amines (0.18 mmol, 1.2 equiv.) were weighed and placed in separate Eppendorf vials. Each well of the reaction block were filled with 1.2 mL of 1,2-dichloroethane and the starting material 2a1 and the various amines were added. The reaction mixtures were shaken for 12 h in the case of aliphatic amines and for 36 h in the case of aniline derivatives. After the required stirring time, PS-trisamine resin was added to each well (Argonaut Technologies, 3.42 mmol/g loading, 0.63 mmol, 0.184 g, 4.2 equiv.). After shaking for 3 h, the solvent was drained and the resins were washed successively with $CH_2Cl_2$ (3×1 mL), MeOH (3×1 mL) and $CH_2Cl_2$ (3×1 mL). In each well was then added $CH_2Cl_2$ (1.2 mL) and AcOH (100 µl) and the shaking was maintained for 30 minutes. The solutions were drained in pre-tarred 2 drams vials to recover the filtrate and each resins were washed once with $CH_2Cl_2$ (1.2 mL) and MeOH (1.2 mL). The filtrates were recovered in the same 2-dram vials as before. The vials were finally placed on a vacuum centrifuge to remove the solvent and the desired products 2c1 were obtained in 41-54% yields (18-27 mg of product). Those compounds were used as is in the next step.

Step B: The products 2c1 in 2-dram vials were dissolved in 1,2-dichloroethane (0.5 mL) and TFA (0.5 mL) and the vials were shaken on an orbital shaker for 1.5 h. The volatiles were removed on a vacuum centrifuge to afford the desired products 2c2 in yields ranging from 71% to quantitative (12-20 mg of product). Those compounds were used as is in the next step of synthesis of compounds of formula (I).

Example 2D

Synthesis of P1' Fragment
1-methylcyclopropylsulfonamide (2d7)

Cyclopropanesulfonamide can be prepared by amination of cyclopropanesulfonyl chloride, according to the literature reference of J. King et al., *J. Org. Chem.*, 1993, 58, 1128-1135, or as set out below.

Step 1: A dry 3 L 3-neck flask equipped with a magnetic stir bar, addition funnel and argon inlet was flushed with argon, then charged with 3-chloropropanesulfonyl chloride 2d1 (100.48 g, 0.57 mol, 1.0 eq). Anhydrous dichloromethane (900 mL) was transferred into the flask via cannula, the mixture was cooled in an ice/water bath and tert-butylamine (72 mL, 0.68 mol, 1.2 eq) was added. The mixture was stirred 15 minutes then a solution of triethylamine (158 mL, 1.13 mol. 2.0 eq) in anhydrous dichloromethane (100 mL) was added dropwise over 45 minutes and stirring was continued for 1 h. The mixture was diluted with dichloromethane (500 mL) and washed with 1N HCl (3×400 mL) and brine. The organic layer was dried over sodium sulfate, filtered and evaporated to dryness to give compound 2d2 as an orange-beige solid (107.04 g, 88% yield). $^1$H NMR ($CDCl_3$, 400 MHz): δ 4.46 (s, 1H), 3.71 (tr, 2H), 3.25 (tr, 2H), 2.31 (m, 2H), 1.41 (s, 9H).

Step 2: A dry 5 L 3-neck flask equipped with a magnetic stir bar, argon inlet and 2 addition funnels was flushed with argon and anhydrous THF (1.5 L) was transferred into the flask via cannula and cooled to −78° C. Compound 2d2 (96.73 g, 0.453 mol. 1.0 eq) was dissolved in anhydrous THF (390 mL) and the solution was transferred into one of the addition funnels. n-Butyllithium solution (2.5 M in hexanes, 390 mL, 0.975 mol. 2.15 eq) was transferred to the other addition funnel and the solutions in the addition funnels were added to the flask simultaneously over 4 hours. When addition was complete, the mixture was allowed to warm to room temperature. Once the internal temperature reached ~0° C., the reaction was quenched by dropwise addition of saturated $NH_4Cl$ solution (200 mL). The THF was removed under vacuum and the residue was diluted with $CH_2Cl_2$ (2 L) and water (1 L). The layers were separated and the organic layer was washed with water (2×1 L) and brine (800 mL), dried over sodium sulfate, filtered and evaporated to dryness. Compound 2d3 was

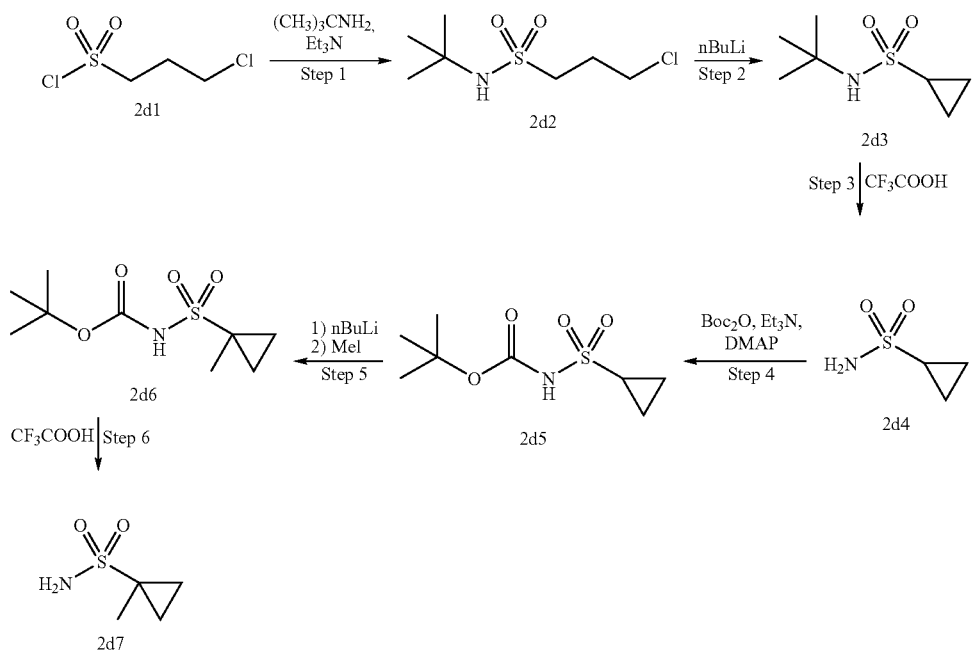

obtained as an orange-beige solid (77.32 g, 96% yield). $^1$H NMR (CDCl$_3$, 400 MHz): δ 4.25 (s, 1H), 2.48 (m, 1H), 1.42 (s, 9H), 1.19 (m), 1.01 (m).

Step 3: A 2 L flask equipped with a magnetic stir bar and condenser was charged with Compound 2d3 (82.53 g, 0.466 mol, 1.0 eq), dichloromethane (400 mL) and trifluoroacetic acid (460 mL, 5.97 mol, 13 eq). The mixture was heated to reflux for 2 h, allowed to cool, and evaporated and co-evaporated several times with CH$_2$Cl$_2$ to remove most of the TFA. The crude product was dissolved in 95:5 CH$_2$Cl$_2$:MeOH and NH$_4$OH and was purified by silica gel column chromatography (94:5:1 CH$_2$Cl$_2$:MeOH:NH$_4$OH). Compound 2d4 was obtained as a beige solid (46.38 g, 78% yield). $^1$H NMR (DMSO-d$_6$, 400 MHz): δ 6.79 (s, 2H), 2.54 (1H, under DMSO peak), 0.92 (4H).

Step 4: To the solid cyclopropanesulfonamide 2d4 (1.51 g; 12.46 mmol) was added in sequence: di-t-butyl-dicarbonate (3.26 g; 14.95 mmol) dissolved in anhydrous dichloromethane (15 mL), triethylamine (2.6 mL; 18.65 mmol) and dimethylaminopyridine (76 mg; 0.622 mmol). The resulting solution was stirred at room temperature overnight and subsequently evaporated to near dryness. The residue was diluted with EtOAc, washed with 1N aq. HCl (3×) and brine (1×), dried (MgSO$_4$), filtered and evaporated to dryness to provide the Boc-cyclopropylsulfonamide product 2d5 as a white solid (2.6 g; 94%).

Step 5: To a cooled solution (−78° C.) of the Boc-cyclopropanesulfonamide 2d5 (500 mg; 2.26 mmol) in anhydrous THF (15 mL) was added dropwise n-BuLi (2.1 mL; 5.20 mmol) and the mixture was allowed to stir 1 h at −78° C. Two portions of methyl iodide (each 280 µL; 4.52 mmol) were added with a one hour interval and the reaction mixture was allowed to warm slowly to RT and stir at RT overnight. The reaction mixture was adjusted to pH 3 with 1N aq. HCl and the product was extracted with EtOAc (3×). The combined EtOAc extracts were washed with brine (1×), dried (MgSO$_4$), filtered and evaporated to dryness to provide the crude alkylated product 2d6 as a light yellow oil. The crude material was purified by flash chromatography over silica gel with hexane:EtOAc (9:1) as eluent to provide pure product as a yellow oil (151.8 mg; 29%).

Step 6: To a solution of the Boc-1-methylcyclopropanesulfonamide 2d6 (151.8 mg: 0.65 mmol) in dichloromethane (6 mL) was added trifluoroacetic acid (6 mL) and the mixture allowed to stir at RT for 3.5 h. Evaporation to dryness under high vacuum provided the deprotected material 2d7 as an off-white wax like solid (79.1 mg, 91%). $^1$H NMR (CDCl$_3$, 400 MHz): δ 4.56 (s, 2H), 1.58 (s, 3H), 1.43-1.38 (m, 2H), 0.85-0.80 (2H).

Synthesis of P1-P1' Fragments

Example 2E

Synthesis of P1-P1' Fragment (2e3)

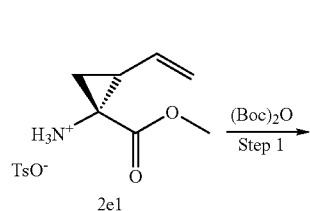

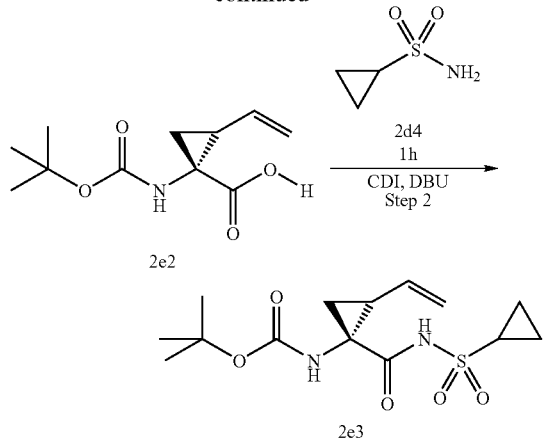

Step 1:

To a solution of compound 2e1 (12 g, 38.29 mmol) in a mixture of THF (50 mL) and 1N aq. NaOH (85 mL, 85.00 mmol) was added Boc anhydride (10 g, 45.95 mmol). The reaction mixture was stirred at RT for 4 days. The pH was periodically adjusted to 9 by adding more NaOH. The THF was then removed in vacuo and the aqueous layer was washed with ether (3×150 mL) and then cooled to 0° C. for the slow addition of 1N aq. HCl until pH 3-4 was obtained. The aqueous layer was then extracted with EtOAc (3×150 mL) and the combined organic extracts were successively washed with water (3×100 mL) and brine. After drying over MgSO$_4$, filtration and concentration, 5.16 g of the desired Boc-protected intermediate 2e2 was isolated.

Step 2:

To a solution of acid 2e2 (567 mg, 2.49 mmol), in THF (20 mL), was added CDI (515 mg, 3.17 mmol). The resulting solution was stirred for 30 min, refluxed for 30 min and allowed to cool down to RT. Cyclopropylsulfonamide 2d4 (455 mg, 3.76 mmol) was added followed by the addition of DBU (0.75 mL, 5.02 mmol) and the reaction was stirred 12 h. The THF was removed in vacuo and the residue was diluted with EtOAc, washed with 1M HCl (2×100 mL) and brine, dried (MgSO$_4$) and purified by flash chromatography (elution conditions: 70:30 hexane/EtOAc) to afford 682 mg (82%) of compound 2e3 as a white solid.

Synthesis of Capping Groups

Example 3A

Synthesis of Capping Group 3a3

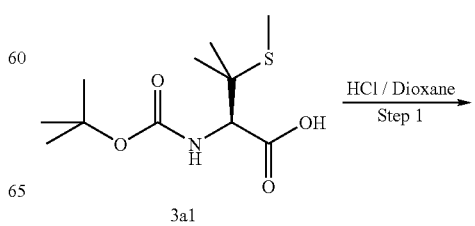

-continued

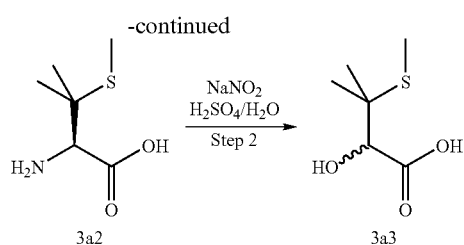

Step 1:

An aqueous solution of the dicyclohexylamine salt of compound 3a1 (0.5 g, 1.12 mmol) was adjusted to pH 2 by addition of 1M HCl and the resulting aqueous phase was extracted twice with EtOAc. The EtOAc phase was dried (MgSO$_4$), filtered and concentrated) to give 290 mg (1.10 mmol, 98%) of the free acid. The free acid was dissolved in 4M HCl/dioxane (5 mL) and the mixture was stirred at room temperature for 1 hour. The solvent was evaporated and the residue 3a2 was dried under vacuum and used as is in the next step.

Step 2:

The amino acid salt 3a2 (1.10 mmol), in an 0.5M aqueous solution of H$_2$SO$_4$ (4.5 mL), was cooled to 0° C. and a solution of NaNO$_2$ (459 mg, 6.6 mmol, 6 equiv./1.5 mL H$_2$O) was added slowly over a period of 3 hours. The ice bath was removed and the resulting solution was stirred overnight at room temperature. The reaction mixture was extracted twice with EtOAc, dried (MgSO$_4$), and evaporated to give the crude product 3a3 as a yellow oil (160 mg, 0.97 mmol, 88%).

Example 3B

Synthesis of Capping Group 3b4

Step 1:

A solution of ethyl cyanoacetate (17.7 mL, 166.3 mmol), cyclohexanone (20.7 mL, 199.7 mmol, 1.2 equiv.), ammonium acetate (1.28 g, 16.6 mmol, 0.1 equiv.) and acetic acid (2 g, 33.3 mmol, 0.2 equiv.) in benzene (17 mL) was heated under reflux for a period of 4 hours, with removal of water by means of a Dean-Stark trap. The solvent was removed in vacuo and the residue was diluted with EtOAc, and washed with aqueous NaHCO$_3$. The aqueous phase was extracted 3 times with EtOAc, the organic phases were combined and dried (MgSO$_4$), and the solvent was evaporated in vacuo. The residue was purified by flash chromatography (eluant: 95:5 Hexanes/EtOAc) to give 25.7 g (133.2 mmol, 80%) of the desired compound 3b1.

Step 2:

To a solution of MeMgBr (3.0 N in ether; 40 mL, 120.0 mmol, 5.0 equiv.) was added dropwise a solution of compound 3b1 (4.6 g, 23.8 mmol) in 15 mL of anhydrous ether. The resulting grey solution was stirred 3 hours at room temperature, then poured onto ice. The aqueous phase was acidified with HCl (10 N) before extraction 3 times with ether. The combined organic phases were dried (MgSO$_4$) and the solvent evaporated. The residue was purified by flash chromatography (eluant: 95:5 Hexanes/EtOAc) to provide 4.1 g (19.6 mmol, 80%) of compound 3b2.

Step 3:

A solution of compound 3b2 (1 g, 5.0 mmol) in 10 mL of a mixture of KOH (3 g) and ethylene glycol (10 mL), was heated at reflux (~180-190° C.) for 10 hours. The reaction mixture was diluted with water and extracted twice with ether. The aqueous phase was acidified by addition of HCl (10%) and extracted with 3 portions of EtOAc. The combined organic phase was dried over MgSO$_4$ and concentrated in vacuo. The crude material was heated to 150° C. for 1.5 h, then was diluted with NaOH (1M) and extracted twice with ether. The aqueous phase was acidified by addition of HCl (1M) and extracted with 3 portions of EtOAc, dried (MgSO$_4$), and concentrated to give 0.56 g (3.6 mmol, 71%) of the crude material 3b3.

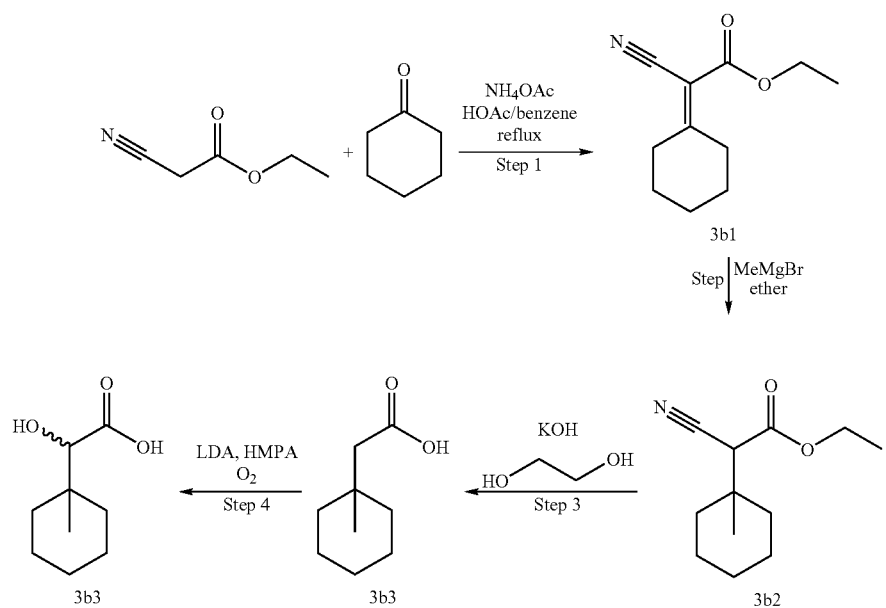

Step 4:

A solution of dry diisopropylamine (0.4 mL, 2.85 mmol, 2.23 equiv.) in dry THF (5 mL) was cooled to 0° C. and BuLi (0.8 M in hexanes; 3.5 mL, 2.80 mmol, 2.18 equiv.) was added dropwise. After 30 minutes, the solution was cooled to −30° C. and a mixture of the acid 3b3 (200 mg, 1.28 mmol, 1 equiv.) and dry HMPA (0.23 mL, 1.32 mmol, 1.03 equiv.) in THF (2.5 mL) was added slowly. The resulting solution was heated to 50° C. for 30 minutes and cooled to room temperature. Gaseous $O_2$ was bubbled into the solution over 40 minutes and the reaction mixture was diluted with 1M HCl and extracted twice with EtOAc. The organic layer was dried ($MgSO_4$) and concentrated to afford 255 mg of the crude material 3b4.

Example 3C

Synthesis of Capping Group 3c1

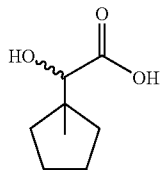

3c1

By following the procedure of Example 3B, but using cyclopentanone in place of cyclohexanone, compound 3c1 was obtained.

Example 3D

Synthesis of Capping Group 3d5 temperature and poured into 60 mL of ice-water. The mixture was acidified to pH 2 with 20% aqueous $H_2SO_4$, then extracted with benzene (3×300 mL). The organic extracts were combined, washed with water and brine, and dried over $Na_2SO_4$. After removal of solvents, the oily residue was purified by silica gel chromatography eluting with 5% ethyl acetate in hexanes to yield 10.77 g of the pure compound 3d2.

Step 3:

A solution of KOH (6.58 g, 0.117 mol) in ethylene glycol (42 mL) was added to compound 3d2 (10.76 g, 0.0587 mol). The mixture was heated to reflux for 3 hours, cooled, diluted with water (50 mL), and extracted with ether (3×80 mL). The combined ether layer was washed with brine (1×80 mL) and dried over $Na_2SO_4$. Evaporation of solvents gave 5.43 g of the crude nitrile 3d3 (83.2% yield), which was used directly in the next step.

Step 4:

A solution of KOH (10.3 g, 0.156 mol) in ethylene glycol (39 mL) was added to compound 3d3 (5.43 g, 0.0488 mol) and the mixture was heated at reflux for 8 hours. The reaction mixture was cooled to room temperature, diluted with 200 mL of water, and extracted with ether (3×80 mL). The combined extract was washed with brine and dried over $Na_2SO_4$. Evaporation of the solvent gave 4.75 g of the acid 3d4 (74.8% yield), which was used as is in the next step.

Step 5:

A solution of BuLi in hexane (2.5 M, 35.3 mL) was added dropwise to a solution of N,N-diisopropylamine (12.6 mL, 0.0899 mol) in anhydrous THF (70 mL) at 0° C. and the mixture was stirred for 30 minutes. The resulting LDA solution was cooled to −30° C. and a solution of compound 3d4 (4.75 g, 0.0365 mol) and HMPA (6.54 mL, 0.0376 mol) in 35 mL of anhydrous THF was added dropwise. The mixture was heated to 50° C. for 30 minutes, then allowed to cool to room temperature and $O_2$ was bubbled into the mixture for 90

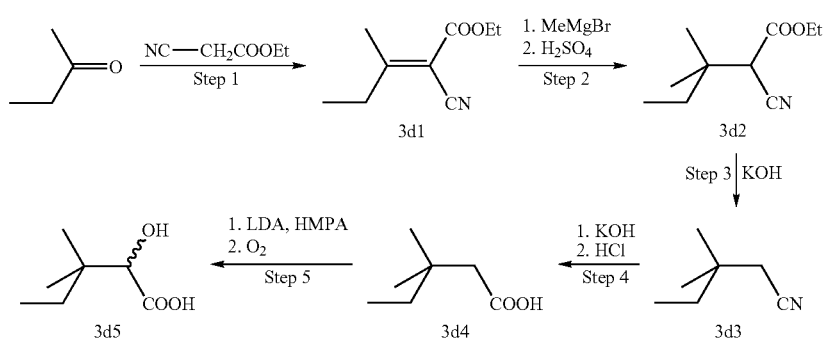

Step 1:

A mixture of β-alanine (0.2 g), ethyl cyanoacetate (50.0 g, 47 mL, 0.44 mol), butanone (38.0 g, 47.5 mL, 0.53 mol), acetic acid (9.0 mL), and benzene (45 mL) was heated to reflux overnight through a Dean-Stark trap, then concentrated under vacuum. The residual oil was distilled under high vacuum to give 42.7 g of the desired compound 3d1.

Step 2:

To a solution of methyl magnesium bromide (3.0 M, 33 mL) was added a solution of compound 3d1 (15.0 g, 89.7 mmol) in 30 mL of anhydrous benzene with stirring. The mixture was heated to reflux for one hour, then cooled to room minutes. The reaction was quenched by the addition of 100 mL of 1M HCl. THF was removed under vacuum and the residue was acidified to pH 1 with concentrated HCl and extracted with ether (3×80 mL). The combined extract was washed with brine and dried over $Na_2SO_4$. Removal of the solvent gave 5.7 g of the crude product which was purified by silica gel chromatography eluting with 0.5-4% of MeOH in dichloromethane to give 3 g of the relatively pure product. Trituration with hexanes gave compound 3d5 as a pure white solid.

$^1$H NMR ($CDCl_3$, 400 MHz): 4.02 (1H, s), 1.66 (1H, m), 1.41 (1H, m), 1.00 (3H, s), 0.97 (3H, s), 0.93 (3H, t).

Example 3E

Synthesis of Capping Group 3e4

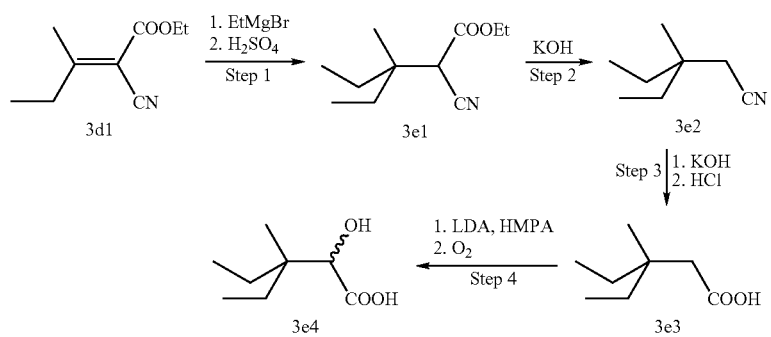

Following the procedure of Example 3D, steps 2 to 5, but using ethyl magnesium bromide in place of methyl magnesium bromide in step 2, compound 3e4 was obtained.

Synthesis of Dipeptides

Example 4A

Synthesis of P2 Brosylate Intermediate (4a3)

To a solution of Boc-cis-Hyp-OH 4a1 (1.86 g, 7.58 mmol), 4-bromobenzene sulfonyl chloride 4a2 (3.85 g, 15.07 mmol) and DMAP (96 mg, 0.79 mmol), in 70 mL of $CH_2Cl_2$, was added $Et_3N$ (3.7 mL, 26.55 mmol). The reaction mixture was stirred at 40° C. for 12 h. The solvent was removed in vacuo.

The residue, diluted with EtOAc, successively washed with HCl 1M (2×100 mL), $NaHCO_3$ sat. and brine. After the usual treatment ($MgSO_4$, filtration and concentration), the compound was purified by flash chromatography (elution conditions: 75:25 Hexanes/EtOAc) to give 3.0 g (85%) of white solid 4a3.

Example 4B

Hydrolysis of P2 Brosylate Intermediate (4b1)

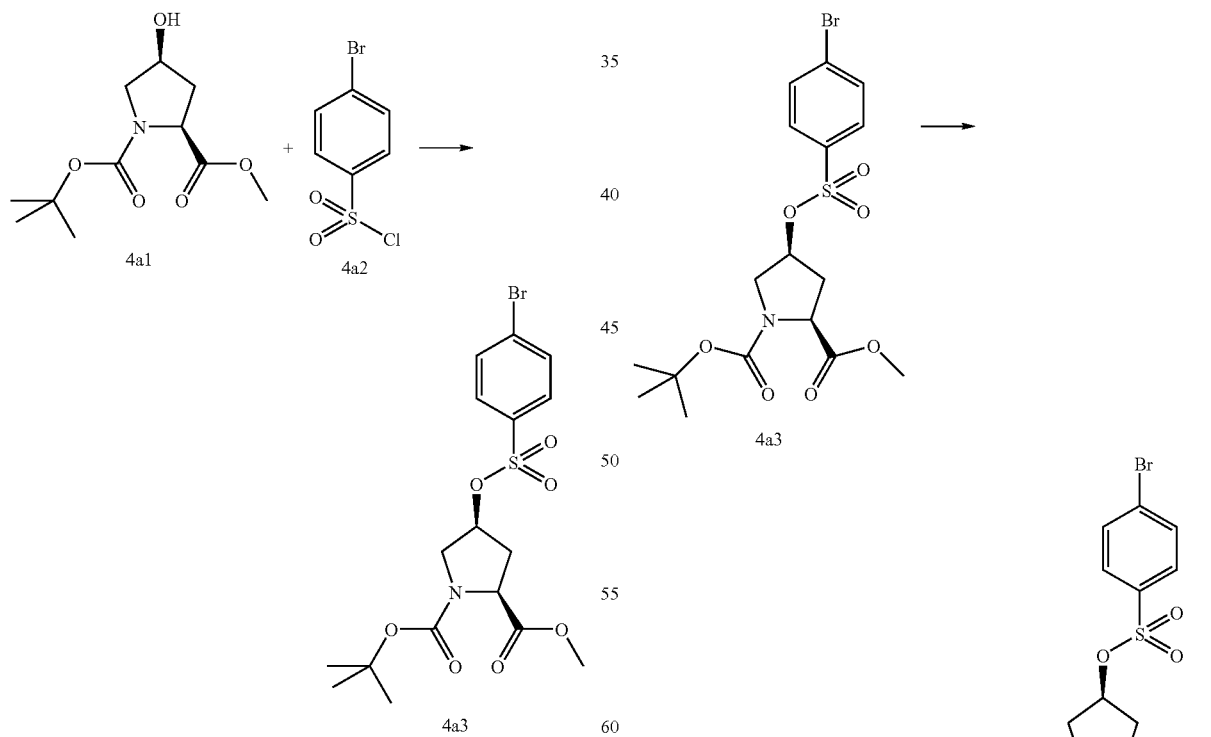

83

To ester 4a3 (503 mg, 1.08 mmol), in 7 mL of a mixture THF:H₂O (2.5:1), was added a solution of NaOH 1M (1.6 mL, 1.60 mmol) followed by 2 mL of MeOH. The resulting solution was stirred at room temperature for 4 hours. The solvents were removed in vacuo. The residue, diluted with H₂O, acidified with HCl 1M and then extracted with EtOAc (3×50 mL). After the usual treatment (MgSO₄, filtration and concentration), 460 mg (94%) of white solid 4b1 was isolated.

Example 4C

Preparation of Dipeptide (4c1)

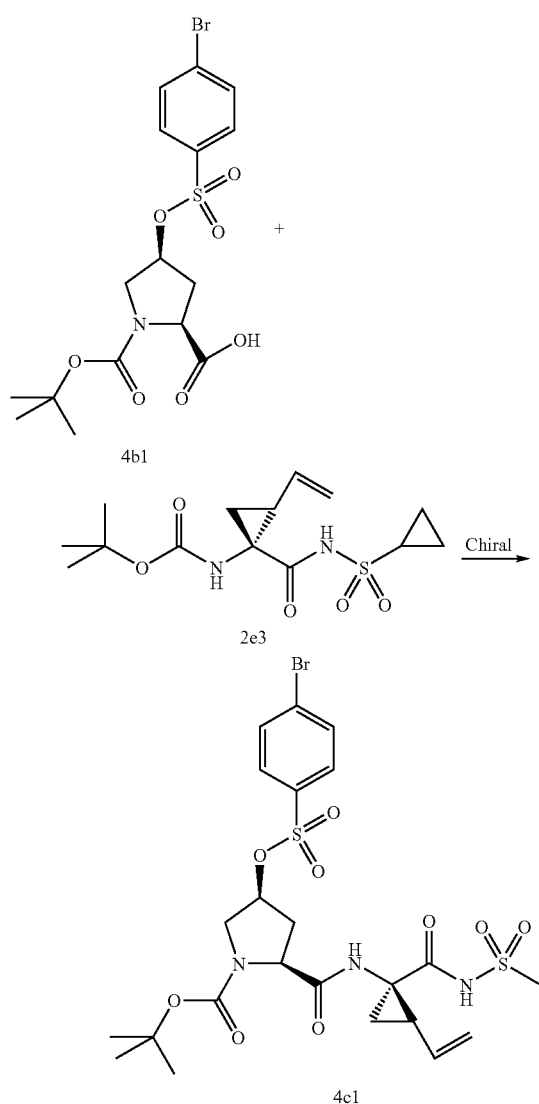

Deprotection of 2e3:

The BocP1P1' 2e3 (375 mg, 1.13 mmol), in 8 mL of 4M HCl/dioxane, was stirred at room temperature. After 30 minutes the solid appeared. MeOH was added until complete dissolution and the reaction was stirred for an additional 30 min. Before evaporation of the solvent, the residue was dried under vacuum to afford the amine salt as an off white solid.

Coupling Step:

To the solution of acid 4b1 (460 mg, 1.02 mmol), in 10 mL of CH₃CN, was added HATU (410 mg, 1.08 mmol) followed by of DIPEA (0.45 mL, 2.58 mmol). In another flask a solution of the amine salt (0.26 g, 1.13 mmol) in 5 mL of CH₃CN was made and to it was added DIPEA (0.45 mL, 2.58 mmol). This amine solution was added to the solution of the activated ester and the resulting solution was stirred at room temperature for 14 h. The reaction mixture was diluted with EtOAc, washed with HCl M (2×50 mL), dried (MgSO₄) and purified by flash chromatography (elution conditions: 30:70 Hexanes/EtOAc) to furnish 334 mg (49%) of the desired compound 4c1.

Example 4D

Preparation of Dipeptide (4d1)

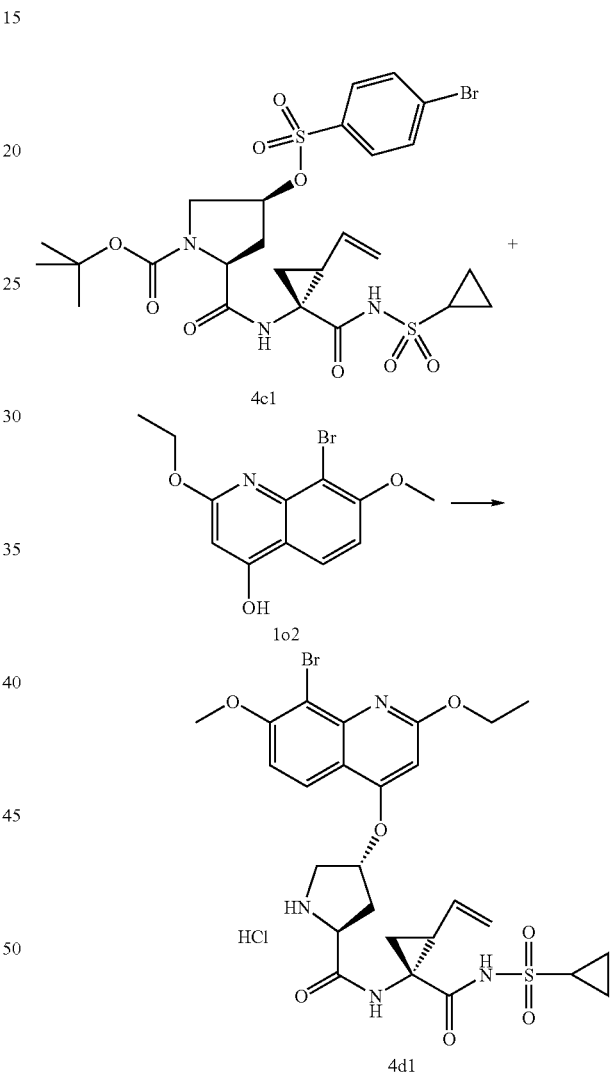

To a solution of compound 4c1 (3 g, 4.528 mmol) and the quinoline 1o2 (1.35 g, 4.528 mmol) in 1-methyl-2-pyrrolidinone (NMP, 20 mL) was added cesium carbonate (1.66 g, 5.11 mmol). The mixture was heated to 70° C. for 8 h. The reaction mixture was cooled and poured into EtOAc and the resulting solution was washed with H₂O (2×150 mL) and brine (3×150 mL). The organic phase was dried, filtered and concentrated to afford the crude product as a yellow solid which was purified by column chromatography (2/8 hexane/EtOAc) to afford 2.26 g (69%) of the BOC-protected intermediate as a pale yellow solid. This product was dissolved in a solution of HCl in dioxane (4N; 4 mL) and the mixture was stirred for 1 h and concentrated to dryness to give compound 4d1 (2.04 g, 99%), which was used as such in the next step.

Example 4E

Preparation of Acylated Dipeptide 4e2 (Compound 1013 of Table 1)

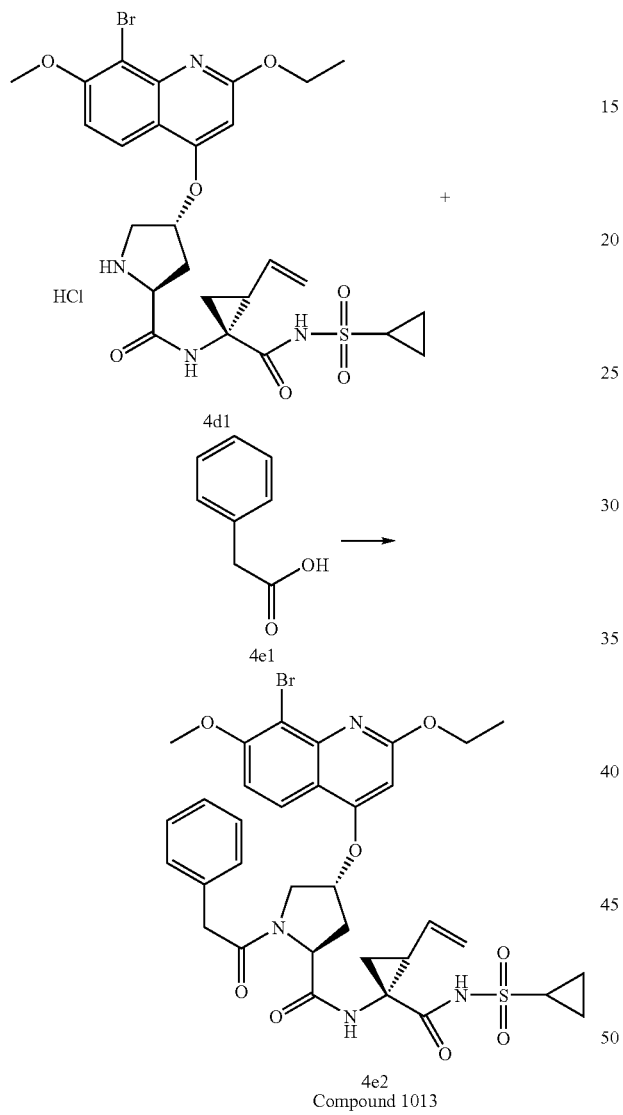

4e2
Compound 1013

To solution of the amine 4d1 (HCl salt) (40 mg, 0.061 mmol) and DIPEA (32 µL, 0.183 mmol) in DMF (1.5 mL) was added pre-made solution of HATU (28 mg, 0.073 mmol) in DMF (0.5 mL). The pH of the reaction mixture was adjusted to 8 with DIPEA. The acid 4e1 (8.3 mg, 0.061 mmol) was then added. The reaction mixture was stirred at rt for 12 h, filtered over millex filter and purified by prep HPLC (YMC Combiscreen ODS-AQ, 50×20 mm ID S-5 micron, 120A; 220 nm) using a linear gradient and 0.06% TFA CH$_3$CN/H$_2$O. The pure fractions were combined and lyophilized to provide the product 4e2 (compound 1013, Table 1) as the trifluoroacetate salt (11 mg, 26%). $^1$H NMR (400 MHz, DMSO-d$_6$): δ 10.50 (s, 1H), 9.01 (s, 1H), 7.78 (d, J=9 Hz, 1H), 7.27 (d, J=9 Hz, 1H), 7.20-7.0 (m, 5H), 6.40 (s, 1H), 5.65-5.55 (m, 1H), 5.39 (brs, 1H), 5.26 (d, J=17 Hz, 1H), 5.11 (d, J=10 Hz, 1H), 4.50 (q, J=7 Hz, 2H), 4.36 (dd, J=7.3 Hz, J=10 Hz, 1H), 3.98 (s, 1H), 3.98-3.94 (m, 1H), 3.88 (dd, J=3.3 Hz, J=12.3 Hz, 1H), 3.68 (ABq, J=15.3 Hz, 2H), 2.84-2.76 (m, 1H), 2.28-2.09 (m, 2H), 1.72 (dd, J=5 Hz, J=8 Hz, H), 1.38 (t, J=7 Hz, 3H), 1.30 (dd, J=5.0 Hz, J=9.4 Hz, 1H), 1.10-0.85 (m, 4H). EIMS: (M+H)$^+$=741.0, (MH+2)$^+$=743.2

Example 4F

Preparation of Urea-Derivatized Dipeptide 4f1 (Compound 1027 of Table 1)

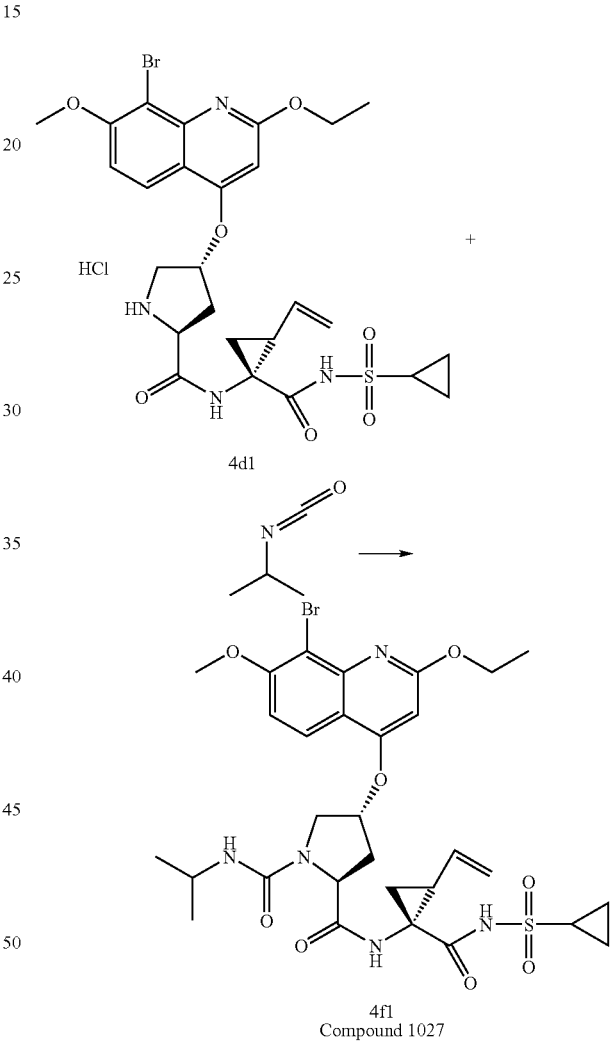

4f1
Compound 1027

To a solution of the amine 4d1 (HCl salt) (40 mg, 0.061 mmol) and DIPEA (32 µL, 0.183 mmol) in CH$_2$Cl$_2$ (2 mL) was added isopropyl isocyanate (5.2 µL, 0.061 mmol). The pH was adjusted to 8 with DIPEA. The reaction mixture was stirred at rt for 12 h. The residue was filtered over Millex filters and purified by prep HPLC (YMC Combiscreen ODS-AQ, 50×20 mm ID S-5 micron, 120A; 220 nm) using a linear gradient and 0.06% TFA CH$_3$CN/H$_2$O. The pure fractions were combined and lyophilized to provide the product urea 4f1 (compound 1027, Table 1) as the trifluoroacetate salt (11 mg, 26%). $^1$HNMR (400 MHz, DMSO-d6): δ 10.96 (s, 1H), 9.15 (s, 1H), 7.91 (d, J=9 Hz, 1H), 7.31 (d, J=9 Hz, 1 Hz, 1H), 6.40 (s, 1H), 6.28 (d, J=7.8 Hz, 1H), 5.7-5.6 (m, 1H), 5.41 (brs, 1H), 5.30 (d, J=17 Hz, 1H), 5.11 (d, J=10 Hz, 1H), 4.51 (q, J=7 Hz, 2H), 4.27 (dd, J=7 Hz, J=9.2 Hz, 1H), 3.96 (s, 3H), 3.83-3.95 (m, 1H), 3.75 (dd, J=4.1, J=12 Hz, 1H), 3.65 (d, J=12 Hz, 1H), 2.94-2.85 (m, 1H), 2.43-2.35 (m, 1H), 2.24-211 (m, 2H), 1.72 (dd, J=5 Hz, J=9.2 Hz, 1H), 1.39 (t, J=7.2 Hz, 3H), 1.32 (dd, J=5 Hz, J=9.2 Hz, 1H), 1.12-0.9 (m, 4H), 1.03 (d, J=6.4 Hz, 3H), 0.97 (d, J=6.4 Hz, 3H). EIMS: (M+H)$^+$=708.0, (MH+2)$^+$=710.2.

Example 4G

Preparation of Sulfonamide-Derivatized Dipeptide 4g1 (Compound 1030 of Table 1)

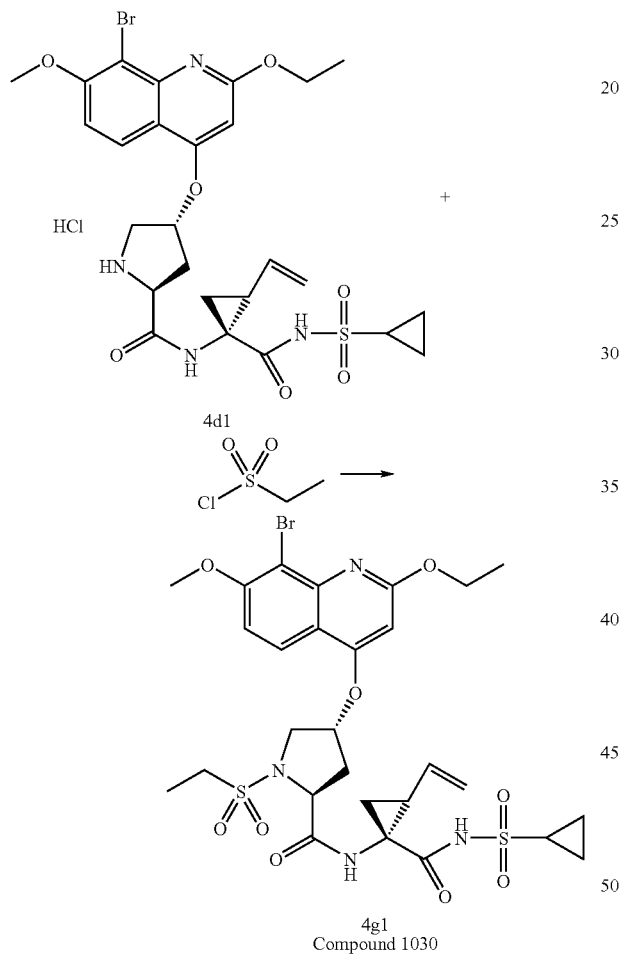

4g1
Compound 1030

To a solution of the amine 4d1 (HCl salt) (40 mg, 0.061 mmol) and DIPEA (32 µL, 0.183 mmol) in $CH_2Cl_2$ (2 mL) was added ethanesulfonyl chloride (5.8 µL, 0.061 mmol). The pH was adjusted to 8 with DIPEA. The reaction mixture was stirred at rt for 12 h. The residue was filtered over Millex filters and purified by prep HPLC (YMC Combiscreen ODS-AQ, 50×20 mm ID S-5 micron, 120A; 220 nm) using a linear gradient and 0.06% TFA $CH_3CN/H_2O$. The pure fractions were combined and lyophilized to provide the product 4g1 (compound 1030) as the trifluoroacetate salt (10 mg, 23%). $^1$HNMR (400 MHz, DMSO-d6): δ 10.87 (s, 1H), 8.61 (s, 1H), 802 (d, J=9 Hz, 1H), 7.29 (d, J=9 Hz, 1H), 6.49 (s, 1H), 5.33 (brs, 1H), 5.30 (d, J=16 Hz, 1H), 5.11 (d, J=9 Hz, 1H), 4.55-4.42 (m, 3H), 3.97 (s, 3H), 3.89-3.76 (m, 2H), 3.33-3.16 (m, 1H), 3.05-2.95 (m, 1H), 2.95-2.85 (m, 1H), 2.60-2.70 (m, 1H), 2.37-2.15 (m, 2H), 1.76 (dd, J=5.2, J=7.6, 1H), 1.39 (t, J=7 Hz, 3H), 1.26 (dd, J=5.2, J=9.4, 1H), 1.16 (t, J=7.4, 3H), 1.1-0.95 (m, 4H).

EIMS: (M+H)$^+$=715.2, (MH+2)$^+$=717.2

Example 4H

Preparation of Carbamate-Derivatized Dipeptide 4h1 (Compound 1023 of Table 1)

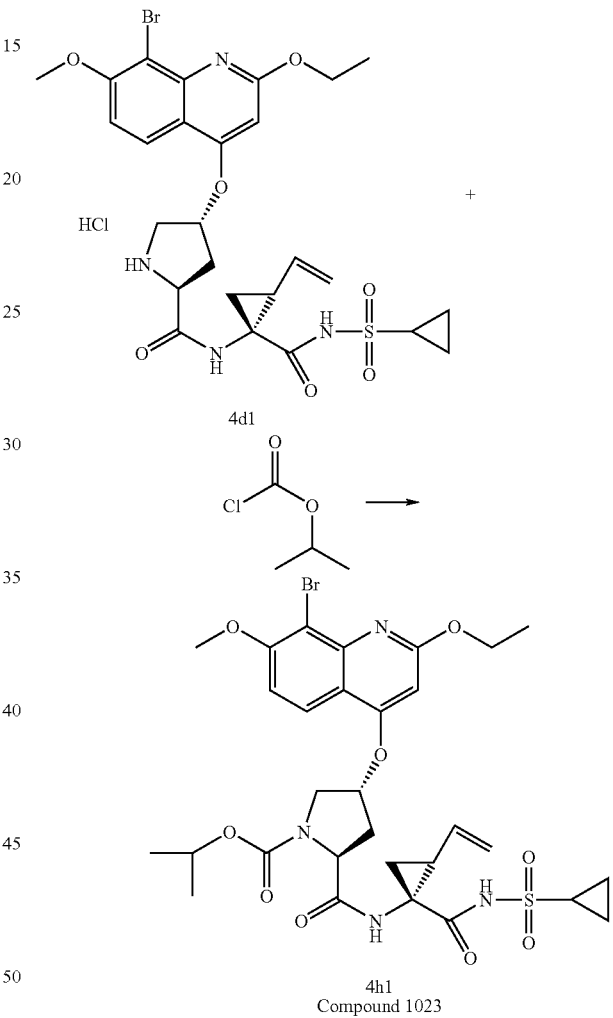

4h1
Compound 1023

To a solution of the amine 4d1 (HCl salt) (40 mg, 0.061 mmol) and DIPEA (32 µL, 0.183 mmol) in $CH_2Cl_2$ (2 mL) was added isopropylchloroformate (1M soln in THF, 61 µL, 0.061 mmol). The pH was adjusted to 8 with DIPEA. The reaction mixture was stirred at rt for 12 h. The residue was filtered over Millex filters and purified by prep. HPLC (YMC Combiscreen ODS-AQ, 50×20 mm ID S-5 micron, 120A; 220 nm) using a linear gradient and 0.06% TFA $CH_3CN/H_2O$. The pure fractions were combined and lyophilized to provide the product 4h1 (compound 1023) as the trifluoroacetate salt (18.5 mg, 43%). $^1$HNMR (400 MHz, DMSO-d6): δ 11.20, 10.45 (2s, 1H), 9.10, 8.37 (2s, 1H), 7.90 (d, J=9 Hz, 1H), 7.30 (d, J=9 Hz, 1H), 6.51, 6.47 (2s, 1H), 5.66-5.40 (m, 1H), 5.36 (brs, 1H), 5.27 (d, J=17 Hz, 1H), 5.11 (d, J=10 Hz, 1H), 4.85-4.67 (m, 1H), 4.50 (q, J=7 Hz, 2H), 4.32-4.23 (m, 1H), 3.96 (s, 3H), 3.89-3.67 (m, 2H), 2.96-2.86 (m, 1H), 2.33-2.15 (m, 2H), 1.82-1.70 (m, 1H), 1.39 (t, J=7 Hz, 3H), 1.34-1.29 (m, 1H), 1.18 (d, J=6 Hz, 3H), 1.11 (d, J=6 Hz, 3H), 1.18-0.93 (m, 5H). EIMS: $(M+H)^+=709.2$, $(MH+2)^+=711.2$.

Example 4I

Preparation of Acyl-Derivatized Dipeptide 4I3 (Compound 1038 of Table 1)

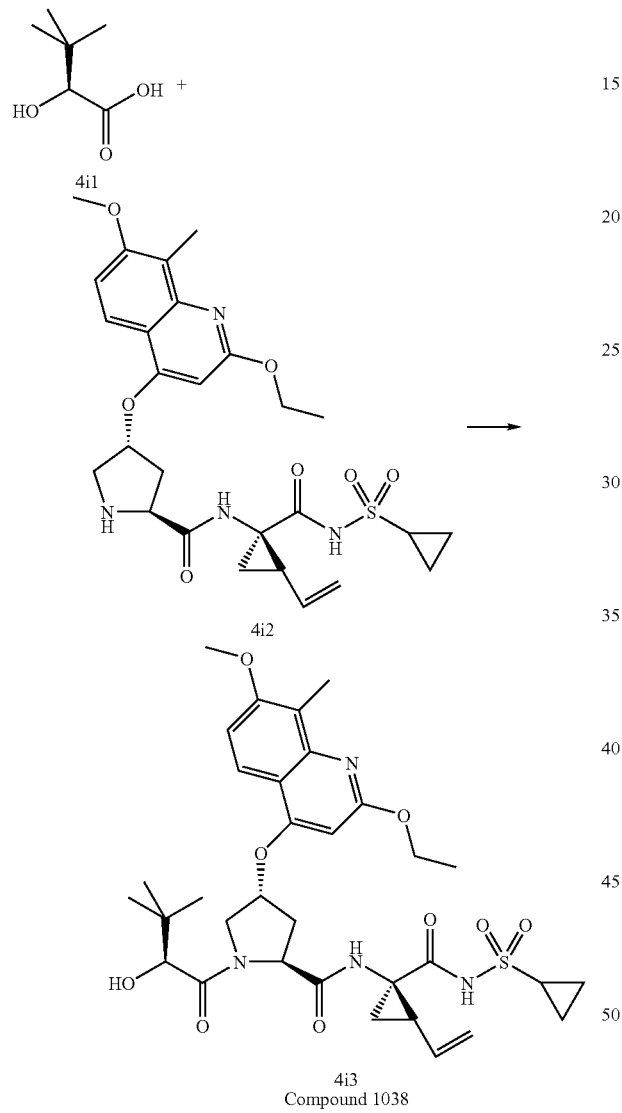

4i3
Compound 1038

To a solution of the (S)-2-hydroxy-3,3-dimethylbutyric acid 4i1 (11 mg, 0.083 mmol), the amine 4i2 prepared by analogous methods to those described in Examples 4A-D (36 mg, 0.065 mmol) and DIPEA (0.072 mL, 0.41 mmol), in 0.75 mL of DMF, was added a solution of DIC (0.015 mL, 0.096 mmol) HOAt (13 mg, 0.096 mmol) in 0.75 mL of DMF. The resulting solution was stirred at room temperature 12 h. The reaction mixture, diluted with AcOH, was purified by preparatory HPLC (YMC Combiscreen ODS-AQ, 50×20 mm ID S-5 micron, 120A; 220 nm) using a linear gradient and 0.06% TFA CH$_3$CN/H$_2$O. The pure fractions were combined, concentrated and lyophilized to provide the product 4i3 (compound 1038, Table 1) as the trifluoroacetate salt (30 mg, 68%). $^1$H NMR (400 MHz, DMSO-d$_6$): δ 10.53 (s, 1H), 8.98 (s, 1H), 7.75 (d, J=9 Hz, 1H), 7.19 (d, J=9 Hz, 1H), 6.36 (s, 1H), 5.68-5.56 (m, 1H), 5.38 (brs, 1H), 5.24 (d, J=17 Hz, 1H), 5.09 (d, J=10 Hz, 1H), 4.51-4.39 (m, 4H), 4.30-4.18 (m, 4H), 3.59-3.57 (m, 6H), 2.94-2.86 (m, 1H), 2.44-2.39 (m, 4H), 2.19-2.07 (m, 2H), 1.73-1.68 (m, 1H), 1.40-1.31 (m, 4H), 1.11-0.98 (m, 4H), 0.87 (s, 9H). EIMS: (M+H)=673.3, (M−H)=671.3

Example 4J

Preparation of Acyl-Derivatized Dipeptide 4j1 (Compound 1039 of Table 1)

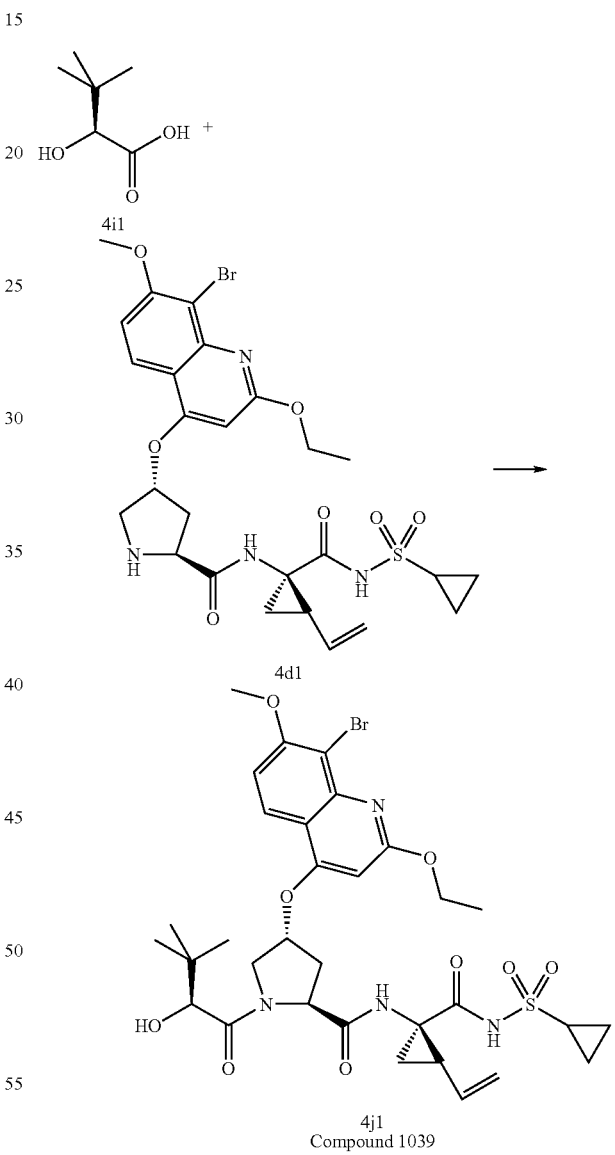

4j1
Compound 1039

To a solution of the S-2-hydroxy-3,3-dimethylbutyric acid 4i1 (9 mg, 0.066 mmol), the amine 4d1 (33 mg, 0.053 mmol) and DIPEA (0.046 mL, 0.265 mmol), in 0.75 mL of DMF, was added a solution of DIC (0.012 mL, 0.074 mmol) HOAt (11 mg, 0.074 mmol) in 0.75 mL of DMF. The resulting solution was stirred at room temperature 12 h. The reaction mixture, diluted with AcOH, was purified by prep HPLC (YMC Combiscreen ODS-AQ, 50×20 mm ID S-5 micron, 120A; 220 nm) using a linear gradient and 0.06% TFA CH$_3$CN/H$_2$O. The pure fractions were combined, concentrated and lyophilized to provide the product 4j1 (Compound 1039) as the trifluoroacetate salt (10.2 mg, 26%). $^1$HNMR (400 MHz, DMSO-d6): δ 10.53 (s, 1H), 8.96 (s, 1H), 7.89 (d, J=9 Hz, 1H), 7.30 (d, J=9 Hz, 1H), 6.48 (s, 1H), 5.70-5.55 (m, 1H), 5.41 (brs, 1H), 5.25 (d, J=17 Hz, 1H), 5.10 (d, J=10 Hz, 1H), 4.51 (q, J=7 Hz, 2H), 4.41 (dd, J=7 Hz, J=10 Hz, 1H), 4.25 (d, J=13 Hz, 1H), 4.05-3.80 (m, 5H), 2.95-2.80 (m, 1H), 2.55-2.49 (m, 2H, under the DMSO-d6 peak), 2.20-2.05 (m, 2H), 1.71 (dd, J=5.5 Hz, J=8 Hz, 1H), 1.45-1.30 (m, 4H), 1.15-0.95 (m, 4H), 0.86 (s, 9H). EIMS: (M+H)$^+$=737, (MH+2)$^+$=739.

Example 4K

Preparation of Dipeptide 4k2

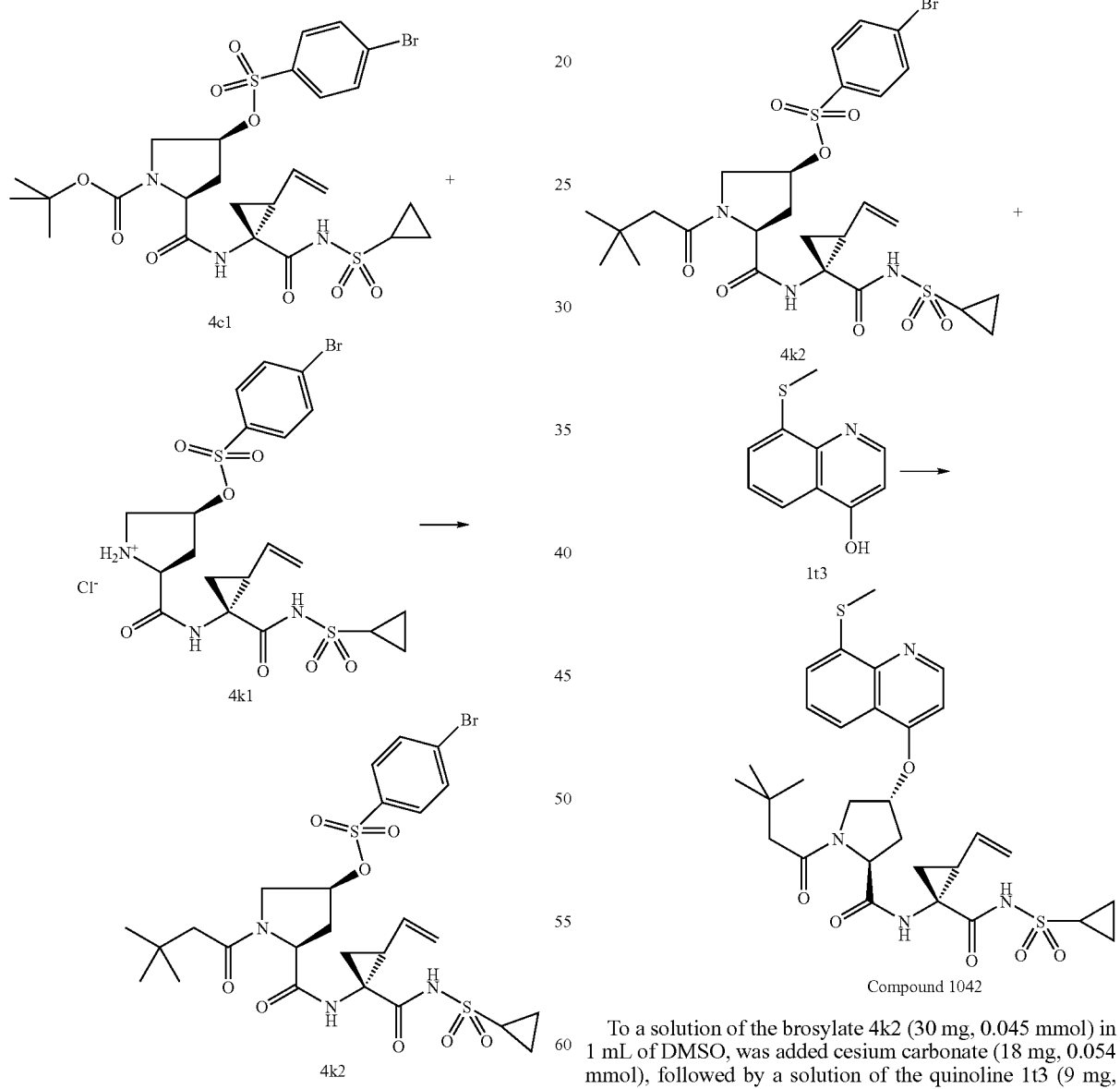

To the Boc protected amine 4c1 (900 mg, 1.36 mmol) was added a 4N HCL/dioxane solution (25 mL). The reaction mixture was stirred at room temperature for 1 hours then concentrated to dryness to afford the amine 4k1 (775 mg, 95%). To a solution of the amine 4k1 (HCl salt, 775 mg, 1.30 mmol) and DIPEA (0.68 mL, 3.90 mmol) in DMF (6 mL) was added HATU (590.5 mg, 1.55 mmol) followed by 3,3-dimethylbutyric acid (173.2 µl, 1.36 mmol). The reaction mixture was stirred at r.t. for 12 h. The reaction was diluted with EtOAc (50 mL), the organic phase was washed with citric acid (2×) and brine (2×); then dried (MgSO$_4$), filtered and concentrated under reduced pressure. The residue was purified by flash chromatography (silica gel 40-60µ) 2:8 Hex: EtOAc) to give product 4k2 (508 mg, 60%) as a white foam.

Example 4L

Preparation of Acyl-Derivatized Dipeptide, Compound 1042 of Table 1

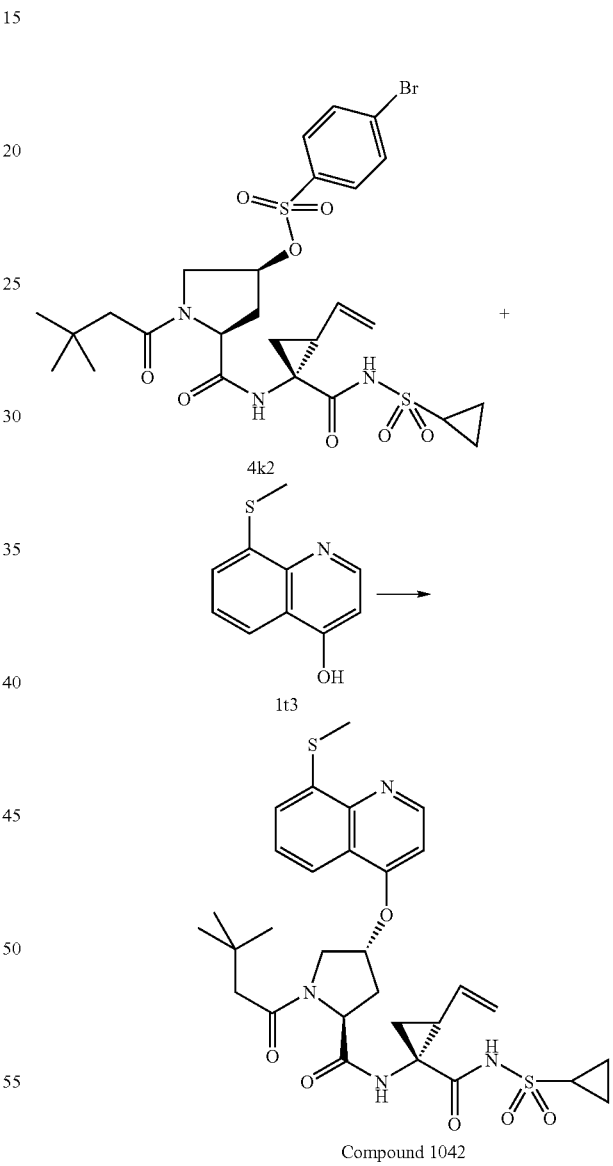

Compound 1042

To a solution of the brosylate 4k2 (30 mg, 0.045 mmol) in 1 mL of DMSO, was added cesium carbonate (18 mg, 0.054 mmol), followed by a solution of the quinoline 1t3 (9 mg, 0.047 mmol) in 1 mL of DMSO. The resulting solution was stirred at 70° C. for 8 h. The reaction mixture was cooled down to room temperature, filtered over Millex filter and purified by prep HPLC (YMC Combiscreen ODS-AQ, 50×20 mm ID S-5 micron, 120A; 220 nm) using a linear gradient and 0.06% TFA CH$_3$CN/H$_2$O. The pure fractions were combined, concentrated and lyophilized to provide the product Compound 1042 as the trifluoroacetate salt (4.6 mg, 13%). ¹HNMR (400 MHz, DMSO-d6): δ 10.47 (s, 1H), 9.06 (s, 1H), 8.74 (d, J=4 Hz, 1H), 7.78 (d, J=8 Hz, 1H), 7.60-7.35 (m, 2H), 7.16 (d, J=4.5 Hz, 1H), 5.70-5.55 (m, 1H), 5.48 (brs, 1H), 5.95 (d, J=10 Hz, 1H), 5.25 (d, J=17 Hz, 1H), 4.65-4.50 (m, 1H), 4.45-4.30 (m, 1H), 4.15-3.90 (m, 3H), 2.95-2.85 (m, 2H), 2.35-2.05 (m, 5H), 1.75-1.65 (m, 1H), 2.40-2.30 (m, 2H), 1.15-0.85 (m, 16H). EIMS: (M+)=615.1.

Example 4M

Preparation of Dipeptide 4m4

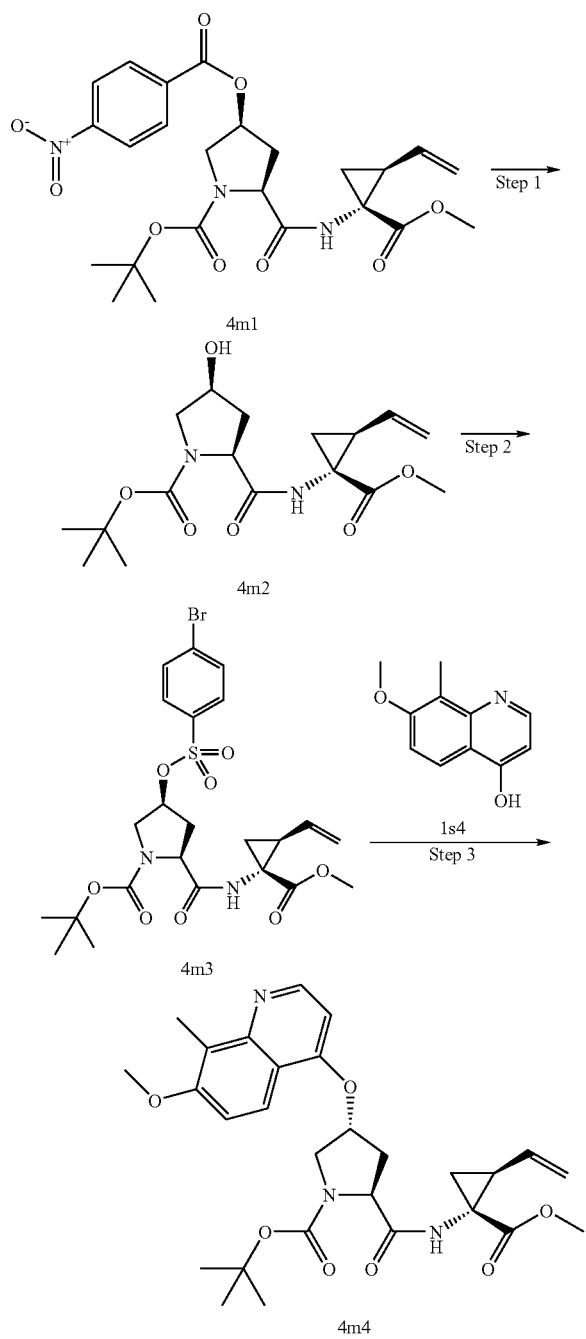

Step 1: The purified compound 4 ml (prepared as described in WO 03/064456) (2.15 g, 4.27 mmol) was dissolved in THF (57 mL) and water (9 mL) and cooled to 0° C. (ice bath). Solid LiOH (monohydrate) (224 mg, 5.34 mmol, 1.3 eq) was dissolved in water (9 mL) and added to the cooled solution over ca. 10 minutes with rapid stirring. The reaction was stirred for 2 hours (0 C.) until the starting material had been completely consumed by HPLC analysis. The excess base was neutralized with 0.5N HCl to give a final pH of ~6. The THF was evaporated off and the residue dissolved in EtOAc and washed 3× with sat. NaHCO₃ (aq), followed by saturated brine (1×). The organic phase was dried over MgSO₄, filtered and concentrated to dryness to give a white foamy solid (1.35 g). Purification by flash chromatography (column diameter: 50 mm) with regular mesh silica gel (150 mL) to a height of about 13 cm. The initial eluent was Hexane/EtOAc (2:8), then neat EtOAc to obtain the desired product 4m2 as a white foamy solid (1.25 g, 83% yield). HPLC homogeneity was 97%. MS: 353.1 (M–H)– and 377.1 (M+Na)+, and NMR was consistent with the desired compound.

Step 2: The purified dipeptide 4m2 (1.25 g, 3.53 mmol) was dissolved in methylene chloride (48 mL) with 4-bromobenzene sulfonyl chloride (1.89 g, 7.41 mmol, 2.1 equiv.). To this solution was added triethylamine (1.74 mL, 12.5 mmol, 3.5 equiv.), and a catalytic amount of DMAP (43 mg, 0.35 mmol, 0.1 equiv.). The reaction was stirred at 40 C. for 16 hours before being diluted with EtOAc, and then washed with sat. NaHCO₃ (aq) (2×), water (2×), and sat. brine (1×). The organic phase was dried over MgSO₄, filtered and concentrated to give a beige-orangy foam (2.3 g crude wt). This material was purified by flash chromatograghy (50 mm column diameter) using regular silica gel (~250 mL) to a height of about 18 cm. The eluent was 1:1 Hexane/EtOAc which provided 1.68 g of an off-white foamy solid 4m3 (83%). HPLC analysis gave >99% homogeneity, MS: 571.1 and 573 (es– mode) and 573.1 and 575 (in es+ mode). ¹H NMR (400 MHz, CDCl3) δ7.77 (d, 2H), 7.70 (d, 2H), 5.83-5.71 (m, 1H), 5.28 (d, 1H), 5.15 (d, 1H), 5.07 (bs, 1H), 4.31 (bd, 1H), 3.77-3.63 (m, 2H), (3.69 (s, 3H), 2.49 (bs, 1H), 2.11-2.02 (m, 1H), 1.87-1.80 (m, 1H), 1.49 (d, 2H), 1.45 (s, 9H).

Step 3: To a solution of the brosylate 4m3 (105 mg; 0.15 mmol) and the hydroxyquinoline 1s4 (32.6 mg; 0.173 mmol) in 1-methyl-2-pyrrolidinone (NMP; 3.0 mL) was added cesium carbonate (73.3 mg; 0.225 mmol). The resulting suspension was placed into a pre-heated oil bath at a bath temperature of 70° C. and stirred for 2 hours. HPLC indicated reaction was complete. The reaction mixture was diluted with EtOAc and extensively washed with water (4×; NMP is soluble in water and easily removed), saturated NaCO₃ (3×), 1N NaOH (1×; removes excess quinoline) and brine (2×). The organic layer was dried (MgSO₄), filtered and evaporated to provide the product 4m4 as a light yellow foam (93.2 mg; 96% yield). MS 649.3 (M–H)– 651.4 (M+H)+. Homogeneity by HPLC (TFA) @ 220 nm:92%. This compound was purified by column chromatography using a mixture of Ethyl acetate and hexanes.

Example 4N

Synthesis of Compound 1049 of Table 1

Step 1:

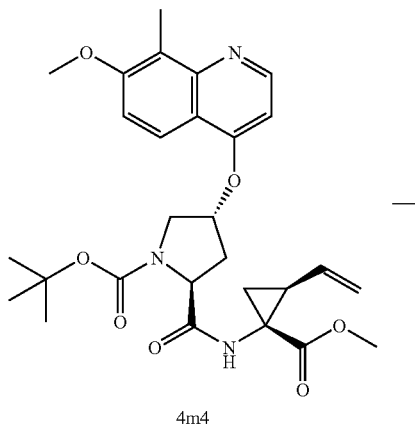

4m4

To the ester 4m4 (430 mg, 0.818 mmol) in methanol (1 mL), was added THF (1 mL) and NaOH 1M solution (0.818 mL, 0.818 mmol), stirred at room temperature for 18 hours. The reaction mixture was concentrated to dryness to afford 415 mg of compound 4n1 which was used as it is for the next reaction.

Step 2:

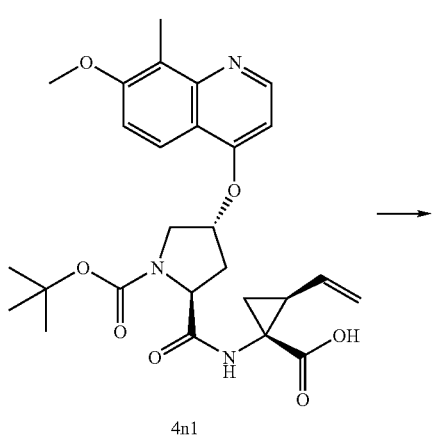

4n1

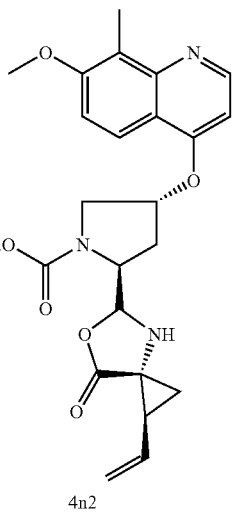

4n2

To the dipeptide 4n1 in $CH_2Cl_2$ (6 mL) at 0° C. was added TEA (339 µL, 2.43 mmol), followed by the addition of isobutylchloroformate (dropwise) (158 µL, 1.22 mmol). The reaction mixture was stirred at 0° C. for 30 min, then at room temperature for 8 hours. The residue was purified by flash chromatography (silica gel 40-60p) 8/2 Hex/EtOAc) to give 210 mg of 4n2 as a white foam (52%).

Step 3:

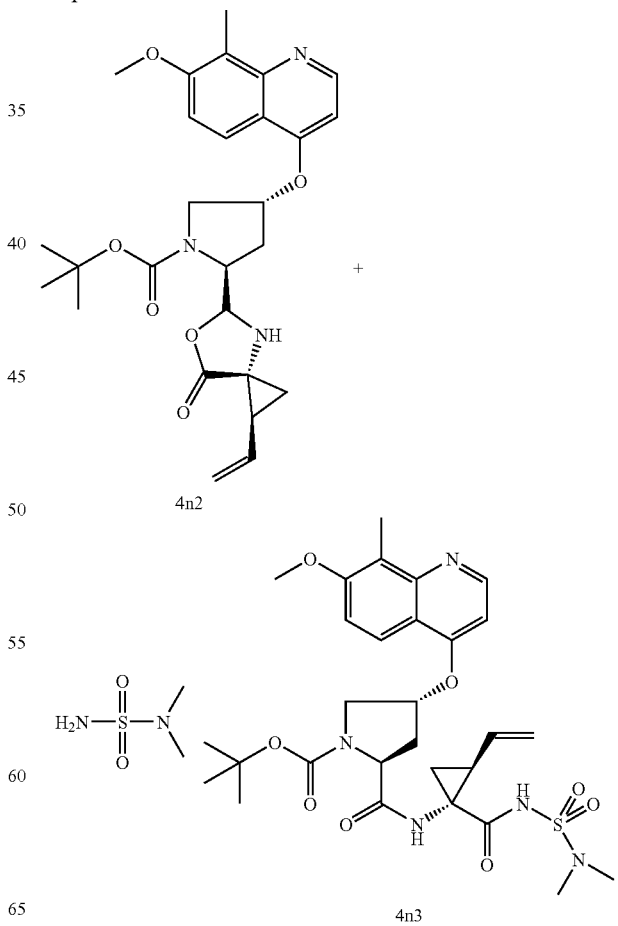

In an oven dried reaction flask was dissolved N,N-dimethylsulfamide (79 mg, 0.636 mmol) in anhydrous THF (2 mL) and cooled to a bath temperature of −15 to −20° C. To this cold solution was added a solution of LiHMDS (1M in THF) (636 μL, 0.636 mmol) in one shot. The reaction mixture was allowed to stir at the same bath temp for 5 min, then at room temperature for 20 min. Cooled reaction mixture to a bath temp of −10 to −15° C., then added drop wise the azalactone 4n2 (210 mg, 0.42 mmol) dissolved in THF (2 mL). The reaction mixture was warmed slowly to the room temperature and let it stir at that temperature for 12 h. Added few drops of AcOH, concentration to dryness. The residue was purified by flash chromatography (silica gel 40-60μ) 2/8 Hex/EtOAc) to give 147 mg of a white solid 4n3 (56%).

Step 4:

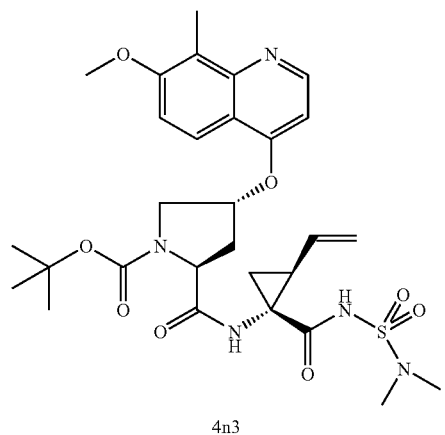

4n3

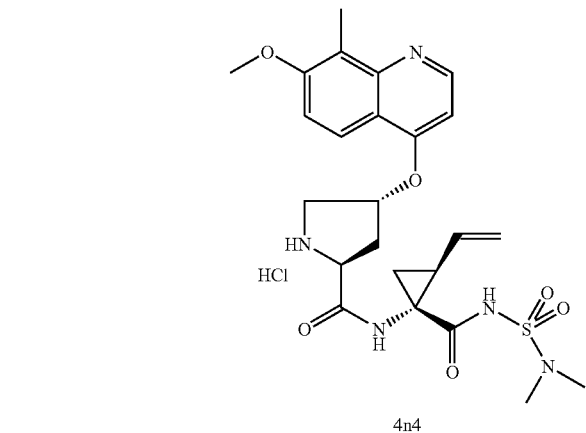

4n4

To the Boc protected amine 4n3 (147 mg, 0.238 mmol) was added a 4N HCL/dioxane solution (5 mL). The reaction mixture was stirred at room temperature for 4 hours, then concentrated to dryness to provide 4n4.

Step 5:

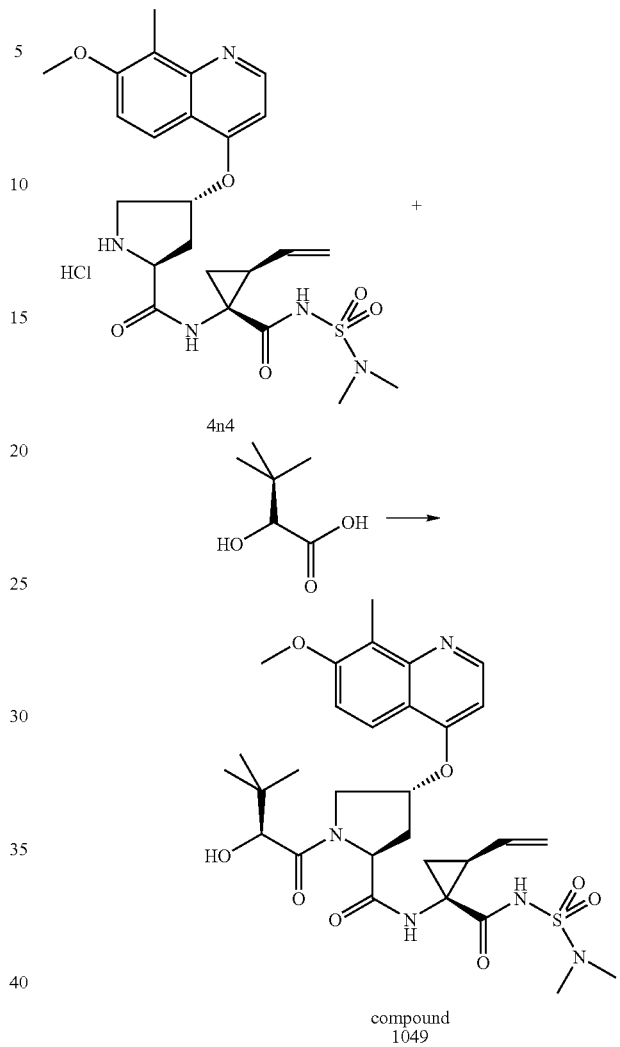

compound 1049

To a solution of (S)-2-hydroxy-3,3-dimethylbutyric acid (41 mg, 0.309 mmol), the amine 4n4 (HCl salt, 128 mg, 0.247 mmol) and DIPEA (216 μL, 0.346 mmol) in DMF (5 mL), was added the solution of DIC (55 mg, 0.346 mmol)-HOAT (47 mg, 0.346 mmol) in 2.5 mL of DMF. The reaction was stirred at room temperature for 12 h. The reaction mixture was concentrated and the residue was dissolved in acetic acid, filtered through a Millex filter and purified by prep. HPLC (YMC Combiscreen ODS-AQ, 50×20 mm ID S-5 micron, 120A; 220 nm) using a linear gradient and 0.06% TFA $CH_3CN/H_2O$. The pure fractions were combined, concentrated and lyophilized to provide the product compound 1049 as the trifluoroacetate salt (69 mg, 44%). $^1H$ NMR (400 MHz, DMSO-$d_6$) 11.02 (s, 0.2H), 10.37 (s, 0.8H), 8.95 (s, 1.8H), 8.52 (s, 0.2H), 8.11 (d, J=7 Hz, 1H), 7.70 (d, J=9 Hz, 1H), 7.35 (s, 1H), 5.69 (s, 1H), 5.61-5.51 (m, 1H), 5.24 (d, J=17 Hz, 1H), 5.11 (d, J=9 Hz, 1H), 4.50-4.46 (m, 1H), 4.35 (d, J=13 Hz, 1H), 4.03 (s, 5H), 3.87 (s, 2H), 2.77 (s, 6H), 2.52 (d, J=3 Hz, 3H), 2.26-2.07 (m, 2H), 1.73-1.70 (m, 1H), 1.29-1.27 (m, 1H), 0.86 (s, 9H).

EIMS M+H=632.3, M−H=630.3.

Example 4O

Synthesis of Compound 1051 of Table 1

Step 1:

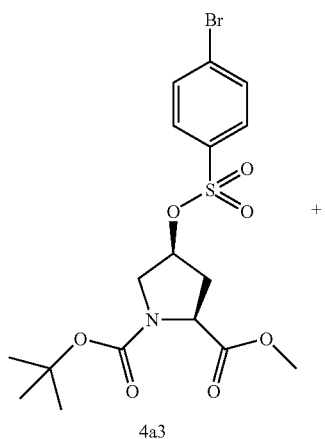

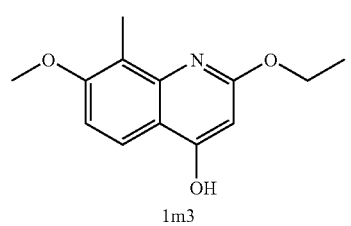

A solution of the proline brosylate 4a3 (557 mg, 1.20 mmol), the quinoline 1m3 (335 mg, 1.44 mmol, 1.2 eq) and cesium carbonate (586 mg, 1.80 mmol, 1.5 eq), in 7.5 mL of NMP, was heated to 70° C. for 2 hours. The reaction mixture, diluted with EtOAc, was washed with H₂O X3, saturated sodium bicarbonate and brine, dried over MgSO₄, filtered and concentrated under vacuum. The crude material was purified by flash column chromatography with Hexanes:EtOAc 80:20 to provide 445 mg of the desired compound 4o1 (80% yield).

Step 2:

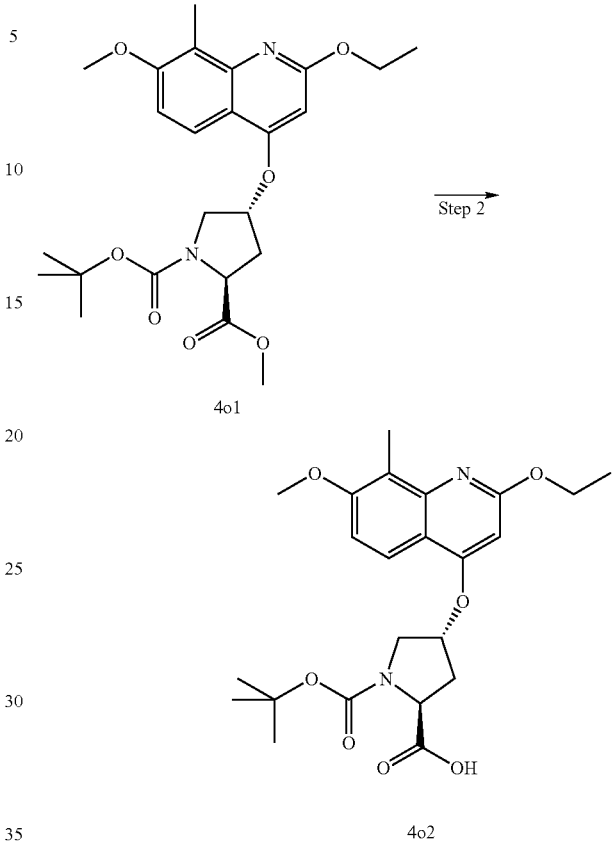

To the proline ester 4o1 (238 mg, 0.52 mmol), dissolved in 7 mL of a mixture of THF:H₂O (2.5:1), was added 1.3 mL of NaOH 1M (1.30 mmol, 2.5 eq). 1 mL of MeOH was subsequently added to clarified the solution, which was then stirred at RT for 2 hours. The solvents were removed in vacuo. The residue was diluted with H₂O and acidified to pH~6 with HCl 1M. This aqueous layer was then extracted three times with EtOAc, dried over MgSO₄, filtered and concentrated under vacuum. 230 mg (99% yield) of the crude material 4o2 was recovered.

Step 3:

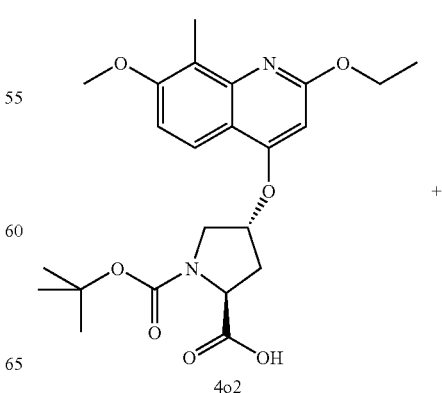

-continued

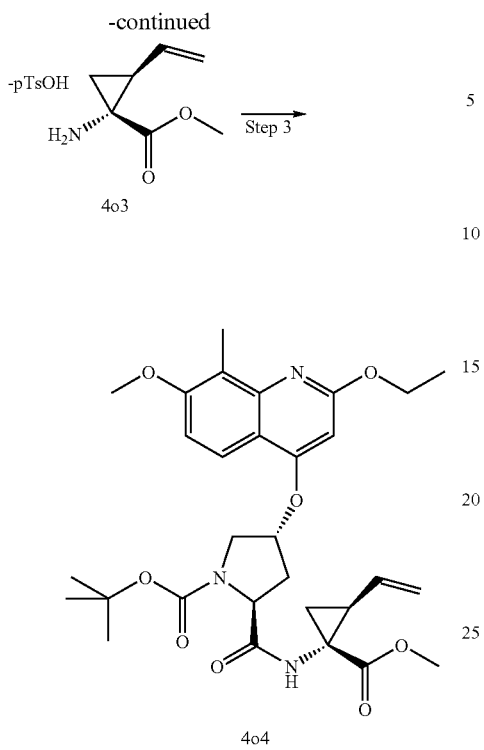

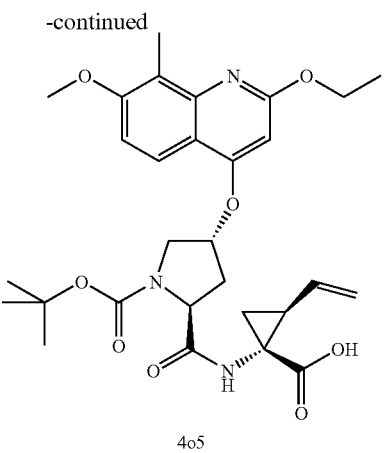

To the dipeptide ester 4o4 (293 mg, 0.51 mmol), dissolved in 7 mL of a mixture of THF:$H_2O$ (2.5:1), was added 2.6 mL of NaOH 1M (2.60 mmol, 5.0 eq). 2 mL of MeOH was subsequently added to clarified the solution, which was then stirred at RT for 4 hours. The solvents were removed in vacuo. The residue was diluted with $H_2O$ and acidified to pH~6 with HCl 1M. This aqueous layer was then extracted three times with EtOAc, dried over $MgSO_4$, filtered and concentrated under vacuum. 271 mg (94% yield) of 4o5 was recovered.

Step 5:

To the acid 4o2 (230 mg, 0.52 mmol), in 5 mL of $CH_3CN$, was added HATU (208 mg, 0.55 mmol, 1.06 eq). To the salt of the amine 4o3 (180 mg, 0.57 mmol, 1.11 eq), in 5 mL of $CH_3CN$, was added DIEA (0.45 mL, 2.58 mmol, 5.0 eq). This amine solution was added to the acid solution and the resulting reaction was allowed to react at RT overnight. The reaction mixture was concentrated to dryness. The residue, dilute with EtOAc, was washed with saturated sodium bicarbonate X2 and brine, dried over $MgSO_4$, filtered and concentrated under vacuum to provide 362 mg of the crude product 4o4 which was used as is in the next step.

Step 4:

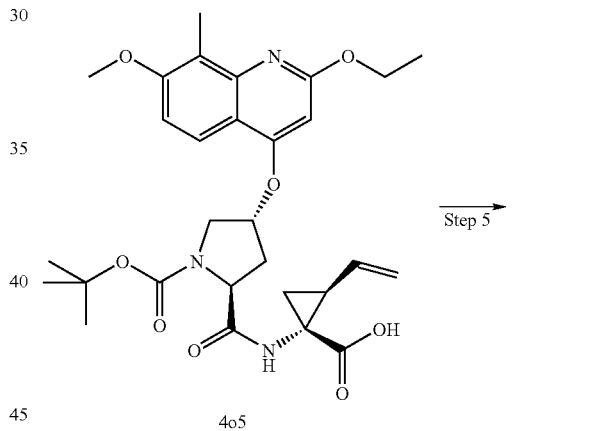

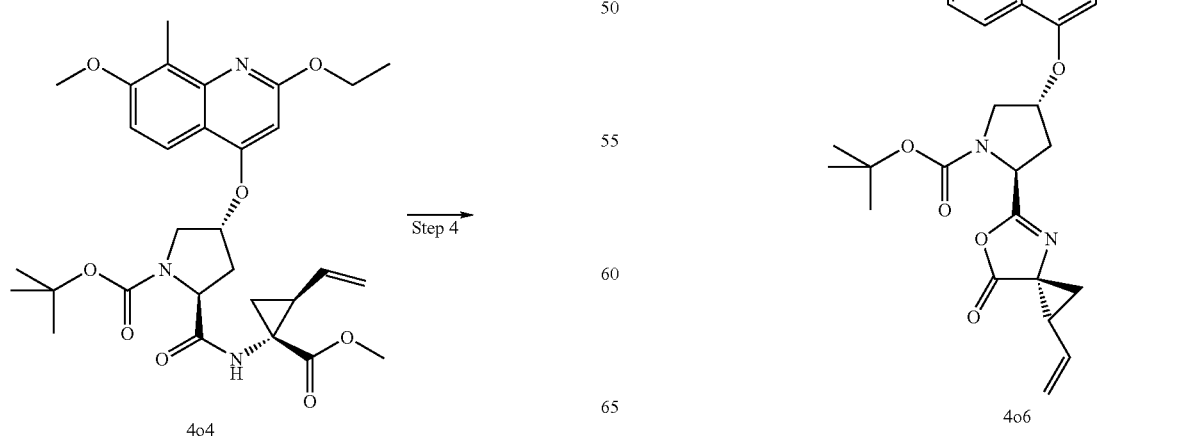

To a solution of the acid 4o5 (270 mg, 0.49 mmol), in 10 mL of CH$_2$Cl$_2$, was added 0.2 mL of Et$_3$N (1.43 mmol, 2.94 eq). This solution was then cooled to 0° C. before addition of isobutyl chloroformate (0.095 mL, 0.73 mmol, 1.50 eq). The ice bath was removed one hour later and stirring was continued for another 4 hours. The solvent was partially removed in vacuo. The crude material was then purified by flash column chromatography with Hexanes/EtOAc; 75:25 to provide 185 mg of the desired compound 4o6 (70% yield).

Step 6:

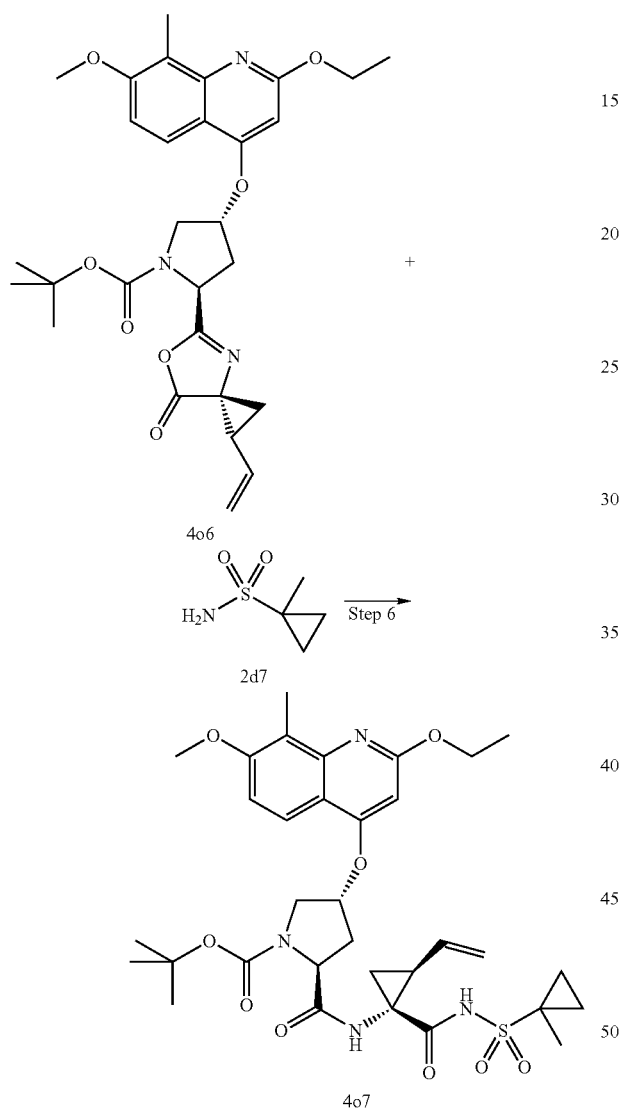

A solution of the sulphonamide 2d7 (15 mg, 0.111 mmol, 1.5 eq), in 1.5 mL of THF, was cooled down to −15° C. for the addition of LiHMDS 1M in THF (0.090 mL, 0.090 mmol, 1.2 eq). The resulting yellow solution was stirred 5 minutes at this temperature and 20 minutes at room temperature. The reaction was then cooled back to −15° C. and a solution of the azalactone 4o6 (40 mg, 0.074 mmol, 1 eq), in 1.5 mL of THF, was added. The resulting solution was stirred 20 minutes at −15, −10° C. then 3 hours at room temperature. The solvent was removed in vacuo. The residue, dilute with H$_2$O, was acidified to pH~6 with HCl 1M. This aqueous layer was then extracted twice with EtOAc, dried over MgSO$_4$, filtered and concentrated under vacuum. 41 mg (81% yield) of the crude material 4o7 was isolated.

Steps 7 and 8:

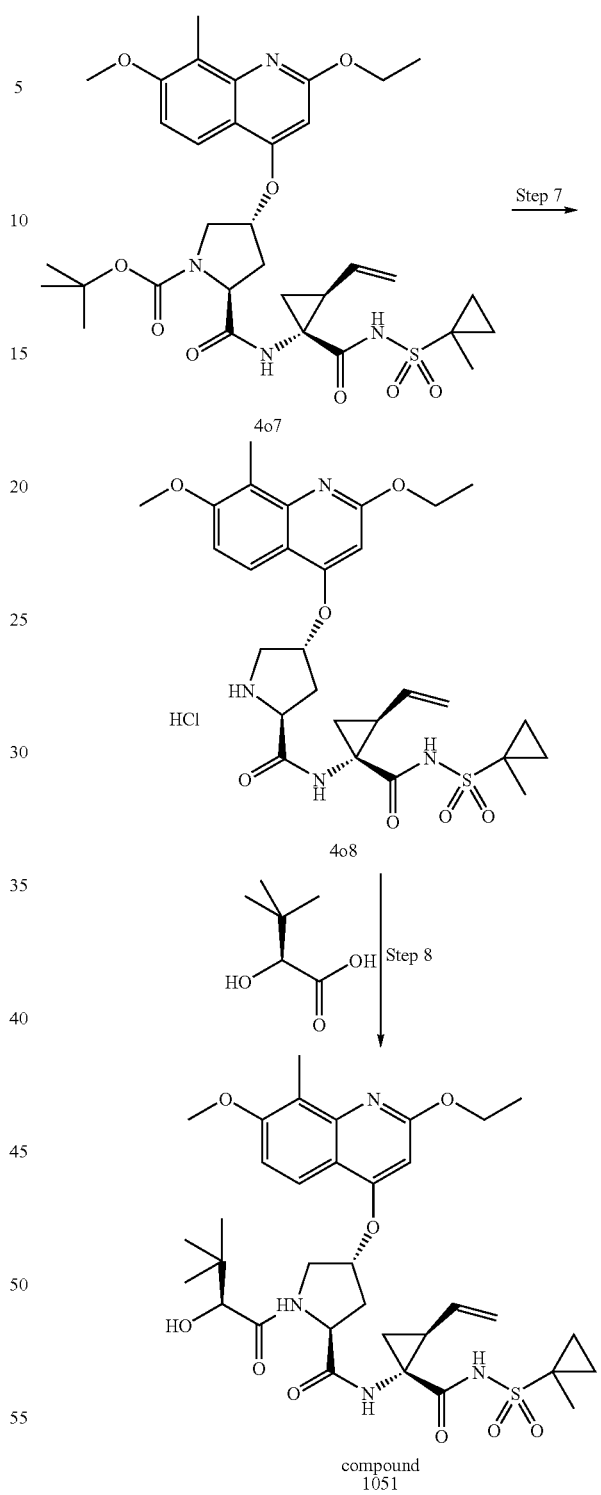

Boc-deprotection of 4o7 to afford the HCl salt of 4o8, and subsequent coupling with (S)-2-hydroxy-3,3-dimethylbutyric acid was carried out following the procedure in steps 4 and 5 of Example 4N above to afford the product compound 1051. $^1$H NMR (400 MHz, DMSO-d$_6$): ca, 9:1 mixture of rotamers, major isomer description; δ 10.40 (s, 1H), 8.97 (s, 1H), 7.75 (d, J=9.0 Hz, 1H), 7.18 (d, J=9.2 Hz, 1H), 6.37 (s, 1H), 5.61-5.50 (m, 1H), 5.40-5.35 (m, 1H), 5.27-5.20 (m, 1H), 5.11-5.06 (m, 1H), 4.46 (q, J=7.1 Hz, 2H), 4.47-4.39 (m, 1H), 4.29-4.23 (m, 1H), 3.94-3.86 (m, 3H), 3.89 (s, 3H), 2.51-2.41 (m, 1H), 2.42 (s, 3H), 2.19-2.06 (m, 2H), 1.73-1.67 (m, 1H), 1.44-1.27 (m, 3H), 1.38 (s, 3H), 1.37 (t, J=7.0 Hz, 3H), 0.93-0.83 (m, 2H), 0.86 (s, 9H).

M.S. (electrospray): 685.3 (M–H)– 687.3 (M+H)+. Reverse Phase HPLC Homogeneity (0.06% TFA; CH$_3$CN: H$_2$O): 98%.

Example 4P

Synthesis of Compounds 1033-1037 of Table 1 mmol) were added. The mixture was stirred at 20° C. for 1.5 h, then was diluted with dichloromethane, washed with sat. NaHCO$_3$ (aq) and brine, dried (MgSO$_4$), filtered and evaporated to dryness. The residue was purified by flash chromatography (4:1 hexane/EtOAc) to give the THP-protected methyl ester (737 mg, 46.8%). The methyl ester (679 mg, 2.95 mmol) was dissolved in aqueous NaOH (1N, 3.0 mL, 3.0 mmol) and THF (4.0 µL) and the mixture was stirred overnight, and evaporated to dryness to give the THP-protected acid 4p2 (624 mg, 97.9%), which was used as is in the next step.

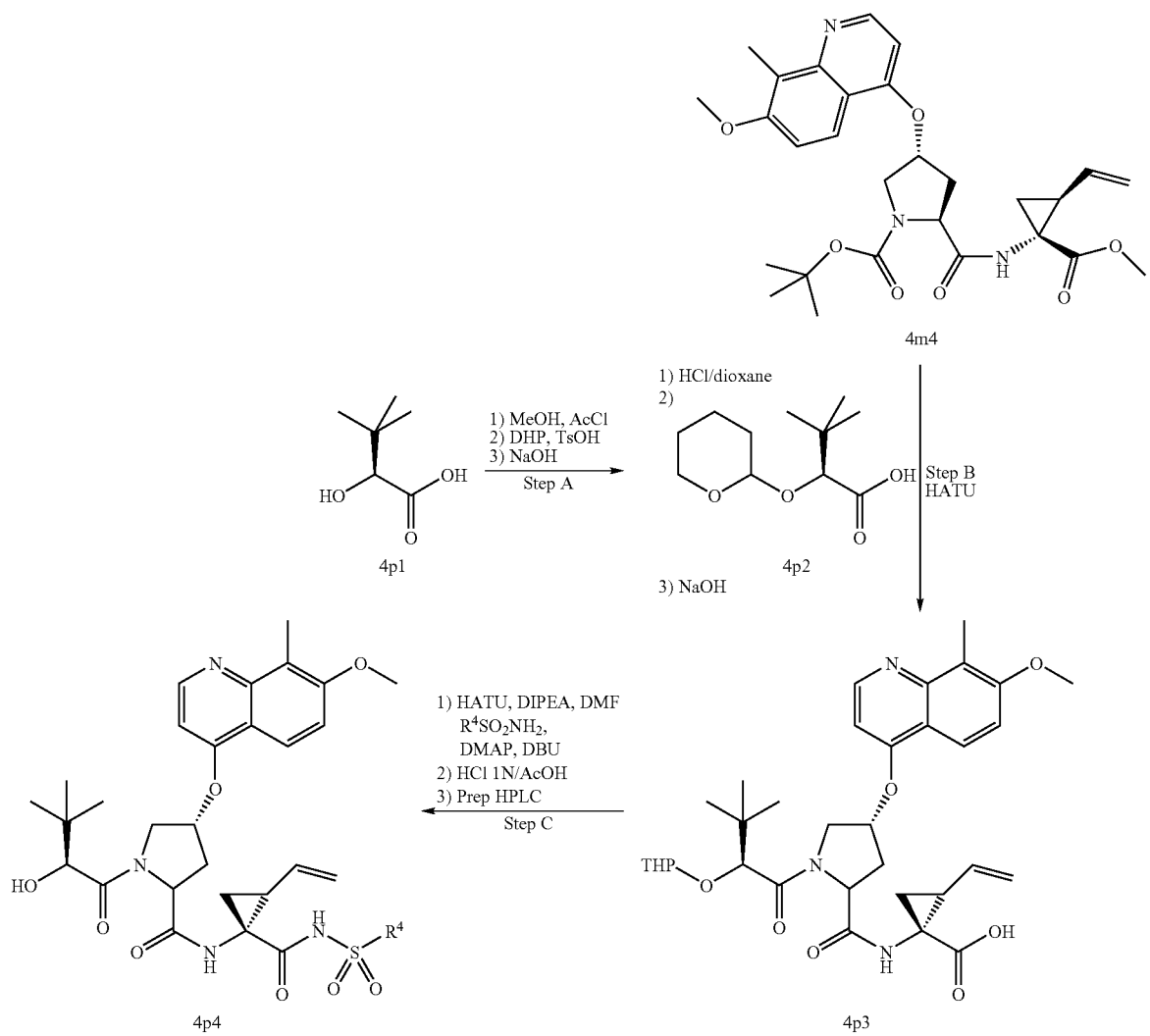

Step A:

(S)-2-Hydroxy-3,3-dimethylbutanoic acid 4 µl (2.00 g, 15.1 mmol) was dissolved in methanol (4.0 mL) and acetyl chloride (109 µL, 1.5 mmol) was added. The mixture was heated 4 h at 70° C., then evaporated to dryness. The residue was extracted with EtOAc and the extract was washed with sat. NaHCO$_3$ (aq), dried over MgSO$_4$, filtered and evaporated to dryness to give the methyl ester (1.38 g, 62.4%). The methyl ester (1.0 g, 6.84 mmol) was dissolved in dichloromethane (5.0 mL) and dihydropyran (3.12 mL, 34.2 mmol) and p-toluenesulfonic acid monohydrate (130 mg, 0.684

Step B:

Compound 4m4 (Example 4M) (841 mg, 1.60 mmol) was dissolved in HCl/dioxane (4M, 15.0 mL) and stirred for 1 h at room temperature. The mixture was evaporated to dryness and the residue was dissolved in DMF (6.0 mL). To this mixture was added DIPEA (1.105 mL, 6.34 mmol), acid 4p2 (509 mg, 2.36 mmol), and HATU (912 mg, 2.40 mmol) and the mixture was stirred overnight at RT. The mixture was evaporated to dryness and the residue was dissolved in EtOAc, The solution was washed with sat. NaHCO$_3$ (aq), dried (MgSO$_4$) and evaporated to dryness to give the crude coupled product methyl ester which was purified by flash chromatography (EtOAc/MeOH/TEA, 97:3:1) to give the purified product (563 mg). This product was allowed to react with aqueous NaOH (1N, 923 µL, 0.923 mmol) in a mixture of MeOH and THF for 18 h at RT, then the mixture was evaporated to dryness. The residue was dissolved in a mixture of water and EtOAc, and the mixture was acidified to pH 4 by addition of KHSO$_3$. The EtOAc extract was dried (MgSO$_4$), filtered and evaporated to dryness to give the product 4p3 (291 mg, 26.4%).

Step C:

Note: the reaction was performed on a solid phase synthesizer (Advanced Chemtech ACT 396), using the 96-wells block. A series of 8-mL vials were disposed in a reaction block. In each vial was successively added the acid 4p3 (18.3 mg, 0.03 mmole), DMF (1 mL), HATU (0.036 mmol, 13.7 mg) and DIPEA (0.15 mmol, 26 µL). All reactions mixtures were allowed to react 1 h. An HPLC of each activated ester was recorded. In each vial was added the R$^4$-sulfonamide (R$^4$—SO$_2$—NH$_2$) (0.06 mmol) and DMAP (0.06 mmol, 7.3 mg). After shaking for 3 h, DBU (0.06 mmol, 9 µL) was added to each vial.

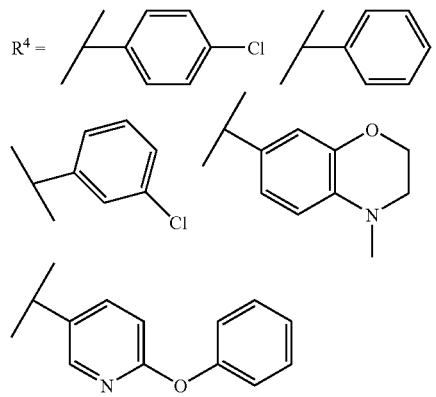

All the vials were treated with 1N aq. HCl (200 µL) and AcOH (400 µL) for 18 h. All compounds were purified by semi-prep reversed-phase HPLC (Symmetry column 5 cm×19 cm, CH$_3$CN/H$_2$O 0.06% TFA gradient).

Example 4Q

Synthesis of Compound 1032 of Table 1

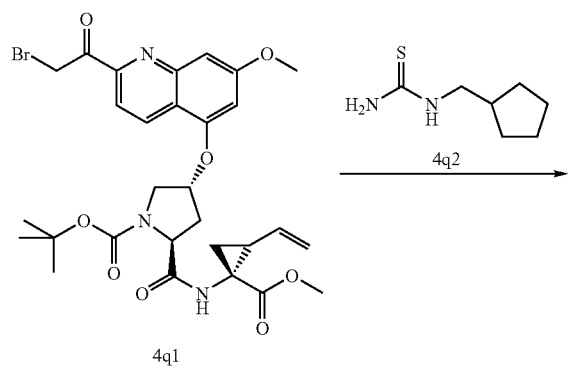

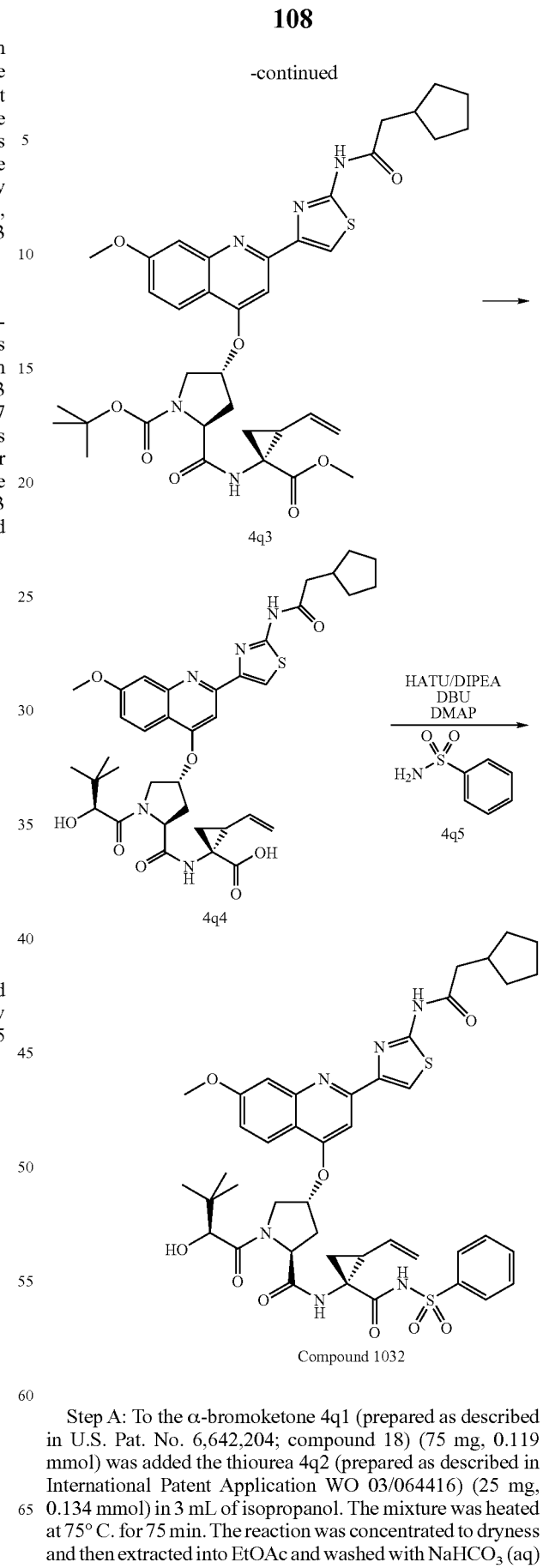

Step A: To the α-bromoketone 4q1 (prepared as described in U.S. Pat. No. 6,642,204; compound 18) (75 mg, 0.119 mmol) was added the thiourea 4q2 (prepared as described in International Patent Application WO 03/064416) (25 mg, 0.134 mmol) in 3 mL of isopropanol. The mixture was heated at 75° C. for 75 min. The reaction was concentrated to dryness and then extracted into EtOAc and washed with NaHCO$_3$ (aq)

(2×) followed by saturated brine. The organic phase was dried over MgSO₄, filtered and concentrated to give the desired product 4q3 as a solid (82 mg, 96%) which was used as is in the next step.

Step B: The aminothiazolyl intermediate 4q3 (82 mg, 0.114 mmol) was first Boc deprotected with 4N HCl/dioxane (3 mL) at RT for 1.5 h. The mixture was concentrated to dryness and placed under vacuum to furnish the HCl salt. This was used directly in the coupling step. The HCl salt (74 mg, 0.113) was combined with (S)-2-hydroxy-3,3-dimethylbutyric acid (30 mg, 0.227 mmol) in DMF (1 mL). To this solution was added DIPEA (0.10 mL, 0.57 mmol) followed by a solution of 1,3-diisopropylcarbodiimide (0.036 mL, 0.234 mmol) and 1-hydroxy-7-azabenzotriazole (HOAt, 31 mg, 0.228 mmol) in DMF (0.5 mL). The reaction was allowed to stir 16 h at RT before the methyl ester was hydrolyzed in situ with the addition of LiOH (76 mg, 1.81 mmol) in H₂O (and MeOH (0.25 mL). The mixture was stirred 16 h before being quenched with AcOH (0.2 mL). The entire mixture was purified by preparative HPLC to afford after lyophilization the desired terminal acid 4q4 as a white solid (26 mg, 32%). MS: (M+H)⁺; 720.3 and (M−H)⁻; 718.3. Analytical HPLC Purity (99%). ¹H NMR of major rotamer 4:1 ratio (DMSO-d₆, 400 MHz) δ 12.4 (s, 1H), 8.60 (s, 1H), 8.25 (bs, 1H), 8.01 (d, J=9 Hz, 1H), 7.58 (bs, 1H), 7.49 (bs, 1H), 7.29 (bs, 1H), 5.73 (dt, J=18, 10 Hz, 1H), 5.54 (bs, 1H), 5.20 (dd, J=18, 1 Hz, 1H), 5.07 (dd, J=12, 1 Hz, 1H), 4.50 (dd, J=7, 7 Hz, 1H), 4.30 (bd, J=12 Hz, 1H), 3.95 (s, 3H), 3.95-3.80 (m, 2H), 2.35-2.21 (m, 2H), 2.08 (s, 2H), 2.07-1.95 (m, 1H), 1.82-1.71 (m, 2H), 1.66-1.48 (m, 5H), 1.33-1.27 (m, 1H), 1.25-1.15 (m, 4H), 0.99 (s, 9H).

Step C: To the terminal acid 4q4 (7.5 mg, 0.01 mmol) in anhydrous DMF (2 mL) was added HATU (4.56 mmol) and DIPEA (8.7 µL, 0.05 mmol). After 60 min, benzenesulfonamide 4q5 (6.3 mg, 0.04 mmol) was added with DBU (6 µL, 0.04 mmol) and DMAP (5.5 mg, 0.045 mmol). The reaction was stirred 16 h at RT. The mixture was concentrated to dryness and purified by preparative HPLC to afford after lyophilization the desired product (compound 1032) as a white solid, 0.57 mg (7%). Homogeneity by analytical HPLC=100% (t_R=6.58 min). MS: (M+H)⁺; 859.4 and (M−H)⁻; 857.4.

Example 4R

Synthesis of Compound 1090 of Table 1

Using the procedure of Example 4O, but using quinoline 1o2 instead of quinoline 1m3 in Step 1, compound 1090 was obtained.

¹H NMR (400 MHz, DMSO-d₆): ca, 90:10 mixture of rotamers, major isomer description; δ 10.41 (s, 1H), 8.96 (s, 1H), 7.89 (d, J=9.2 Hz, 1H), 7.31 (d, J=9.2 Hz, 1H), 6.49 (s, 1H), 5.62-5.51 (m, 1H), 5.44-5.39 (m, 1H), 5.28-5.21 (m, 1H), 5.13-5.08 (m, 1H), 4.52 (q, J=6.6 Hz, 2H), 4.47-4.41 (m, 1H), 4.31-4.26 (m, 1H), 3.97 (s, 3H), 3.98-3.88 (m, 2H), 2.50-2.44 (m, 1H), 2.20-2.08 (m, 2H), 1.74-1.69 (m, 1H), 1.40 (t, J=6.9 Hz, 3H), 1.39 (s, 3H), 1.45-1.28 (m, 3H), 0.95-0.84 (m, 2H), 0.86 (s, 9H).

M.S. (electrospray): 749.1 (M−H)− 751.1 (M−H)− 751.2 (M+H)+ 753.2 (M+H)+. Reverse Phase HPLC Homogeneity (0.06% TFA; CH₃CN: H₂O): 97%

Example 4S

Synthesis of Compound 1100 of Table 1

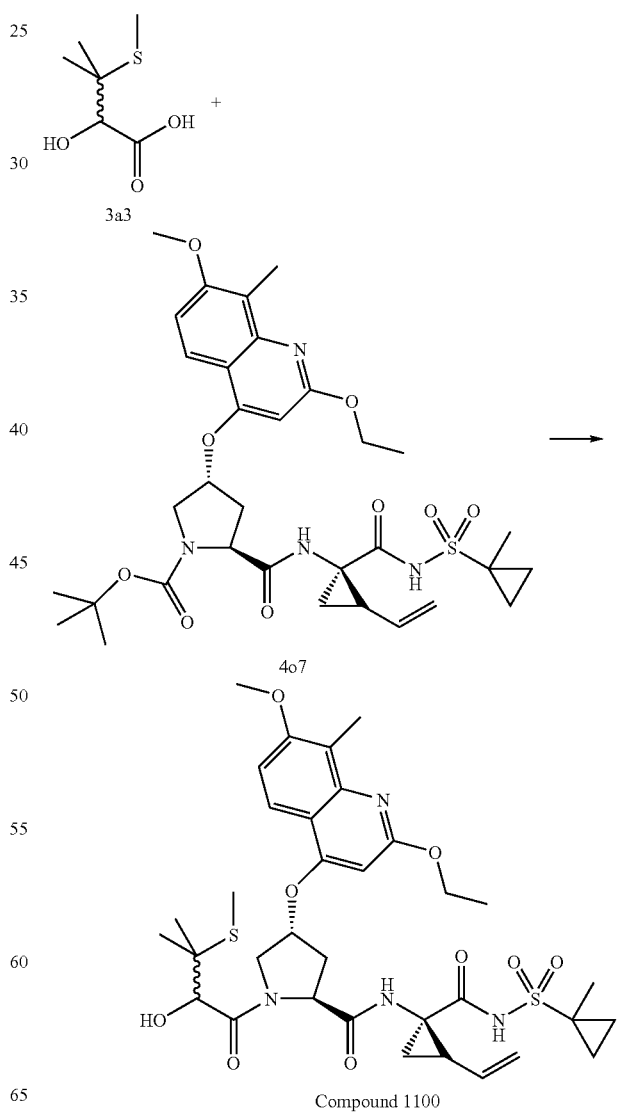

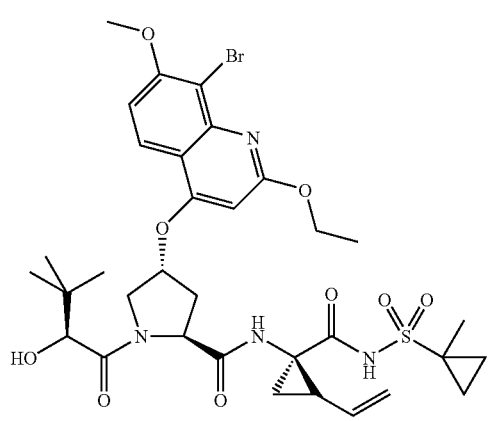

Compound 1090

A mixture of compound 4o7 (Example 4O) (35 mg, 0.052 mmol) and 2 mL of 4M HCl/dioxane, was stirred at room temperature for 1 hour. The solvent was evaporated and the residue was dried under vacuum. To a solution of the acid 3a3 (11.7 mg, 0.071 mmol, 1.4 equiv.), the amine (0.052 mmol) and DIEA (0.050 mL, 0.29 mmol, 5.5 equiv.) in 0.5 mL of DMF was added a solution of DIC-HOAt (0.013 mL, 0.080 mmol, 1.5 equiv. –11.6 mg, 0.085 mmol, 1.6 equiv.) in 0.5 mL of DMF. The resulting solution was stirred at room temperature overnight, then diluted with AcOH and purified by preparatory HPLC (YMC Combiscreen ODS-AQ, 50×20 mm ID S-5 micron, 120A; 220 nm) using a linear gradient and 0.06% TFA $CH_3CN/H_2O$. The pure fractions were combined, concentrated and lyophilized to provide the product (compound 1100) as the TF salt (12 mg, 32%).

$^1$H NMR (400 MHz, DMSO-$d_6$): ca, 70:30 mixture of isomers (epimers at the capping group), major isomer description; δ 10.23 (s, 1H), 8.93 (s, 1H), 7.76 (d, J=9.2 Hz, 1H), 7.21 (d, J=9.2 Hz, 1H), 6.38 (s, 1H), 5.68-5.56 (m, 1H), 5.48-5.44 (m, 1H), 5.29-5.22 (m, 1H), 5.13-5.08 (m, 1H), 4.47 (q, J=7.0 Hz, 2H), 4.44-4.38 (m, 1H), 4.21-4.16 (m, 1H), 4.03-3.97 (m, 1H), 3.90 (s, 3H), 3.92-3.88 (m, 1H), 2.56-2.47 (m, under DMSO, 1H), 2.44 (s, 3H), 2.24-2.14 (m, 2H), 1.95 (s, 3H), 1.74-1.69 (m, 1H), 1.40 (s, 3H), 1.38 (t, J=7.0 Hz, 3H), 1.47-1.30 (m, 3H), 1.24 (s, 3H), 1.22 (s, 3H), 0.97-0.87 (m, 2H).

M.S. (electrospray): 717.3 (M−H)− 719.3 (M+H)+. Reverse Phase HPLC Homogeneity (0.06% TFA; $CH_3CN$: $H_2O$): 99%

Example 4T

Synthesis of Compound 1057 from Table 1

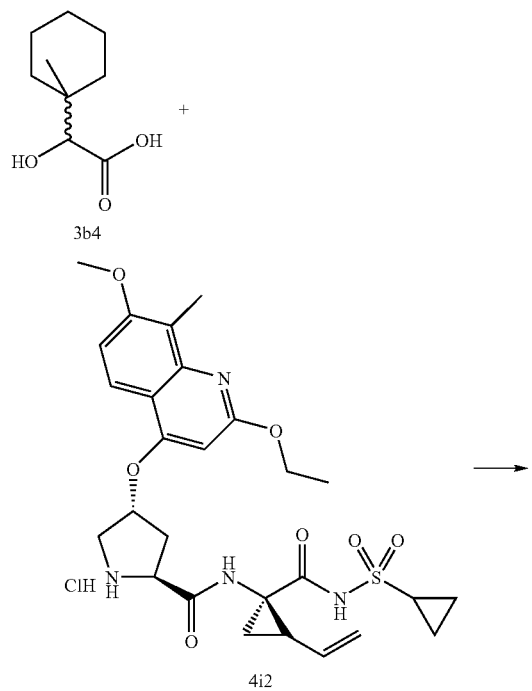

-continued

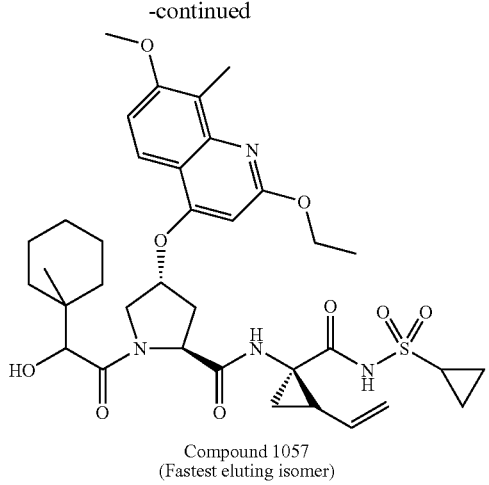

Compound 1057
(Fastest eluting isomer)

To a solution of the acid 3b4 (9 mg, 0.052 mmol, 1.4 equiv.), the amine 4i2 (0.038 mmol) and DIEA (0.030 mL, 0.17 mmol, 4.5 equiv.), in 0.5 mL of DMF, was added a solution of DIC-HOAt (0.009 mL, 0.057 mmol, 1.5 equiv. –8 mg, 0.059 mmol, 1.55 equiv.) in 0.5 mL of DMF. The resulting solution was stirred at room temperature overnight. The reaction mixture was diluted with AcOH and purified by preparatory HPLC (YMC Combiscreen ODS-AQ, 50×20 mm ID S-5 micron, 120A; 220 nm) using a linear gradient and 0.06% TFA $CH_3CN/H_2O$. The pure fractions were combined, concentrated and lyophilized to provide the product compound 1057 as the TF salt. The fastest eluting compound (7 mg, 26%) showed the following NMR.

$^1$H NMR (400 MHz, DMSO-$d_6$): ca, 95:5 mixture of rotamers, major isomer description; δ 10.52 (s, 1H), 8.99 (s, 1H), 7.74 (d, J=9.0 Hz, 1H), 7.17 (d, J=9.2 Hz, 1H), 6.37 (s, 1H), 5.67-5.56 (m, 1H), 5.39-5.35 (m, 1H), 5.27-5.21 (m, 1H), 5.12-5.07 (m, 1H), 4.46 (q, J=7.1 Hz, 2H), 4.43-4.38 (m, 1H), 4.30-4.24 (m, 1H), 3.93-3.86 (m, 2H), 3.88 (s, 3H), 2.93-2.85 (m, 1H), 2.54-2.44 (m, under DMSO, 1H), 2.42 (s, 3H), 2.19-2.06 (m, 2H), 1.75-1.69 (m, 1H), 1.37 (t, J=7.1 Hz, 3H), 1.44-1.13 (m, 10H), 1.12-0.98 (m, 5H), 0.80 (s, 3H).

M.S. (electrospray): 711.3 (M−H)− 713.4 (M+H)+. Reverse Phase HPLC Homogeneity (0.06% TFA; $CH_3CN$: $H_2O$): 98%

Example 4U

Synthesis of Compound 1078 of Table 1

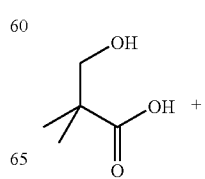

-continued

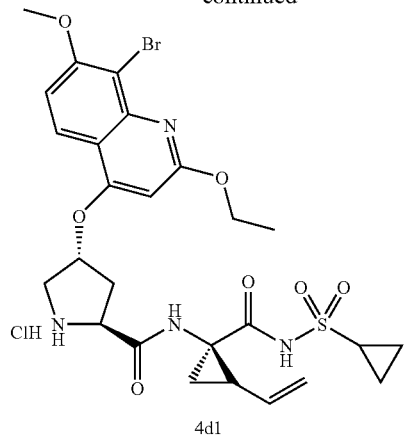

4d1

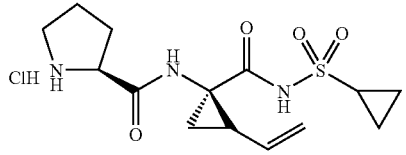

Compound 1078

To a solution of 2,2-dimethyl-3-hydroxypropionic acid (1.25 eq, 7.21 mg), amine 4d1 (1 eq, 40 mg) and DIPEA (5 eq, 53 μL) in DMF (1 mL), was added the solution of DIC-HOAT (1.4 eq each, 13.3 μL and 11.6 mg respectively) in DMF (1 mL). The reaction mixture was stirred at room temperature for 12 h, then was filtered through Millex filter and purified by preparative HPLC (Combiprep ODS-AQ, 20×50 mm) to afford after lyophilization compound 1078 as a white amorphous solid (14.5 mg, 37%). Reverse Phase HPLC Homogeneity (0.06% TFA; CH$_3$CN: H$_2$O): 96% $^1$H NMR (DMSO-d$_6$, 400 MHz): 10.49 (s, 1H); 8.77 (s, 1H); 7.89 (d, J=9 Hz, 1H); 7.31 (d, J=9.2 Hz, 1H); 6.53 (s, 1H); 5.64-5.55 (m, 1H); 5.44 (broad s, 1H); 5.27 (d, J=17 Hz, 1H); 5.11 (d, J=10.4 Hz, 1H); 4.55-4.47 (m, 3H); 4.39-4.34 (m, 1H); 4.28 (d, J=12.1 Hz, 1H); 4.03-3.94 (m, 4H); 3.50 (d, J=11 Hz, 1H); 3.40 (d, J=11 Hz, 1H); 2.94-2.91 (m, 1H); 2.42-2.37 (m, 1H); 2.19-2.08 (m, 2H); 1.72 (dd, J=5.1 Hz, J=7.9 Hz, 1H); 1.40 (t, J=7.2 Hz, 3H); 1.27 (dd, J=5.1 Hz, J=9.4 Hz, 1H); 1.11-1.03 (m, 10H); MS: (M+H)$^+$: 723; (MH+2)$^+$: 725.

Example 4V

Synthesis of Compound 1084 of Table 1

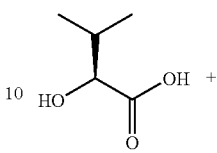

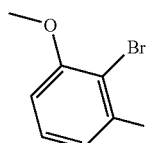

4d1

Compound 1084

Using the procedure of Example 4U but using 2-hydroxy-3-methylbutanoic acid in place of 2,2-dimethyl-3-hydroxypropionic acid, compound 1084 was obtained as a white amorphous solid (15.4 mg, 39%). Reverse Phase HPLC Homogeneity (0.06% TFA; CH$_3$CN: H$_2$O): 97%; $^1$H NMR (DMSO-d$_6$, 400 MHz): δ10.54 (s, 1H); 9.09 (s, 1H); 7.91 (d, J=9.2 Hz, 1H); 7.30 (d, J=9.2 Hz, 1H); 6.49 (s, 1H); 5.69-5.60 (m, 1H); 5.44 (broad s, 1H); 5.26 (d, J=17 Hz, 1H); 5.12 (d, J=10.4 Hz, 1H); 4.51 (q, J=6.9 Hz, 3H); 4.41 (dd, J=6.8 Hz, J=10.5 Hz, 2H); 4.18 (d, J=12.6 Hz, 1H); 3.97 (s, 3H); 3.94-3.91 (m, 2H); 2.93-2.89 (m, 1H); 2.19-2.13 (m, 2H); 1.95-1.90 (m, 1H); 1.73 (dd, J=5.2 Hz, J=8 Hz, 1H); 1.40 (t, J=7 Hz, 3H); 1.34 (dd, J=5 Hz, J=9.4 Hz, 1H); 1.11-1.03 (m, 4H); 0.84 (d, J=6.9 Hz, 3H); 0.78 (d, J=6.6 Hz, 3H).

MS: (M+H)$^+$: 723; (MH+2)$^+$: 725.

Example 4W

Synthesis of Compound 1105 of Table 1

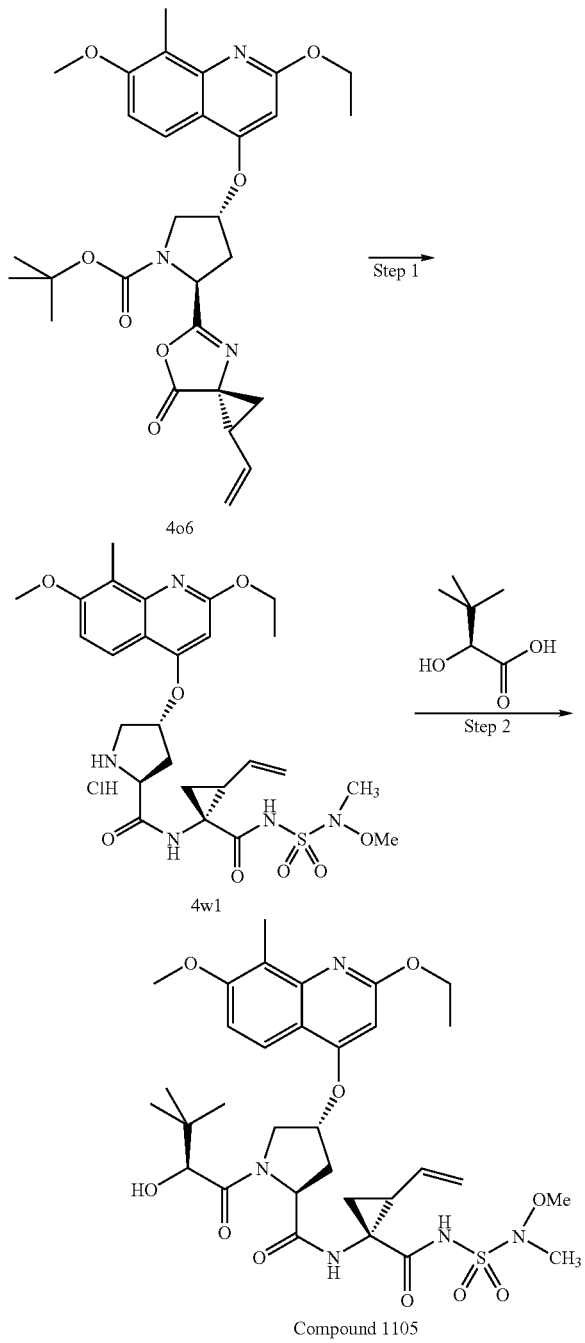

Step 1:
Compound 4w1 was synthesized from compound 4o6 using the procedures described in Example 4N, steps 3 and 4, but using N-methoxy-N-methylsulfamide instead of N,N-dimethylsulfamide.

Step 2:
To a solution of S-2-hydroxy-3,3-dimethylbutyric acid (24 mg, 0.18 mmol), the amine 4w1 (90 mg, 0.147 mmol) and DIPEA (127.6 μL, 0.733 mmol), in 1 mL of DMF, was added a solution of DIC (32 μL, 0.074 mmol) HOAt (11 mg, 0.074 mmol) in 0.75 mL of DMF. The resulting solution was stirred at room temperature 12 h. The reaction mixture was diluted with AcOH and purified by prep HPLC (YMC Combiscreen ODS-AQ, 50×20 mm ID S-5 micron, 120A; 220 nm) using a linear gradient and 0.06% TFA $CH_3CN/H_2O$. The pure fractions were combined, concentrated and lyophilized to provide compound 1105 as the trifluoroacetate salt (32 mg, 32%). Reverse Phase HPLC Homogeneity (0.06% TFA; $CH_3CN$:$H_2O$): 99%; $^1$HNMR (DMSO-$d_6$, 400 MHz) –δ10.78 (s, 1H), 8.94 (s, 1H), 7.75 (d, J=9 Hz, 1H), 7.19 (d, J=9 Hz, 1H), 6.38 (s, 1H), 5.61-5.52 (m, 1H), 5.39 (bs, 1H), 5.25 (d, J=17 Hz, 1H), 5.12 (d, J=10 Hz, 1H), 4.49-4.41 (m, 3H), 4.26 (d, J=13 Hz, 1H), 3.95-3.85 (m, 5H), 3.65 (s, 3H), 2.94 (s, 3H), 2.40-2.55 (m, 4H), 2.20-2.10 (m, 2H), 1.72-1.69 (m, 1H), 1.38 (t, J=7 Hz, 3H), 1.35-1.31 (m, 1H), 0.87 (s, 9H); EIMS: (M+H)=692.0, (M–H)=691.0.

Example 5

NS3-NS4A Protease Assay

The enzymatic assay used to evaluate the present compounds is described in WO 00/09543 and WO 00/59929.

Example 6

Cell-Based Luciferase Reporter HCV RNA Replication Assay

Cell Culture:
Huh-7 cells with a stable subgenomic HCV replicon that encodes a modified luciferase reporter gene (expressed as a luciferase-FMDV2A-neomycin phosphotransferase fusion gene) were established as previously described (Lohman et al., 1999. Science 285: 110-113; Vroljik et al., 2003 J. Virol Methods 110:201-209.), with the exception that replicon cells were selected with 0.25 mg/mL G418. The amount of luciferase expressed by selected cells directly correlates with the level of HCV replication. These cells, designated as MP-1 cells, are maintained in Dulbecco's Modified Earle Medium (DMEM) supplemented with 10% FBS and 0.25 mg/mL neomycin (standard medium). The cells are passaged by trypsinization and frozen in 90% FBS/10% DMSO. During the assay, DMEM medium supplemented with 10% FBS, containing 0.5% DMSO and lacking neomycin, was used (Assay medium). The day of the assay, MP-1 cells are trypsinized and diluted to 100 000 cells/mL in assay medium. 100 μL is distributed into each well of a black 96-well View-Plate™ (Packard). The plate is then incubated at 37° C. with 5% $CO_2$ for two hours.

Reagents and Materials:

| Product | Company | Catalog # | Storage |
|---|---|---|---|
| DMEM | Wisent Inc. | 10013CV | 4° C. |
| DMSO | Sigma | D-2650 | RT |
| Dulbecco's PBS | Gibco-BRL | 14190-136 | RT |
| Fetal Bovine Serum | Bio-Whittaker | 14-901F | −20° C./4° C. |
| Geneticin (G418) | Gibco-BRL | 10131-027 | −20° C./4° C. |
| Trypsin-EDTA | Gibco-BRL | 25300-054 | −20° C./4° C. |
| ViewPlate ™-96, Black | Packard | 6005182 | RT |
| Backing tape, Black | Packard | 6005189 | RT |
| PVDF 0.22 μm Filter Unit | Millipore | SLGV025LS | RT |
| Deep-Well liter Plate Polypropylene | Beckman | 267007 | RT |

Preparation of Test Compound:
The test compound in 100% DMSO was first diluted in assay medium to a final DMSO concentration of 0.5%. The solution was sonicated for 15 min and filtered through a 0.22 μM Millipore Filter unit. Into column 3 of a Polypropylene Deep-Well Titer Plate, the appropriate volume is transferred into assay medium to obtain the starting concentration (2×) to be tested. In columns 2 and 4 to 12, add 200 μL of assay medium (containing 0.5% DMSO). Serial dilutions (½) are prepared by transferring 200 μL from column 3 to column 4, then from column 4 to column 5, serially through to column 11. Columns 2 and 12 are the no inhibition controls.

Addition of Test Compound to Cells:

A volume of 100 μL from each well of the compound dilution plate is transferred to a corresponding well of the Cell Plate (Two columns will be used as the "No inhibition control"; ten [10] columns are used for the dose response). The cell culture plate was incubated at 37° C. with 5% $CO_2$ for 72 hours.

Luciferase Assay:

Following the 72 h incubation period, the medium is aspirated from the 96-well assay plate and a volume of 100 μL of 1× Glo Lysis Buffer (Promega) previously warmed to room temperature was added to each well. The plate was incubated at room temperature for 10 min with occasional shaking. A black tape was put at the bottom of the plate. 100 μL of Bright-Glo luciferase substrate (Promega) previously warmed to room temperature was added to each well followed by gentle mixing. The luminescence was determined on a Packard Topcount instrument using the Data Mode Luminescence (CPS) with a count delay of 1 min and a count time of 2 sec.

| Product | Company | Catalog # | Storage |
|---|---|---|---|
| Glo Lysis Buffer | Promega | E266A | 4° C. |
| Bright-Glo Luciferase Assay System | Promega | E2620 | −20° C. |

The luminescence determination (CPS) in each well of the culture plate was a measure of the amount of HCV RNA replication in the presence of various concentrations of inhibitor. The % inhibition was calculated with the following equation:

% inhibition=100−[CPS(inhibitor)/CPS(control)×100]

A non-linear curve fit with the Hill model was applied to the inhibition-concentration data, and the 50% effective concentration ($EC_{50}$) was calculated by the use of SAS software (Statistical Software; SAS Institute, Inc. Cary, N.C.).

The compounds of this invention are found to be active when evaluated in the preceding enzymatic and cell based assays.

Example 7

Specificity Assays

The specificity assays used to evaluate the selectivity of compounds according to this invention were performed as described in WO 00/09543 except that the assay buffer for the Elastase assay was comprised of 50 mM Tris-HCl pH 8, 0.25 M NaCitrate, 0.01% n-dodecyl β-d-maltoside, and 5.25% DMSO.

The compounds of formula (I) are found to be selective in that they do not show significant inhibition (no measurable activity at concentrations up to 30 μM) in the Human Leukocyte Elastase or Human Liver Cathepsin B assays.

Tables of Compounds

The following table lists compounds representative of the invention. Many of the compounds listed in Tables 1 and 2 were found to have $IC_{50}$ values below 0.5 μM in the NS3-NS4A protease assay of Example 5. In addition, many of the compounds listed in Tables 1 and 2 have $EC_{50}$ values below 1 μM in the cell-based luciferase reporter HCV RNA replication assay of Example 6. Retention times ($t_R$) for each compound were measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.

TABLE 1

| Cpd | R³ | R² | R⁴ | (MH)⁺ | $t_R$ (min) |
|---|---|---|---|---|---|
| 1001 | O, t-Bu-CH₂-C(=O)- | MeO, Br, quinoline-OEt | cyclopropyl | 721.2/ 723.2 | 6.83 |

TABLE 1-continued

| Cpd | R³ | R² | R⁴ | (MH)⁺ | t_R (min) |
|---|---|---|---|---|---|
| 1002 | methyl ketone (acetyl) | 8-Br-7-MeO-2-OEt-quinolin-4-yloxy | cyclopropyl | 665.0/ 667.1 | 5.52 |
| 1003 | tert-butyl ketone (pivaloyl) | 8-Br-7-MeO-2-OEt-quinolin-4-yloxy | cyclopropyl | 707.0/ 709.2 | 6.55 |
| 1004 | ethyl ketone (propanoyl) | 8-Br-7-MeO-2-OEt-quinolin-4-yloxy | cyclopropyl | 679.0/ 681.1 | 5.88 |
| 1005 | propyl ketone (butanoyl) | 8-Br-7-MeO-2-OEt-quinolin-4-yloxy | cyclopropyl | 693.0/ 695.2 | 6.18 |
| 1006 | isobutyl ketone | 8-Br-7-MeO-2-OEt-quinolin-4-yloxy | cyclopropyl | 707.2/ 709.2 | 6.50 |

TABLE 1-continued

| Cpd | R³ | R² | R⁴ | (MH)⁺ | t_R (min) |
|---|---|---|---|---|---|
| 1007 | CF₃CH₂C(O)- | 8-Br, 7-MeO, 2-OEt quinolin-4-yloxy | cyclopropyl | 705.0/707.2 | 6.17 |
| 1008 | CF₃CH₂C(O)- | 8-Br, 7-MeO, 2-OEt quinolin-4-yloxy | cyclopropyl | 733.1/735.1 | 6.13 |
| 1009 | cyclopentyl-CH₂-C(O)- | 8-Br, 7-MeO, 2-OEt quinolin-4-yloxy | cyclopropyl | 733.2/735.2 | 6.80 |
| 1010 | cycloheptyl-CH₂-C(O)- | 8-Br, 7-MeO, 2-OEt quinolin-4-yloxy | cyclopropyl | 747.0/749.2 | 7.00 |
| 1011 | cyclohexyl-C(O)- | 8-Br, 7-MeO, 2-OEt quinolin-4-yloxy | cyclopropyl | 733.2/735.2 | 6.76 |

TABLE 1-continued

| Cpd | R³ | R² | R⁴ | (MH)⁺ | t_R (min) |
|---|---|---|---|---|---|
| 1012 | cyclopentyl-C(O)-CH- | 8-Br-7-MeO-2-OEt-quinolin-4-yloxy | cyclopropyl | 719.2/ 721.2 | 6.56 |
| 1013 | benzyl-C(O)-CH- | 8-Br-7-MeO-2-OEt-quinolin-4-yloxy | cyclopropyl | 741.0/ 743.2 | 6.33 |
| 1014 | (R)-PhCH(Me)-C(O)- | 8-Br-7-MeO-2-OEt-quinolin-4-yloxy | cyclopropyl | 755.2/ 757.3 | 6.38 |
| 1015 | (S)-PhCH(Me)-C(O)- | 8-Br-7-MeO-2-OEt-quinolin-4-yloxy | cyclopropyl | 755.2/ 757.2 | 6.90 |
| 1016 | Ph-CH₂CH₂-C(O)- | 8-Br-7-MeO-2-OEt-quinolin-4-yloxy | cyclopropyl | 755.2/ 757.2 | 6.73 |

TABLE 1-continued

| Cpd | R³ | R² | R⁴ | (MH)⁺ | t_R (min) |
|---|---|---|---|---|---|
| 1017 | phenyl-C(O)-CH(-)- | 8-Br-7-MeO-2-OEt-4-O- quinoline | cyclopropyl | 727.2/ 729.2 | 6.33 |
| 1018 | 1-phenylcyclopropyl-C(O)-CH(-)- | 8-Br-7-MeO-2-OEt-4-O- quinoline | cyclopropyl | 767.2/ 769.2 | 6.59 |
| 1019 | (thiophen-3-yl)-CH₂-C(O)-CH(-)- | 8-Br-7-MeO-2-OEt-4-O- quinoline | cyclopropyl | 747.1/ 749.1 | 6.25 |
| 1020 | cyclopropyl-C(O)-CH(-)- | 8-Br-7-MeO-2-OEt-4-O- quinoline | cyclopropyl | 691.2/ 693.2 | 5.97 |
| 1021 | MeO-C(O)-CH(-)- | 8-Br-7-MeO-2-OEt-4-O- quinoline | cyclopropyl | 681.0/ 683.2 | 6.20 |

TABLE 1-continued

| Cpd | R³ | R² | R⁴ | (MH)⁺ | t_R (min) |
|---|---|---|---|---|---|
| 1022 | ethyl ester group | 8-Br-7-MeO-2-OEt-quinolin-4-yloxy | cyclopropyl | 695.0/ 697.2 | 6.20 |
| 1023 | isopropyl ester group | 8-Br-7-MeO-2-OEt-quinolin-4-yloxy | cyclopropyl | 709.2/ 711.2 | 6.48 |
| 1024 | 2,2,2-trichloro-1,1-dimethylethyl ester group | 8-Br-7-MeO-2-OEt-quinolin-4-yloxy | cyclopropyl | 825.1/ 827.1 | 7.35 |
| 1025 | tert-butyl amide group | 8-Br-7-MeO-2-OEt-quinolin-4-yloxy | cyclopropyl | 722.2/ 724.2 | 6.31 |
| 1026 | ethyl amide group | 8-Br-7-MeO-2-OEt-quinolin-4-yloxy | cyclopropyl | 694.2/ 696.2 | 5.68 |

TABLE 1-continued

| Cpd | R³ | R² | R⁴ | (MH)⁺ | t_R (min) |
|---|---|---|---|---|---|
| 1027 | isopropyl-NH-C(O)-CH(CH₃)- | 8-Br-7-MeO-2-OEt-quinolin-4-yloxy | cyclopropyl | 708.0/ 710.2 | 5.96 |
| 1028 | thiophen-2-yl-NH-C(O)-CH(CH₃)- | 8-Br-7-MeO-2-OEt-quinolin-4-yloxy | cyclopropyl | 748.2/ 750.2 | 6.16 |
| 1029 | (CH₃)₂N-SO₂-CH(CH₃)- | 8-Br-7-MeO-2-OEt-quinolin-4-yloxy | cyclopropyl | 730.2/ 732.2 | 6.05 |
| 1030 | Et-SO₂-CH(CH₃)- | 8-Br-7-MeO-2-OEt-quinolin-4-yloxy | cyclopropyl | 715.2/ 717.2 | 6.22 |
| 1031 | nPr-SO₂-CH(CH₃)- | 8-Br-7-MeO-2-OEt-quinolin-4-yloxy | cyclopropyl | 729.2/ 731.2 | 6.22 |

TABLE 1-continued

| Cpd | R³ | R² | R⁴ | (MH)⁺ | t_R (min) |
|---|---|---|---|---|---|
| 1032 | tert-butyl hydroxy ketone | cyclopentylacetamido-thiazolyl-(7-methoxy-4-methoxyquinolin-2-yl) | isopropylphenyl | 859.4 | 6.58 |
| 1033 | tert-butyl hydroxy ketone | 7-MeO-8-Me-4-methoxyquinolinyl | 4-chloro-isopropylphenyl | 699.2 | 5.17 |
| 1034 | tert-butyl hydroxy ketone | 7-MeO-8-Me-4-methoxyquinolinyl | isopropylphenyl | 665.3 | 4.59 |
| 1035 | tert-butyl hydroxy ketone | 7-MeO-8-Me-4-methoxyquinolinyl | 3-chlorophenyl | 699.3 | 5.14 |

TABLE 1-continued

| Cpd | R³ | R² | R⁴ | (MH)⁺ | t_R (min) |
|---|---|---|---|---|---|
| 1036 | | 7-MeO, 8-Me quinolin-4-yloxy | 4-methyl-3,4-dihydro-2H-benzo[1,4]oxazin-7-yl | 736.4 | 4.79 |
| 1037 | | 7-MeO, 8-Me quinolin-4-yloxy | 6-phenoxypyridin-3-yl | 758.4 | 4.41 |
| 1038 | | 7-MeO, 8-Me, 2-OEt quinolin-4-yloxy | cyclopropyl | 673.3 | 4.85 |
| 1039 | | 7-MeO, 8-Br, 2-OEt quinolin-4-yloxy | cyclopropyl | 737.3 | 6.24 |
| 1040 | | 8-Cl quinolin-4-yloxy | cyclopropyl | 603.1 | 3.96 |

TABLE 1-continued
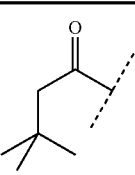
| Cpd | R³ | R² | R⁴ | (MH)⁺ | t_R (min) |
|---|---|---|---|---|---|
| 1041 | 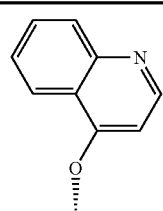 | 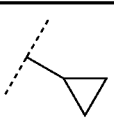 | 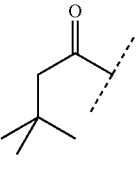 | 569.1 | 3.77 |
| 1042 | 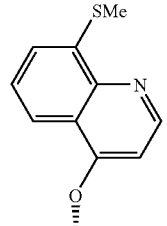 | 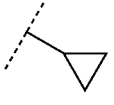 | 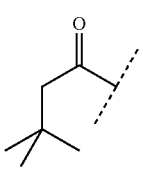 | 615.1 | 4.15 |
| 1043 | 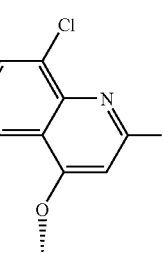 | 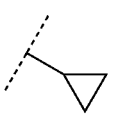 | 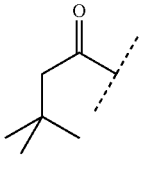 | 647.1 | 6.86 |
| 1044 | 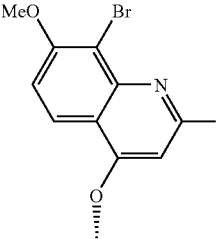 | 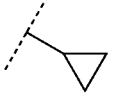 | 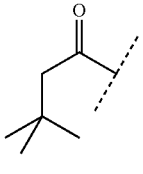 | 677.1 | 6.28 |
| 1045 | 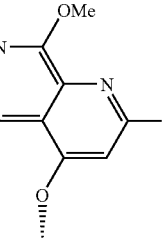 | 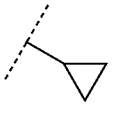 | | 644.2 | 5.40 |

TABLE 1-continued

| Cpd | R³ | R² | R⁴ | (MH)⁺ | $t_R$ (min) |
|---|---|---|---|---|---|
| 1046 | neopentyl ketone | 8-SMe, 2-OEt quinoline (4-O linkage) | cyclopropyl | 659.3 | 6.66 |
| 1047 | neopentyl ketone | 6-MeO isoquinoline (1-O linkage) | cyclopropyl | 599.3 | 5.62 |
| 1048 | BrCH₂-C(Me)₂-CH₂-C(O)- | 7-MeO, 8-Br, 2-OEt quinoline (4-O linkage) | cyclopropyl | 785.1 787.1 | 6.40 |
| 1049 | HO-CH(tBu)-C(O)- | 7-MeO, 8-Me quinoline (4-O linkage) | NMe₂ | 632.3 | 3.60 |
| 1050 | HO-CH(tBu)-C(O)- | 7-MeO, 8-Me quinoline (4-O linkage) | 2,5-dihydropyrrol-1-yl | 656.3 | 3.88 |

TABLE 1-continued
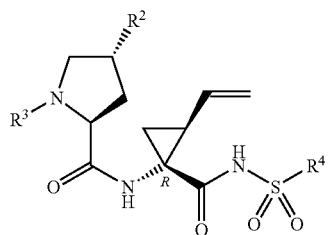
| Cpd | R³ | R² | R⁴ | (MH)⁺ | t_R (min) |
|---|---|---|---|---|---|
| 1051 | (CH₃)₃C-CH(OH)-C(=O)- | 7-MeO, 8-Me, 2-OEt quinoline-4-yloxy | cyclopropyl | 687.3 | 4.79 |
| 1052 | (CH₃)₃C-CH(OH)-C(=O)- | 7-MeO, 8-Me, 2-OEt quinoline-4-yloxy | 1-(but-3-enyl)cyclopropyl | 727.4 | 5.82 |
| 1053 | (CH₃)₃C-CH(OH)-C(=O)- | 7-MeO, 8-Me, 2-OEt quinoline-4-yloxy | 1-benzylcyclopropyl | 763.4 | 5.85 |
| 1054 | (tetrahydropyran-4-yl)-CH₂-C(=O)- | 7-MeO, 8-Br, 2-OEt quinoline-4-yloxy | cyclopropyl | 749, 751 | 5.5 |
| 1055 | MeS-C(CH₃)₂-C(=O)- | 7-MeO, 8-Br, 2-OEt quinoline-4-yloxy | cyclopropyl | 739, 741 | 6.3 |

TABLE 1-continued

| Cpd | R³ | R² | R⁴ | (MH)⁺ | t_R (min) |
|---|---|---|---|---|---|
| 1056 | methylsulfonyl-acetyl | 8-Br-7-MeO-2-OEt-quinolin-4-yloxy | cyclopropyl | 743, 745 | 5.2 |
| 1057 | 1-hydroxy-1-(1-methylcyclohexyl)-acetyl | 7-MeO-8-Me-2-OEt-quinolin-4-yloxy | cyclopropyl | 713.4 | 5.3 |
| 1058 | 1-hydroxy-1-(1-methylcyclopentyl)-acetyl | 7-MeO-8-Me-2-OEt-quinolin-4-yloxy | cyclopropyl | 699.3 | 5.0 |
| 1059 | phenoxyethyl-carbonyl | 8-Br-7-MeO-2-OEt-quinolin-4-yloxy | cyclopropyl | 771.3, 773.3 | 6.3 |
| 1060 | phenylsulfonyl-acetyl | 8-Br-7-MeO-2-OEt-quinolin-4-yloxy | cyclopropyl | 805.2, 807.2 | 6.3 |

TABLE 1-continued

| Cpd | R³ | R² | R⁴ | (MH)⁺ | t_R (min) |
|---|---|---|---|---|---|
| 1061 | PhS-CH₂-C(O)- | 8-Br-7-MeO-2-OEt-quinolin-4-yloxy | cyclopropyl | 773.2, 775.2 | 6.3 |
| 1062 | 1,2,3,4-tetrahydronaphthalen-2-yl-C(O)- | 8-Br-7-MeO-2-OEt-quinolin-4-yloxy | cyclopropyl | 781.3, 783.3 | 6.7 |
| 1063 | PhO-CH₂-C(O)- | 8-Br-7-MeO-2-OEt-quinolin-4-yloxy | cyclopropyl | 757.3, 759.3 | 6.1 |
| 1064 | C₆F₅O-CH₂-C(O)- | 8-Br-7-MeO-2-OEt-quinolin-4-yloxy | cyclopropyl | 847.2, 849.2 | 6.6 |
| 1065 | (Et)₂CH-C(O)- | 8-Br-7-MeO-2-OEt-quinolin-4-yloxy | cyclopropyl | 721.3, 723.3 | 6.3 |

TABLE 1-continued

| Cpd | R³ | R² | R⁴ | (MH)⁺ | t_R (min) |
|---|---|---|---|---|---|
| 1066 | 2,2-dimethylbutanoyl | 8-Br-7-MeO-2-OEt-quinolin-4-yloxy | cyclopropyl | 721.3, 723.3 | 3.4 |
| 1067 | 2,2-diethylbutanoyl | 8-Br-7-MeO-2-OEt-quinolin-4-yloxy | cyclopropyl | 735.3, 737.3 | 6.4 |
| 1068 | 4-chloro-3,3-dimethylbutanoyl | 8-Br-7-MeO-2-OEt-quinolin-4-yloxy | cyclopropyl | 741.3, 743.3 | 6.2 |
| 1069 | 3,3-dichloropropanoyl | 8-Br-7-MeO-2-OEt-quinolin-4-yloxy | cyclopropyl | 733.2, 735.2, 737.2 | 5.9 |
| 1070 | (3,4-dichlorophenoxy)acetyl | 8-Br-7-MeO-2-OEt-quinolin-4-yloxy | cyclopropyl | 825.2, 827.2, 829.2 | 6.7 |

TABLE 1-continued

| Cpd | R³ | R² | R⁴ | (MH)⁺ | t_R (min) |
|---|---|---|---|---|---|
| 1071 | isobutyryl (2-methylpropanoyl) | 8-Br-7-MeO-2-OEt-quinolin-4-yloxy | cyclopropyl | 693.3 695.3 | 5.8 |
| 1072 | (3-hydroxy-4-methyl)hexanoyl | 8-Br-7-MeO-2-OEt-quinolin-4-yloxy | cyclopropyl | 737.3 739.3 | 5.9 |
| 1073 | (3-hydroxy)pentanoyl | 8-Br-7-MeO-2-OEt-quinolin-4-yloxy | cyclopropyl | 709.3 711.3 | 5.3 |
| 1074 | (2-cyclohexyl-2-hydroxy)acetyl | 8-Br-7-MeO-2-OEt-quinolin-4-yloxy | cyclopropyl | 763.3 765.3 | 6.3 |
| 1075 | (3-hydroxy)butanoyl | 8-Br-7-MeO-2-OEt-quinolin-4-yloxy | cyclopropyl | 695.3 697.3 | 5.1 |

TABLE 1-continued

| Cpd | R³ | R² | R⁴ | (MH)⁺ | t_R (min) |
|---|---|---|---|---|---|
| 1076 | 1-hydroxycyclopropyl ketone | 8-Br-7-MeO-2-OEt-quinolin-4-yloxy | cyclopropyl | 707.3 709.3 | 5.2 |
| 1077 | 2-hydroxy-2-methylpropanoyl | 8-Br-7-MeO-2-OEt-quinolin-4-yloxy | cyclopropyl | 709.3 711.3 | 5.3 |
| 1078 | 3-hydroxy-2,2-dimethylpropanoyl | 8-Br-7-MeO-2-OEt-quinolin-4-yloxy | cyclopropyl | 723.2 725.3 | 5.4 |
| 1079 | hydroxyacetyl | 8-Br-7-MeO-2-OEt-quinolin-4-yloxy | cyclopropyl | 681.2 683.2 | 5.0 |
| 1080 | 3-ethyl-3-hydroxypentanoyl | 8-Br-7-MeO-2-OEt-quinolin-4-yloxy | cyclopropyl | 737.3 739.3 | 5.9 |

TABLE 1-continued

| Cpd | R³ | R² | R⁴ | (MH)⁺ | t_R (min) |
|---|---|---|---|---|---|
| 1081 | benzyl CH(OH)C(O)- | 8-Br-7-MeO-2-OEt-quinolin-4-yloxy | cyclopropyl | 771.3 773.3 | 6.0 |
| 1082 | (1H-imidazol-4-yl)methyl CH(OH)C(O)- | 8-Br-7-MeO-2-OEt-quinolin-4-yloxy | cyclopropyl | 761.3 763.2 | 4.5 |
| 1083 | isobutyl CH(OH)C(O)- | 8-Br-7-MeO-2-OEt-quinolin-4-yloxy | cyclopropyl | 737.3 739.3 | 5.9 |
| 1084 | isopropyl CH(OH)C(O)- | 8-Br-7-MeO-2-OEt-quinolin-4-yloxy | cyclopropyl | 723.3 725.3 | 5.6 |
| 1085 | tBu-CH(OH)C(O)- | 8-Cl-2-OEt-quinolin-4-yloxy | cyclopropyl | 663.4 | 6.0 |

TABLE 1-continued
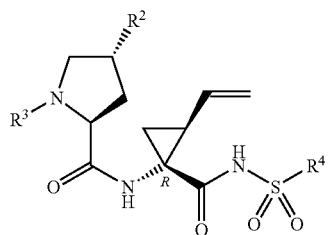
| Cpd | R³ | R² | R⁴ | (MH)⁺ | t_R (min) |
|---|---|---|---|---|---|
| 1086 | | OMe-quinoline-OEt, O- | cyclopropyl | 659.4 | 3.8 |
| 1087 | | Cl-quinoline-OEt, O- | 1-methylcyclopropyl | 677.4 | 6.2 |
| 1088 | | OMe-quinoline-OEt, O- | 1-methylcyclopropyl | 673.4 | 4.0 |
| 1089 | | MeO-, Me-quinoline-OEt, O- | 1-ethylcyclopropyl | 701.4 | 5.0 |
| 1090 | | MeO-, Br-quinoline-OEt, O- | 1-methylcyclopropyl | 753.2 | 5.8 |

TABLE 1-continued

| Cpd | R³ | R² | R⁴ | (MH)⁺ | t_R (min) |
|---|---|---|---|---|---|
| 1091 | 3,3-dimethyl-4-hydroxy-pentanoyl (ethyl, HO, O) | 7-MeO, 8-Me quinoline, 2-OEt, 4-O | cyclopropyl | 687.3 | 4.8 |
| 1092 | 3-ethyl-3-vinyl-4-hydroxy-pentanoyl | 7-MeO, 8-Me quinoline, 2-OEt, 4-O | cyclopropyl | 701.3 | 5.1 |
| 1093 | 3,3-dimethyl-4-hydroxy-pentanoyl | 7-MeO, 8-Br quinoline, 2-OEt, 4-O | cyclopropyl | 753.2 | 6.0 |
| 1094 | 3-ethyl-3-vinyl-4-hydroxy-pentanoyl | 7-MeO, 8-Br quinoline, 2-OEt, 4-O | cyclopropyl | 767.2 | 6.3 |
| 1095 | 3,3-dimethyl-4-hydroxy-pentanoyl | 7-MeO, 8-Me quinoline, 2-OEt, 4-O | 1-methylcyclopropyl | 701.4 | 4.9 |

TABLE 1-continued

| Cpd | R³ | R² | R⁴ | (MH)⁺ | t_R (min) |
|---|---|---|---|---|---|
| 1096 | (ethyl, ethyl, HO, C=O group) | 7-MeO, 8-methyl quinoline, 2-OEt, 4-O | 1-methylcyclopropyl | 715.4 | 5.2 |
| 1097 | (ethyl, methyl, HO, C=O group) | 7-MeO, 8-Br quinoline, 2-OEt, 4-O | 1-methylcyclopropyl | 767.2 | 6.1 |
| 1098 | (ethyl, ethyl, HO, C=O group) | 7-MeO, 8-Br quinoline, 2-OEt, 4-O | 1-methylcyclopropyl | 781.3 | 6.4 |
| 1099 | (SMe, dimethyl, HO, C=O group) | 7-MeO, 8-methyl quinoline, 2-OEt, 4-O | cyclopropyl | 705.3 | 4.5 |
| 1100 | (SMe, dimethyl, HO, C=O group) | 7-MeO, 8-methyl quinoline, 2-OEt, 4-O | 1-methylcyclopropyl | 719.3 | 4.6 |

TABLE 1-continued

| Cpd | R³ | R² | R⁴ | (MH)⁺ | t_R (min) |
|---|---|---|---|---|---|
| 1101 | methylthio-dimethyl-hydroxy-ketone group | 8-Br, 7-MeO, 2-OEt quinoline-4-oxy | cyclopropyl | 771.1 | 5.7 |
| 1102 | methylthio-dimethyl-hydroxy-ketone group | 8-Br, 7-MeO, 2-OEt quinoline-4-oxy | 1-methylcyclopropyl | 785.2 | 5.8 |
| 1103 | tert-butyl-hydroxy-ketone group | 8-Me, 7-MeO, 2-OEt quinoline-4-oxy | CH₂-N(Me)₂ | 676 | 4.4 |
| 1104 | tert-butyl-hydroxy-ketone group | 8-Me, 7-MeO, 2-OEt quinoline-4-oxy | CH₂-(2,5-dihydropyrrol-1-yl) | 700 | 4.7 |
| 1105 | tert-butyl-hydroxy-ketone group | 8-Me, 7-MeO, 2-OEt quinoline-4-oxy | CH₂-N(Me)(OMe) | 692 | 4.6 |

TABLE 1-continued

| Cpd | R³ | R² | R⁴ | (MH)⁺ | $t_R$ (min) |
|---|---|---|---|---|---|
| 1106 | (HO, tBu, C=O) | 8-SMe, 2-OEt, 4-O- quinoline | cyclopropyl | 675.0 | 7.0 |

TABLE 2

| Cpd | R³ | R² | R⁴ | (MH)⁺ | $t_R$ (min) |
|---|---|---|---|---|---|
| 2001 | (HO, tBu, C=O) | 8-SMe, 2-OEt, 4-O- quinoline | cyclopropyl | 691.0 | 7.2 |

What is claimed is:

1. An azalactone compound of formula (III):

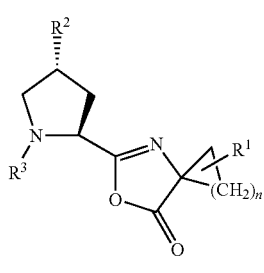

(III)

wherein n is 1 or 2;

R¹ is $(C_{1-6})$alkyl $(C_{2-6})$alkenyl, or $(C_{2-6})$alkynyl; wherein the $(C_{1-6})$alkyl, $(C_{2-6})$alkenyl, and $(C_{2-6})$alkynyl are optionally substituted at one or more substitutable positions with from one to three halogen atoms;

R² is selected from —NH—R²⁰, —O—R²⁰, —S—R²⁰, —SO—R²⁰, —SO₂—R²⁰, —OCH₂—R²⁰, and —CH₂O—R²⁰, wherein R²⁰ is aryl or Het, wherein the aryl and Het are optionally substituted with R²⁰⁰, wherein R²⁰⁰ is one to four substituents each independently selected from H, halogen, cyano, $(C_{1-6})$alkyl, $(C_{3-7})$ cycloalkyl, aryl-$(C_{1-6})$alkyl-, aryl, Het, oxo, thioxo, —OR²⁰¹, —SR²⁰¹, —SOR²⁰¹, —SO₂R²⁰¹, —N(R²⁰²)R²⁰¹, and —CON(R²⁰²)R²⁰¹; wherein each of the alkyl, cycloalkyl, aryl and Het is optionally further substituted with $R^{2000}$;

$R^{201}$ in each case is independently selected from H, $(C_{1-6})$alkyl, aryl, $(C_{2-4})$alkenyl, $(C_{2-4})$alkynyl, —CO—$(C_{1-6})$alkyl and —CO—O—$(C_{1-6})$alkyl, wherein each of the alkyl and aryl is optionally further substituted with $R^{2000}$;

$R^{202}$ is H or $(C_{1-6})$alkyl;

$R^{2000}$ is one to three substituents each independently selected from halogen, $R^{2003}$, aryl, Het, —OR$^{2001}$, —SR$^{2001}$, —SOR$^{2001}$, —SO$_2$R$^{2001}$, cyano and —N(R$^{2002}$)(R$^{2001}$), wherein the aryl and Het are each optionally substituted with one, two or three substituents each independently selected from $(C_{1-6})$alkyl and —O—$(C_{1-6})$alkyl;

$R^{2001}$ in each case is independently selected from aryl, aryl-$(C_{1-6})$alkyl-, —C(O)—R$^{2003}$, —C(O)O—R$^{2003}$, —CON(R$^{2002}$)(R$^{2004}$) and R$^{2004}$;

$R^{2002}$ in each case is independently selected from H and $(C_{1-6})$alkyl;

$R^{2003}$ in each case is independently selected from $(C_{1-8})$alkyl, $(C_{3-7})$cycloalkyl and $(C_{3-7})$cycloalkyl-$(C_{1-4})$alkyl-, wherein the $(C_{3-7})$cycloalkyl and $(C_{3-7})$cycloalkyl-$(C_{1-4})$alkyl- are each optionally substituted with one to three substituents each independently selected from $(C_{1-3})$alkyl; and $R^{2004}$ in each case is independently selected from H and $R^{2003}$;

$R^3$ is selected from:
(i) —C(O)OR$^{31}$ wherein $R^{31}$ is $(C_{1-6})$alkyl or aryl, wherein the $(C_{1-6})$alkyl is optionally substituted with one to three halogen substituents;
(ii) —C(O)NR$^{32}$R$^{33}$, wherein $R^{32}$ and $R^{33}$ are each independently selected from H, $(C_{1-6})$alkyl, and Het;
(iii) —SO$_v$R$^{34}$ wherein v is 1 or 2 and $R^{34}$ is selected from: $(C_{1-6})$alkyl, aryl, Het, and NR$^{32}$R$^{33}$ wherein $R^{32}$ and $R^{33}$ are as defined above; and
(iv) —C(O)—R$^{35}$, wherein $R^{35}$ is selected from $(C_{1-8})$alkyl, $(C_{3-7})$cycloalkyl, $(C_{3-7})$cycloalkyl-$(C_{1-4})$alkyl-, aryl, aryl-$(C_{1-6})$alkyl-, Het and Het-$(C_{1-6})$alkyl, each of which are optionally substituted with one or more substituents each independently selected from halo, $(C_{1-6})$alkyl, $(C_{3-7})$cycloalkyl, aryl, Het, hydroxyl, —O—$(C_{1-6})$alkyl, —S—$(C_{1-6})$alkyl, —SO—$(C_{1-6})$alkyl, —SO$_2$—$(C_{1-6})$alkyl, —O-aryl, —S-aryl, —SO-aryl and —SO$_2$-aryl, wherein the aryl portion of the —O-aryl, —S-aryl, —SO-aryl and —SO$_2$-aryl are each optionally substituted with one to five halo substituents.

2. The compound according to claim 1 wherein n is 1.

3. The compound according to claim 1 wherein $R^1$ is $(C_{2-6})$alkenyl or $(C_{2-6})$alkyl.

4. The compound according to claim 3 wherein $R^1$ is ethenyl or ethyl.

5. The compound according to claim 1 wherein $R^2$ is selected from —O—$R^{20}$ and —S—$R^{20}$, wherein $R^{20}$ is defined as in claim 1, the $R^{20}$ being optionally substituted with $R^{200}$, wherein $R^{200}$ is defined as in claim 1.

6. The compound according to claim 5 wherein $R^2$ is —O—$R^{20}$, wherein $R^{20}$ is defined as in claim 5, the $R^{20}$ being optionally substituted with $R^{200}$, wherein $R^{200}$ is defined as in claim 5.

7. The compound according to claim 6 wherein $R^{20}$ is Het selected from

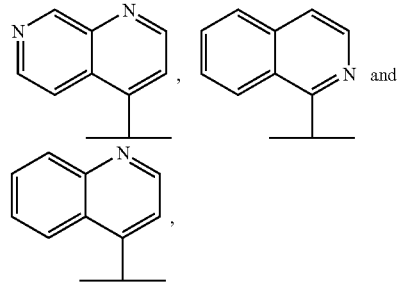

the Het being unsubstituted or substituted with $R^{200}$, wherein $R^{200}$ is defined as in claim 6.

8. The compound according to claim 7 wherein $R^{200}$ is one to four substituents each independently selected from H, halogen, cyano, $(C_{1-6})$alkyl, aryl, Het, —OR$^{201}$, —SR$^{201}$, —SOR$^{201}$ and —SO$_2$R$^{201}$; wherein $(C_{1-6})$alkyl, aryl and Het are each optionally further substituted with $R^{2000}$;

$R^{201}$ is in each case independently selected from $(C_{1-6})$alkyl optionally further substituted with $R^{2000}$;

$R^{2000}$ is in each case independently one to three substituents each independently selected from halogen, $R^{2003}$, aryl, Het, —OR$^{2001}$, SR$^{2001}$, —SOR$^{2001}$, —SO$_2$R$^{2001}$ cyano and —N(R$^{2002}$)(R$^{2001}$); wherein the aryl and Het are each optionally substituted with one, two or three substituents each independently selected from $(C_{1-6})$alkyl and —O—$(C_{1-6})$alkyl;

$R^{2001}$ is in each case independently selected from aryl, aryl-$(C_{1-6})$alkyl-, —C(O)—R$^{2003}$, —C(O)O—R$^{2003}$— CON(R$^{2002}$)(R$^{2004}$) and R$^{2004}$;

$R^{2002}$ is in each case independently selected from H and $(C_{1-6})$alkyl;

$R^{2003}$ is in each case independently selected from $(C_{1-8})$alkyl, $(C_{3-7})$cycloalkyl and $(C_{3-7})$cycloalkyl-$(C_{1-4})$alkyl-, wherein the $(C_{3-7})$cycloalkyl and $(C_{3-7})$cycloalkyl-$(C_{1-4})$alkyl- are each optionally substituted with one to three substituents each independently selected from $(C_{1-3})$alkyl;

$R^{2004}$ is in each case independently selected from H and $R^{2003}$; and

Het is in each case independently a 5- 6- or 7-membered monocyclic saturated, unsaturated or aromatic heterocycle containing 1 to 4 heteroatoms each independently selected from N, O and S.

9. The compound according to claim 7 wherein $R^{20}$ is Het of the formula

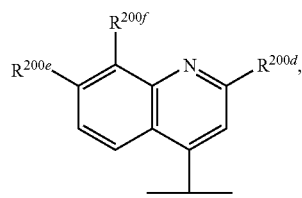

wherein
$R^{200d}$ is H, aryl, Het, or —OR$^{201}$, wherein Het is a 5- 6- or 7-membered monocyclic saturated, unsaturated or aromatic heterocycle containing 1 to 4 heteroatoms each independently selected from N, O and S and wherein the aryl and Het are each optionally further substituted with $R^{2000}$;

$R^{200e}$ is H or —$OR^{201}$; and $R^{200f}$ is H, $(C_{1-6})$alkyl, halogen, —$SR^{201}$, —$SO_2R^{201}$, or —$OR^{201}$; wherein the $(C_{1-6})$alkyl is optionally further substituted with $R^{2000}$; wherein $R^{201}$ is in each case independently selected from $(C_{1-6})$alkyl optionally further substituted with $R^{2000}$;

$R^{2000}$ is in each case independently one to three substituents each independently selected from halogen, $(C_{3-7})$cycloalkyl, aryl, —$OR^{2001}$, cyano, and —$N(R^{2002})(R^{2001})$;

$R^{2001}$ is in each case independently selected from H, $(C_{1-6})$alkyl and —$COR^{2003}$;

$R^{2002}$ is in each case independently selected from H and $(C_{1-6})$alkyl; and $R^{2003}$ is in each case independently selected from $(C_{1-8})$alkyl, $(C_{3-7})$cycloalkyl and $(C_{3-7})$cycloalkyl-$(C_{1-4})$alkyl-.

10. The compound according to claim 1 wherein $R^3$ is —C(O)$OR^{31}$, wherein $R^{31}$ is defined as in claim 1.

11. The compound according to claim 10 wherein $R^{31}$ is $(C_{1-6})$alkyl optionally substituted with one to three halogen substituents.

12. The compound according to claim 1 wherein $R^3$ is —C(O)$NR^{32}R^{33}$, wherein $R^{32}$ and $R^{33}$ are defined as in claim 1.

13. The compound according to claim 12 wherein $R^{32}$ and $R^{33}$ are each independently selected from H, $(C_{1-6})$alkyl, and Het, wherein Het is a 5- or 6-membered saturated, unsaturated or aromatic monocyclic heterocycle containing one to three heteroatoms each independently selected from N, O and S.

14. The compound according to claim 1 wherein $R^3$ is $SO_vR^{34}$, wherein v and $R^{34}$ are defined as in claim 1.

15. The compound according to claim 14 wherein v is 2 and $R^{34}$ is selected from $(C_{1-6})$alkyl and $NR^{32}R^{33}$, where $R^{32}$ and $R^{33}$ are each independently selected from H and $(C_{1-6})$alkyl.

16. The compound according to claim 1 wherein $R^3$ is —C(O)—$R^{35}$, wherein $R^{35}$ is defined as in claim 1.

17. The compound according to claim 16 wherein $R^{35}$ is selected from:

(a) $(C_{1-8})$alkyl optionally substituted with one to three substituents each independently selected from halo, hydroxyl, —O—$(C_{1-6})$alkyl, —S—$(C_{1-6})$alkyl, —SO—$(C_{1-6})$alkyl, —$SO_2$—$(C_{1-6})$alkyl, —O-phenyl, —S-phenyl, —SO-phenyl and —$SO_2$-phenyl, wherein the phenyl portion of the —O-phenyl, —S-phenyl, —SO-phenyl and —$SO_2$-phenyl are each optionally substituted with one to five halo substituents;

(b) $(C_{3-7})$cycloalkyl or $(C_{3-7})$cycloalkyl-$(C_{1-4})$alkyl-, each of which being optionally substituted with one to three substituents each independently selected from halo, $(C_{1-6})$alkyl, aryl and hydroxyl; and (c) phenyl, tetrahydronaphthyl, phenyl-$(C_{1-6})$alkyl- or Het-$(C_{1-6})$alkyl-, each of which being optionally substituted with one to three substituents each independently selected from $(C_{1-6})$alkyl and hydroxyl; wherein Het is a 5- or 6-membered monocyclic heterocycle which is saturated, unsaturated or aromatic, containing one to three heteroatoms each independently selected from N, O and S.

18. The compound according to claim 17 wherein $R^{35}$ is selected from $(C_{1-8})$alkyl, $(C_{3-7})$cycloalkyl-$(C_{1-4})$alkyl-, phenyl-$(C_{1-6})$alkyl- and Het-$(C_{1-6})$alkyl-, each of which being optionally substituted with hydroxyl.

19. The compound according to claim 18 wherein $R^{35}$ is $(C_{1-6})$alkyl optionally substituted with hydroxyl.

* * * * *